United States Patent
Ferrara

(10) Patent No.: US 12,269,878 B2
(45) Date of Patent: Apr. 8, 2025

(54) NOTCH4 ANTIBODIES, COMPOSITIONS, AND METHODS FOR TREATING AIRWAY INFLAMMATION

(71) Applicant: Alcea Therapeutics, Inc., New York, NY (US)

(72) Inventor: Fortunato Ferrara, Santa Fe, NM (US)

(73) Assignee: Alcea Therapeutics, Inc., New York, NY (US)

( * ) Notice: Subject to any disclaimer, the term of this patent is extended or adjusted under 35 U.S.C. 154(b) by 0 days.

(21) Appl. No.: 18/651,002

(22) Filed: Apr. 30, 2024

(65) Prior Publication Data

US 2024/0309086 A1 Sep. 19, 2024

Related U.S. Application Data

(63) Continuation of application No. PCT/EP2023/077642, filed on Oct. 5, 2023.

(60) Provisional application No. 63/378,479, filed on Oct. 5, 2022.

(51) Int. Cl.
| | |
|---|---|
| A61K 39/395 | (2006.01) |
| A61P 11/00 | (2006.01) |
| A61P 11/06 | (2006.01) |
| C07K 16/28 | (2006.01) |

(52) U.S. Cl.
CPC .......... C07K 16/28 (2013.01); A61K 39/3955 (2013.01); A61P 11/06 (2018.01); C07K 16/2863 (2013.01); C07K 2317/21 (2013.01); C07K 2317/56 (2013.01); C07K 2317/565 (2013.01); C07K 2317/76 (2013.01)

(58) Field of Classification Search
CPC ............ A61K 2039/505; A61K 39/395; A61K 39/3955; A61P 11/00; A61P 11/06; C07K 16/28; C07K 16/2863; C07K 2317/56; C07K 2317/565; C07K 2317/76
See application file for complete search history.

(56) References Cited

U.S. PATENT DOCUMENTS

| | | | |
|---|---|---|---|
| 4,816,567 A | 3/1989 | Cabilly et al. | |
| 5,565,332 A | 10/1996 | Hoogenboom et al. | |
| 5,571,894 A | 11/1996 | Wels et al. | |
| 5,573,905 A | 11/1996 | Lerner et al. | |
| 5,587,458 A | 12/1996 | King et al. | |
| 5,641,870 A | 6/1997 | Rinderknecht et al. | |
| 5,739,277 A | 4/1998 | Presta et al. | |
| 5,869,046 A | 2/1999 | Presta et al. | |
| 2017/0290844 A1* | 10/2017 | Beinke .................. | C07K 16/28 |

FOREIGN PATENT DOCUMENTS

| | | |
|---|---|---|
| WO | WO-93/16185 A2 | 8/1993 |
| WO | WO-98/57621 A1 | 12/1998 |
| WO | WO-2016046151 A1 * | 3/2016 ............. A61K 31/55 |
| WO | WO-2018/039107 A1 | 3/2018 |
| WO | WO-2019/178488 A1 | 9/2019 |
| WO | WO-2021/167883 A1 | 8/2021 |
| WO | WO-2022/081971 A1 | 4/2022 |

OTHER PUBLICATIONS

Aghasafari et al. A review of inflammatory mechanism in airway diseases. Inflamm Res 68: 59-74, 2019.*
Antar et al. Examining the contribution of Notch signaling to lung disease development. Naunyn-Schmiedeberg's Archives Pharmacol, doi.org/10.1007/s00210-024-03105-8, 2024.*
Brusselle et al. Targeting Immune Pathways for Therapy in Asthma and Chronic Obstructive Pulmonary Disease. Ann Am Thorac Soc 11(Suppl 5): S322-S328, 2014.*
Chilosi et al. The pathogenesis of COPD and IPF: Distinct horns of the same devil? Respir Res 13: 3, 2012 (9 total pages).*
Di Stefano et al. Upregulation of Notch Signaling and Cell-Differentiation Inhibitory Transcription Factors in Stable Chronic Obstructive Pulmonary Disease Patients Int J Mol Sci 25: 3287, 2024 (16 total pages).*
Garth et al. Targeting Cytokines as Evolving Treatment Strategies in Chronic Inflammatory Airway Diseases. Int J Mol Sci 19: 3402, 2018 (19 total pages).*
Guseh et al. Notch signaling promotes airway mucous metaplasia and inhibits alveolar development. Dev 136: 1751-1759, 2009.*
Huang et al. Multi-Faceted Notch in Allergic Airway Inflammation. Int J Mol Sci 20: 3508, 2019 (17 total pages).*
Kiyokawa et al. Notch signaling in the mammalian respiratory system, specifically the trachea and lungs, in development, homeostasis, regeneration, and disease. Develop Growth Differ 62: 67-69, 2020.*
Tilley et al. Down-regulation of the Notch Pathway in Human Airway Epithelium in Association with Smoking and Chronic Obstructive Pulmonary Disease. Am J Respir Crit Care Med 179: 457-466, 2009.*
Xia et al. A Jagged 1-Notch 4 molecular switch mediates airway inflammation induced by ultrafine particles. J Allergy Clin Immunol 142: 1243-1256, 2018.*
Zong et al. Notch signaling in lung diseases: focus on Notch1 and Notch3. Ther Adv Respir Dis 10(5): 468-484, 2016.*
Zhou et al. Blockade of Notch Signalling by γ-Secretase Inhibitor in Lung T Cells of Asthmatic Mice Affects T Cell Differentiation and Pulmonary Inflammation. Inflamm 38(3): 1281-1288, 2015.*
Benamar M, et al. A common IL-4 receptor variant promotes asthma severity via a Treg cell GRB2-IL-6-Notch4 circuit. Allergy. Nov. 2022;77(11):3377-3387.
Griffiths AD, et al. Human anti-self antibodies with high specificity from phage display libraries. EMBO J. Feb. 1993;12(2):725-34.
Hammad H, Lambrecht BN. Wnt and Hippo pathways in regulatory T cells: a NOTCH above in asthma. Nat Immunol. Nov. 2020;21(11):1313-1314.

(Continued)

Primary Examiner — Bridget E Bunner
(74) Attorney, Agent, or Firm — Goodwin Procter LLP

(57) ABSTRACT

Antibodies specific to Notch4 and related methods of treating conditions such as airway inflammation.

25 Claims, 12 Drawing Sheets

Specification includes a Sequence Listing.

(56) References Cited

OTHER PUBLICATIONS

Harb H, et al. A regulatory T cell Notch4-GDF15 axis licenses tissue inflammation in asthma. Nat Immunol. Nov. 2020;21(11):1359-1370.
Harb H, et al. Notch4 signaling limits regulatory T-cell-mediated tissue repair and promotes severe lung inflammation in viral infections. Immunity. Jun. 8, 2021;54(6):1186-1199.e7.
International Search Report mailed Mar. 5, 2024, for International Application No. PCT/EP2023/077642 filed Oct. 5, 2023 (7 pages).

\* cited by examiner

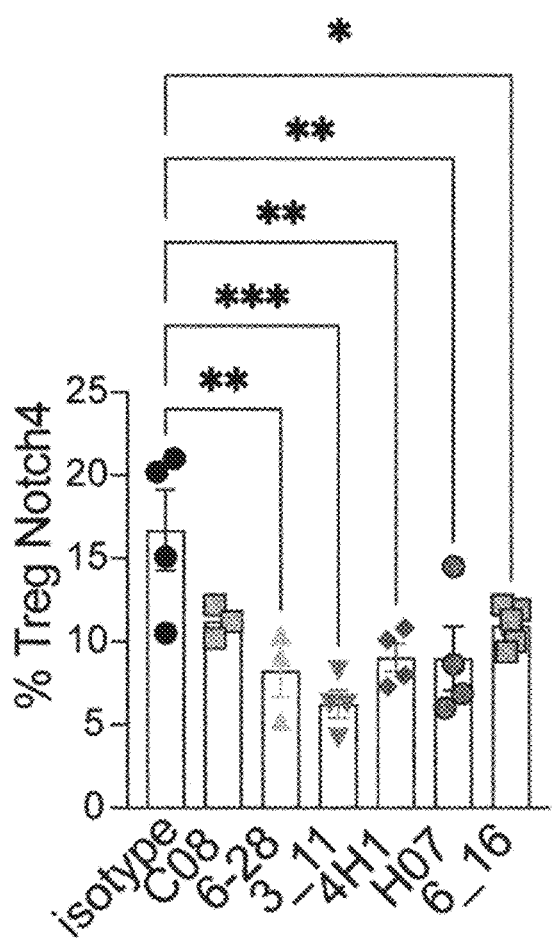
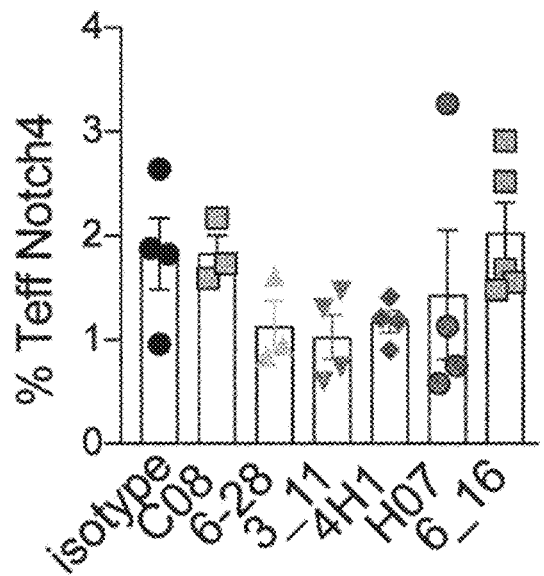
FIG. 4B
FIG. 4C

NOTCH4 ANTIBODIES, COMPOSITIONS, AND METHODS FOR TREATING AIRWAY INFLAMMATION

CROSS-REFERENCE TO RELATED APPLICATIONS

This application is a continuation of PCT/EP2023/077642 (filed Oct. 5, 2023), which claims the benefit of and priority to U.S. Provisional Patent Application No. 63/378,479 (filed on Oct. 5, 2022), the disclosures of each which are incorporated by reference herein in their entirety for all purposes.

SEQUENCE LISTING

The present specification makes reference to a Sequence listing which has been submitted electronically in XML format and is hereby incorporated by reference in its entirety. Said XML file, created on Apr. 29, 2024, is named ALC-050WOC1_Sequence_listing.xml, and is 135,783 bytes in size.

BACKGROUND

Chronic airway inflammation is a general feature of numerous conditions, such as asthma, chronic obstructive pulmonary disorder (COPD), cystic fibrosis (CF), and bronchopulmonary dysplasia (BPD). Current strategies to treat these chronic pathologies focus in large part on inhibiting pro-inflammatory pathways systemically. One challenge for such strategies is to effectively shut down part of the immune response without leaving patients vulnerable to opportunistic pathogens or crippled by side effects. Due to different profiles of inflammatory responses, however, no single strategy has so far proven to be widely effective, and response rates for existing therapies have generally been poor.

Improved, targeted therapies for airway inflammation and related disorders are still needed.

SUMMARY

In one aspect, provided are antibodies and antigen-binding fragments thereof that are capable of binding to Notch4 (also referred to herein as Notch4 antibodies and Notch4-binding fragments thereof, respectively). For example, in some embodiments, provided are antibodies or antigen-binding fragment thereof that are capable of binding to Notch4, comprising:

(a) (i) a heavy chain variable domain ($V_H$) comprising complementarity-determining regions:
  CDR-H1 comprising the amino acid sequence of SEQ ID NO: 2 or a sequence differing in 1 or 2 amino acids therefrom,
  CDR-H2 comprising the amino acid sequence of SEQ ID NO: 3 or a sequence differing in 1 or 2 amino acids therefrom, and
  CDR-H3 comprising the amino acid sequence of SEQ ID NO: 4 or a sequence differing in 1 or 2 amino acids therefrom; and
(ii) a light chain variable domain ($V_K$) comprising complementarity-determining regions:
  CDR-L1 comprising the amino acid sequence of SEQ ID NO: 6 or a sequence differing in 1 or 2 amino acids therefrom,
  CDR-L2 comprising the amino acid sequence of SEQ ID NO: 7 or a sequence differing in 1 or 2 amino acids therefrom, and
  CDR-L3 comprising the amino acid sequence of SEQ ID NO: 8 or a sequence differing in 1 or 2 amino acids therefrom;

(b) (i) a $V_H$ comprising complementarity-determining regions:
  CDR-H1 comprising the amino acid sequence of SEQ ID NO: 10 or a sequence differing in 1 or 2 amino acids therefrom,
  CDR-H2 comprising the amino acid sequence of SEQ ID NO: 11 or a sequence differing in 1 or 2 amino acids therefrom, and
  CDR-H3 comprising the amino acid sequence of SEQ ID NO: 12 or a sequence differing in 1 or 2 amino acids therefrom; and
(ii) a $V_K$ comprising complementarity-determining regions:
  CDR-L1 comprising the amino acid sequence of SEQ ID NO: 14 or a sequence differing in 1 or 2 amino acids therefrom,
  CDR-L2 comprising the amino acid sequence of SEQ ID NO: 15 or a sequence differing in 1 or 2 amino acids therefrom, and
  CDR-L3 comprising the amino acid sequence of SEQ ID NO: 16 or a sequence differing in 1 or 2 amino acids therefrom;

(c) (i) a $V_H$ comprising complementarity-determining regions:
  CDR-H1 comprising the amino acid sequence of SEQ ID NO: 18 or a sequence differing in 1 or 2 amino acids therefrom,
  CDR-H2 comprising the amino acid sequence of SEQ ID NO: 19 or a sequence differing in 1 or 2 amino acids therefrom, and
  CDR-H3 comprising the amino acid sequence of SEQ ID NO: 20 or a sequence differing in 1 or 2 amino acids therefrom; and
(ii) a $V_K$ comprising complementarity-determining regions:
  CDR-L1 comprising the amino acid sequence of SEQ ID NO: 22 or a sequence differing in 1 or 2 amino acids therefrom,
  CDR-L2 comprising the amino acid sequence of SEQ ID NO: 23 or a sequence differing in 1 or 2 amino acids therefrom, and
  CDR-L3 comprising the amino acid sequence of SEQ ID NO: 24 or a sequence differing in 1 or 2 amino acids therefrom;

(d) (i) a $V_H$ comprising complementarity-determining regions:
  CDR-H1 comprising the amino acid sequence of SEQ ID NO: 26 or a sequence differing in 1 or 2 amino acids therefrom,
  CDR-H2 comprising the amino acid sequence of SEQ ID NO: 27 or a sequence differing in 1 or 2 amino acids therefrom, and
  CDR-H3 comprising the amino acid sequence of SEQ ID NO: 28 or a sequence differing in 1 or 2 amino acids therefrom; and
(ii) a $V_K$ comprising complementarity-determining regions:
  CDR-L1 comprising the amino acid sequence of SEQ ID NO: 30 or a sequence differing in 1 or 2 amino acids therefrom, CDR-L2 comprising the amino acid sequence of SEQ ID NO: 31 or a sequence differing in 1 or 2 amino acids therefrom, and
CDR-L3 comprising the amino acid sequence of SEQ ID NO: 32 or a sequence differing in 1 or 2 amino acids therefrom;

(e) (i) a $V_H$ comprising complementarity-determining regions:
CDR-H1 comprising the amino acid sequence of SEQ ID NO: 34 or a sequence differing in 1 or 2 amino acids therefrom,
CDR-H2 comprising the amino acid sequence of SEQ ID NO: 35 or a sequence differing in 1 or 2 amino acids therefrom, and
CDR-H3 comprising the amino acid sequence of SEQ ID NO: 36 or a sequence differing in 1 or 2 amino acids therefrom; and
(ii) a $V_K$ comprising complementarity-determining regions:
CDR-L1 comprising the amino acid sequence of SEQ ID NO: 38 or a sequence differing in 1 or 2 amino acids therefrom,
CDR-L2 comprising the amino acid sequence of SEQ ID NO: 39 or a sequence differing in 1 or 2 amino acids therefrom, and
CDR-L3 comprising the amino acid sequence of SEQ ID NO: 40 or a sequence differing in 1 or 2 amino acids therefrom;

(f) (i) a $V_H$ comprising complementarity-determining regions:
CDR-H1 comprising the amino acid sequence of SEQ ID NO: 42 or a sequence differing in 1 or 2 amino acids therefrom,
CDR-H2 comprising the amino acid sequence of SEQ ID NO: 43 or a sequence differing in 1 or 2 amino acids therefrom, and
CDR-H3 comprising the amino acid sequence of SEQ ID NO: 44 or a sequence differing in 1 or 2 amino acids therefrom; and
(ii) a $V_K$ comprising complementarity-determining regions:
CDR-L1 comprising the amino acid sequence of SEQ ID NO: 46 or a sequence differing in 1 or 2 amino acids therefrom,
CDR-L2 comprising the amino acid sequence of SEQ ID NO: 47 or a sequence differing in 1 or 2 amino acids therefrom, and
CDR-L3 comprising the amino acid sequence of SEQ ID NO: 48 or a sequence differing in 1 or 2 amino acids therefrom;

(g) (i) a $V_H$ comprising complementarity-determining regions:
CDR-H1 comprising the amino acid sequence of SEQ ID NO: 50 or a sequence differing in 1 or 2 amino acids therefrom,
CDR-H2 comprising the amino acid sequence of SEQ ID NO: 51 or a sequence differing in 1 or 2 amino acids therefrom, and
CDR-H3 comprising the amino acid sequence of SEQ ID NO: 52 or a sequence differing in 1 or 2 amino acids therefrom; and
(ii) a $V_K$ comprising complementarity-determining regions:
CDR-L1 comprising the amino acid sequence of SEQ ID NO: 54 or a sequence differing in 1 or 2 amino acids therefrom,
CDR-L2 comprising the amino acid sequence of SEQ ID NO: 55 or a sequence differing in 1 or 2 amino acids therefrom, and
CDR-L3 comprising the amino acid sequence of SEQ ID NO: 56 or a sequence differing in 1 or 2 amino acids therefrom;

(h) (i) a $V_H$ comprising complementarity-determining regions:
CDR-H1 comprising the amino acid sequence of SEQ ID NO: 58 or a sequence differing in 1 or 2 amino acids therefrom,
CDR-H2 comprising the amino acid sequence of SEQ ID NO: 59 or a sequence differing in 1 or 2 amino acids therefrom, and
CDR-H3 comprising the amino acid sequence of SEQ ID NO: 60 or a sequence differing in 1 or 2 amino acids therefrom; and
(ii) a $V_K$ comprising complementarity-determining regions:
CDR-L1 comprising the amino acid sequence of SEQ ID NO: 62 or a sequence differing in 1 or 2 amino acids therefrom,
CDR-L2 comprising the amino acid sequence of SEQ ID NO: 63 or a sequence differing in 1 or 2 amino acids therefrom, and
CDR-L3 comprising the amino acid sequence of SEQ ID NO: 64 or a sequence differing in 1 or 2 amino acids therefrom;

(i) (i) a comprising complementarity-determining regions:
CDR-H1 comprising the amino acid sequence of SEQ ID NO: 66 or a sequence differing in 1 or 2 amino acids therefrom,
CDR-H2 comprising the amino acid sequence of SEQ ID NO: 67 or a sequence differing in 1 or 2 amino acids therefrom, and
CDR-H3 comprising the amino acid sequence of SEQ ID NO: 68 or a sequence differing in 1 or 2 amino acids therefrom; and
(ii) a $V_K$ comprising complementarity-determining regions:
CDR-L1 comprising the amino acid sequence of SEQ ID NO: 70 or a sequence differing in 1 or 2 amino acids therefrom,
CDR-L2 comprising the amino acid sequence of SEQ ID NO: 71 or a sequence differing in 1 or 2 amino acids therefrom, and
CDR-L3 comprising the amino acid sequence of SEQ ID NO: 72 or a sequence differing in 1 or 2 amino acids therefrom;

(j) (i) a $V_H$ comprising complementarity-determining regions:
CDR-H1 comprising the amino acid sequence of SEQ ID NO: 74 or a sequence differing in 1 or 2 amino acids therefrom,
CDR-H2 comprising the amino acid sequence of SEQ ID NO: 75 or a sequence differing in 1 or 2 amino acids therefrom, and
CDR-H3 comprising the amino acid sequence of SEQ ID NO: 76 or a sequence differing in 1 or 2 amino acids therefrom; and
(ii) a $V_K$ comprising complementarity-determining regions:
CDR-L1 comprising the amino acid sequence of SEQ ID NO: 78 or a sequence differing in 1 or 2 amino acids therefrom, CDR-L2 comprising the amino acid sequence of SEQ ID NO: 79 or a sequence differing in 1 or 2 amino acids therefrom, and CDR-L3 comprising the amino acid sequence of SEQ ID NO: 80 or a sequence differing in 1 or 2 amino acids therefrom;

(k) (i) a $V_H$ comprising complementarity-determining regions:

CDR-H1 comprising the amino acid sequence of SEQ ID NO: 82 or a sequence differing in 1 or 2 amino acids therefrom, CDR-H2 comprising the amino acid sequence of SEQ ID NO: 83 or a sequence differing in 1 or 2 amino acids therefrom, and CDR-H3 comprising the amino acid sequence of SEQ ID NO: 84 or a sequence differing in 1 or 2 amino acids therefrom; and (ii) a $V_K$ comprising complementarity-determining regions:

CDR-L1 comprising the amino acid sequence of SEQ ID NO: 86 or a sequence differing in 1 or 2 amino acids therefrom, CDR-L2 comprising the amino acid sequence of SEQ ID NO: 87 or a sequence differing in 1 or 2 amino acids therefrom, and CDR-L3 comprising the amino acid sequence of SEQ ID NO: 88 or a sequence differing in 1 or 2 amino acids therefrom;

(l) (i) a $V_H$ comprising complementarity-determining regions:

CDR-H1 comprising the amino acid sequence of SEQ ID NO: 90 or a sequence differing in 1 or 2 amino acids therefrom, CDR-H2 comprising the amino acid sequence of SEQ ID NO: 91 or a sequence differing in 1 or 2 amino acids therefrom, and CDR-H3 comprising the amino acid sequence of SEQ ID NO: 92 or a sequence differing in 1 or 2 amino acids therefrom; and (ii) a $V_K$ comprising complementarity-determining regions:

CDR-L1 comprising the amino acid sequence of SEQ ID NO: 94 or a sequence differing in 1 or 2 amino acids therefrom, CDR-L2 comprising the amino acid sequence of SEQ ID NO: 95 or a sequence differing in 1 or 2 amino acids therefrom, and CDR-L3 comprising the amino acid sequence of SEQ ID NO: 96 or a sequence differing in 1 or 2 amino acids therefrom;

(m) (i) a $V_H$ comprising complementarity-determining regions:

CDR-H1 comprising the amino acid sequence of SEQ ID NO: 98 or a sequence differing in 1 or 2 amino acids therefrom, CDR-H2 comprising the amino acid sequence of SEQ ID NO: 99 or a sequence differing in 1 or 2 amino acids therefrom, and CDR-H3 comprising the amino acid sequence of SEQ ID NO: 100 or a sequence differing in 1 or 2 amino acids therefrom; and (ii) a $V_K$ comprising complementarity-determining regions:

CDR-L1 comprising the amino acid sequence of SEQ ID NO: 102 or a sequence differing in 1 or 2 amino acids therefrom, CDR-L2 comprising the amino acid sequence of SEQ ID NO: 103 or a sequence differing in 1 or 2 amino acids therefrom, and CDR-L3 comprising the amino acid sequence of SEQ ID NO: 104 or a sequence differing in 1 or 2 amino acids therefrom;

(n) (i) a $V_H$ comprising complementarity-determining regions:

CDR-H1 comprising the amino acid sequence of SEQ ID NO: 106 or a sequence differing in 1 or 2 amino acids therefrom, CDR-H2 comprising the amino acid sequence of SEQ ID NO: 107 or a sequence differing in 1 or 2 amino acids therefrom, and CDR-H3 comprising the amino acid sequence of SEQ ID NO: 108 or a sequence differing in 1 or 2 amino acids therefrom; and (ii) a $V_K$ comprising complementarity-determining regions:

CDR-L1 comprising the amino acid sequence of SEQ ID NO: 110 or a sequence differing in 1 or 2 amino acids therefrom, CDR-L2 comprising the amino acid sequence of SEQ ID NO: 111 or a sequence differing in 1 or 2 amino acids therefrom, and CDR-L3 comprising the amino acid sequence of SEQ ID NO: 112 or a sequence differing in 1 or 2 amino acids therefrom;

(o) (i) a $V_H$ comprising complementarity-determining regions:

CDR-H1 comprising the amino acid sequence of SEQ ID NO: 114 or a sequence differing in 1 or 2 amino acids therefrom, CDR-H2 comprising the amino acid sequence of SEQ ID NO: 115 or a sequence differing in 1 or 2 amino acids therefrom, and CDR-H3 comprising the amino acid sequence of SEQ ID NO: 116 or a sequence differing in 1 or 2 amino acids therefrom; and (ii) a $V_K$ comprising complementarity-determining regions:

CDR-L1 comprising the amino acid sequence of SEQ ID NO: 118 or a sequence differing in 1 or 2 amino acids therefrom, CDR-L2 comprising the amino acid sequence of SEQ ID NO: 119 or a sequence differing in 1 or 2 amino acids therefrom, and CDR-L3 comprising the amino acid sequence of SEQ ID NO: 120 or a sequence differing in 1 or 2 amino acids therefrom;

(p) (i) a $V_H$ comprising complementarity-determining regions:

CDR-H1 comprising the amino acid sequence of SEQ ID NO: 122 or a sequence differing in 1 or 2 amino acids therefrom, CDR-H2 comprising the amino acid sequence of SEQ ID NO: 123 or a sequence differing in 1 or 2 amino acids therefrom, and CDR-H3 comprising the amino acid sequence of SEQ ID NO: 124 or a sequence differing in 1 or 2 amino acids therefrom; and (ii) a $V_K$ comprising complementarity-determining regions:

CDR-L1 comprising the amino acid sequence of SEQ ID NO: 126 or a sequence differing in 1 or 2 amino acids therefrom, CDR-L2 comprising the amino acid sequence of SEQ ID NO: 127 or a sequence differing in 1 or 2 amino acids therefrom, and CDR-L3 comprising the amino acid sequence of SEQ ID NO: 128 or a sequence differing in 1 or 2 amino acids therefrom; or (q) (i) a $V_H$ comprising complementarity-determining regions:

CDR-H1 comprising the amino acid sequence of SEQ ID NO: 130 or a sequence differing in 1 or 2 amino acids therefrom, CDR-H2 comprising the amino acid sequence of SEQ ID NO: 131 or a sequence differing in 1 or 2 amino acids therefrom, and CDR-H3 comprising the amino acid sequence of SEQ ID NO: 132 or a sequence differing in 1 or 2 amino acids therefrom; and (ii) a $V_K$ comprising complementarity-determining regions:

CDR-L1 comprising the amino acid sequence of SEQ ID NO: 134 or a sequence differing in 1 or 2 amino acids therefrom, CDR-L2 comprising the amino acid sequence of SEQ ID NO: 135 or a sequence differing in 1 or 2 amino acids therefrom, and CDR-L3 comprising the amino acid sequence of SEQ ID NO: 136 or a sequence differing in 1 or 2 amino acids therefrom.

In some embodiments, the CDR-H1, CDR-H2, CDR-H3, CDR-L1, CDR-L2, and CDR-L3 comprise amino acid sequences that collectively differ by no more than two amino acid residues from the sequences of:

(a) SEQ ID NO: 2, SEQ ID NO: 3, SEQ ID NO: 4, SEQ ID NO: 6, SEQ ID NO: 7, and SEQ ID NO: 8, respectively;

(b) SEQ ID NO: 10, SEQ ID NO: 11, SEQ ID NO: 12, SEQ ID NO: 14, SEQ ID NO: 15, and SEQ ID NO: 16, respectively;

(c) SEQ ID NO: 18, SEQ ID NO: 19, SEQ ID NO: 20, SEQ ID NO: 22, SEQ ID NO: 23, SEQ ID NO: 24, respectively;

(d) SEQ ID NO: 26, SEQ ID NO: 27, SEQ ID NO: 28, SEQ ID NO: 30, SEQ ID NO: 31, SEQ ID NO: 32, respectively;

(e) SEQ ID NO: 34, SEQ ID NO: 35, SEQ ID NO: 36, SEQ ID NO: 38, SEQ ID NO: 39, SEQ ID NO: 40, respectively;

(f) SEQ ID NO: 42, SEQ ID NO: 43, SEQ ID NO: 44, SEQ ID NO: 46, SEQ ID NO: 47, SEQ ID NO: 48, respectively;

(g) SEQ ID NO: 50, SEQ ID NO: 51, SEQ ID NO: 52, SEQ ID NO: 54, SEQ ID NO: 55, SEQ ID NO: 56, respectively;

(h) SEQ ID NO: 58, SEQ ID NO: 59, SEQ ID NO: 60, SEQ ID NO: 62, SEQ ID NO: 63, SEQ ID NO: 64, respectively;

(i) SEQ ID NO: 66, SEQ ID NO: 67, SEQ ID NO: 68, SEQ ID NO: 70, SEQ ID NO: 71, SEQ ID NO: 72, respectively;

(j) SEQ ID NO: 74, SEQ ID NO: 75, SEQ ID NO: 76, SEQ ID NO: 78, SEQ ID NO: 79, SEQ ID NO: 80, respectively;

(k) SEQ ID NO: 82, SEQ ID NO: 83, SEQ ID NO: 84, SEQ ID NO: 86, SEQ ID NO: 87, SEQ ID NO: 88, respectively;

(l) SEQ ID NO: 90, SEQ ID NO: 91, SEQ ID NO: 92, SEQ ID NO: 94, SEQ ID NO: 95, SEQ ID NO: 96, respectively;

(m) SEQ ID NO: 98, SEQ ID NO: 99, SEQ ID NO: 100, SEQ ID NO: 102, SEQ ID NO: 103, SEQ ID NO: 104, respectively;

(n) SEQ ID NO: 106, SEQ ID NO: 107, SEQ ID NO: 108, SEQ ID NO: 110, SEQ ID NO: 111, SEQ ID NO: 112, respectively;

(o) SEQ ID NO: 114, SEQ ID NO: 115, SEQ ID NO: 116, SEQ ID NO: 118, SEQ ID NO: 119, SEQ ID NO: 120, respectively;

(p) SEQ ID NO: 122, SEQ ID NO: 123, SEQ ID NO: 124, SEQ ID NO: 126, SEQ ID NO: 127, SEQ ID NO: 128, respectively; or (q) SEQ ID NO: 130, SEQ ID NO: 131, SEQ ID NO: 132, SEQ ID NO: 134, SEQ ID NO: 135, SEQ ID NO: 136, respectively.

In some embodiments, the antibody or antigen-binding fragment thereof comprises: (a) (i) a $V_H$ comprising complementarity-determining regions:

CDR-H1 comprising the amino acid sequence of SEQ ID NO: 2,

CDR-H2 comprising the amino acid sequence of SEQ ID NO: 3, and

CDR-H3 comprising the amino acid sequence of SEQ ID NO: 4; and (ii) a $V_K$ comprising complementarity-determining regions:

CDR-L1 comprising the amino acid sequence of SEQ ID NO: 6,

CDR-L2 comprising the amino acid sequence of SEQ ID NO: 7, and

CDR-L3 comprising the amino acid sequence of SEQ ID NO: 8;

(b) (i) a $V_H$ comprising complementarity-determining regions:

CDR-H1 comprising the amino acid sequence of SEQ ID NO: 10,

CDR-H2 comprising the amino acid sequence of SEQ ID NO: 11, and

CDR-H3 comprising the amino acid sequence of SEQ ID NO: 12; and (ii) a $V_K$ comprising complementarity-determining regions:

CDR-L1 comprising the amino acid sequence of SEQ ID NO: 14,

CDR-L2 comprising the amino acid sequence of SEQ ID NO: 15, and

CDR-L3 comprising the amino acid sequence of SEQ ID NO: 16;

(c) (i) a $V_H$ comprising complementarity-determining regions:

CDR-H1 comprising the amino acid sequence of SEQ ID NO: 18,

CDR-H2 comprising the amino acid sequence of SEQ ID NO: 19, and

CDR-H3 comprising the amino acid sequence of SEQ ID NO: 20; and (ii) a $V_K$ comprising complementarity-determining regions:

CDR-L1 comprising the amino acid sequence of SEQ ID NO: 22,

CDR-L2 comprising the amino acid sequence of SEQ ID NO: 23, and

CDR-L3 comprising the amino acid sequence of SEQ ID NO: 24;

(d) (i) a $V_H$ comprising complementarity-determining regions:
- CDR-H1 comprising the amino acid sequence of SEQ ID NO: 26,
- CDR-H2 comprising the amino acid sequence of SEQ ID NO: 27, and
- CDR-H3 comprising the amino acid sequence of SEQ ID NO: 28; and (ii) a $V_K$ comprising complementarity-determining regions:
- CDR-L1 comprising the amino acid sequence of SEQ ID NO: 30,
- CDR-L2 comprising the amino acid sequence of SEQ ID NO: 31, and
- CDR-L3 comprising the amino acid sequence of SEQ ID NO: 32;

(e) (i) a $V_H$ comprising complementarity-determining regions:
- CDR-H1 comprising the amino acid sequence of SEQ ID NO: 34,
- CDR-H2 comprising the amino acid sequence of SEQ ID NO: 35, and
- CDR-H3 comprising the amino acid sequence of SEQ ID NO: 36; and (ii) a $V_K$ comprising complementarity-determining regions:
- CDR-L1 comprising the amino acid sequence of SEQ ID NO: 38,
- CDR-L2 comprising the amino acid sequence of SEQ ID NO: 39, and
- CDR-L3 comprising the amino acid sequence of SEQ ID NO: 40;

(f) (i) a $V_H$ comprising complementarity-determining regions:
- CDR-H1 comprising the amino acid sequence of SEQ ID NO: 42,
- CDR-H2 comprising the amino acid sequence of SEQ ID NO: 43, and
- CDR-H3 comprising the amino acid sequence of SEQ ID NO: 44; and (ii) a $V_K$ comprising complementarity-determining regions:
- CDR-L1 comprising the amino acid sequence of SEQ ID NO: 46,
- CDR-L2 comprising the amino acid sequence of SEQ ID NO: 47, and
- CDR-L3 comprising the amino acid sequence of SEQ ID NO: 48;

(g) (i) a $V_H$ comprising complementarity-determining regions:
- CDR-H1 comprising the amino acid sequence of SEQ ID NO: 50,
- CDR-H2 comprising the amino acid sequence of SEQ ID NO: 51, and
- CDR-H3 comprising the amino acid sequence of SEQ ID NO: 52; and (ii) a $V_K$ comprising complementarity-determining regions:
- CDR-L1 comprising the amino acid sequence of SEQ ID NO: 54,
- CDR-L2 comprising the amino acid sequence of SEQ ID NO: 55, and
- CDR-L3 comprising the amino acid sequence of SEQ ID NO: 56;

(h) (i) a $V_H$ comprising complementarity-determining regions:
- CDR-H1 comprising the amino acid sequence of SEQ ID NO: 58,
- CDR-H2 comprising the amino acid sequence of SEQ ID NO: 59, and
- CDR-H3 comprising the amino acid sequence of SEQ ID NO: 60; and (ii) a $V_K$ comprising complementarity-determining regions:
- CDR-L1 comprising the amino acid sequence of SEQ ID NO: 62,
- CDR-L2 comprising the amino acid sequence of SEQ ID NO: 63, and
- CDR-L3 comprising the amino acid sequence of SEQ ID NO: 64;

(i) (i) a $V_H$ comprising complementarity-determining regions:
- CDR-H1 comprising the amino acid sequence of SEQ ID NO: 66,
- CDR-H2 comprising the amino acid sequence of SEQ ID NO: 67, and
- CDR-H3 comprising the amino acid sequence of SEQ ID NO: 68; and (ii) a $V_K$ comprising complementarity-determining regions:
- CDR-L1 comprising the amino acid sequence of SEQ ID NO: 70,
- CDR-L2 comprising the amino acid sequence of SEQ ID NO: 71, and
- CDR-L3 comprising the amino acid sequence of SEQ ID NO: 72;

(j) (i) a $V_H$ comprising complementarity-determining regions:
- CDR-H1 comprising the amino acid sequence of SEQ ID NO: 74,
- CDR-H2 comprising the amino acid sequence of SEQ ID NO: 75, and
- CDR-H3 comprising the amino acid sequence of SEQ ID NO: 76; and (ii) a $V_K$ comprising complementarity-determining regions:
- CDR-L1 comprising the amino acid sequence of SEQ ID NO: 78,
- CDR-L2 comprising the amino acid sequence of SEQ ID NO: 79, and
- CDR-L3 comprising the amino acid sequence of SEQ ID NO: 80;

(k) (i) a $V_H$ comprising complementarity-determining regions:
- CDR-H1 comprising the amino acid sequence of SEQ ID NO: 82,
- CDR-H2 comprising the amino acid sequence of SEQ ID NO: 83, and
- CDR-H3 comprising the amino acid sequence of SEQ ID NO: 84; and (ii) a $V_K$ comprising complementarity-determining regions:
- CDR-L1 comprising the amino acid sequence of SEQ ID NO: 86,
- CDR-L2 comprising the amino acid sequence of SEQ ID NO: 87, and
- CDR-L3 comprising the amino acid sequence of SEQ ID NO: 88;

(l) (i) a $V_H$ comprising complementarity-determining regions:
- CDR-H1 comprising the amino acid sequence of SEQ ID NO: 90, CDR-H2 comprising the amino acid sequence of SEQ ID NO: 91, and
CDR-H3 comprising the amino acid sequence of SEQ ID NO: 92; and
(ii) a $V_K$ comprising complementarity-determining regions:
CDR-L1 comprising the amino acid sequence of SEQ ID NO: 94,
CDR-L2 comprising the amino acid sequence of SEQ ID NO: 95, and
CDR-L3 comprising the amino acid sequence of SEQ ID NO: 96;
(m) (i) a $V_H$ comprising complementarity-determining regions:
CDR-H1 comprising the amino acid sequence of SEQ ID NO: 98,
CDR-H2 comprising the amino acid sequence of SEQ ID NO: 99, and
CDR-H3 comprising the amino acid sequence of SEQ ID NO: 100; and
(ii) a $V_K$ comprising complementarity-determining regions:
CDR-L1 comprising the amino acid sequence of SEQ ID NO: 102,
CDR-L2 comprising the amino acid sequence of SEQ ID NO: 103, and
CDR-L3 comprising the amino acid sequence of SEQ ID NO: 104;
(n) (i) a $V_H$ comprising complementarity-determining regions:
CDR-H1 comprising the amino acid sequence of SEQ ID NO: 106,
CDR-H2 comprising the amino acid sequence of SEQ ID NO: 107, and
CDR-H3 comprising the amino acid sequence of SEQ ID NO: 108; and
(ii) a $V_K$ comprising complementarity-determining regions:
CDR-L1 comprising the amino acid sequence of SEQ ID NO: 110,
CDR-L2 comprising the amino acid sequence of SEQ ID NO: 111, and
CDR-L3 comprising the amino acid sequence of SEQ ID NO: 112;
(o) (i) a $V_H$ comprising complementarity-determining regions:
CDR-H1 comprising the amino acid sequence of SEQ ID NO: 114,
CDR-H2 comprising the amino acid sequence of SEQ ID NO: 115, and
CDR-H3 comprising the amino acid sequence of SEQ ID NO: 116; and
(ii) a $V_K$ comprising complementarity-determining regions:
CDR-L1 comprising the amino acid sequence of SEQ ID NO: 118,
CDR-L2 comprising the amino acid sequence of SEQ ID NO: 119, and
CDR-L3 comprising the amino acid sequence of SEQ ID NO: 120;
(p) (i) a $V_H$ comprising complementarity-determining regions:
CDR-H1 comprising the amino acid sequence of SEQ ID NO: 122,
CDR-H2 comprising the amino acid sequence of SEQ ID NO: 123, and
CDR-H3 comprising the amino acid sequence of SEQ ID NO: 124; and
(ii) a $V_K$ comprising complementarity-determining regions:
CDR-L1 comprising the amino acid sequence of SEQ ID NO: 126,
CDR-L2 comprising the amino acid sequence of SEQ ID NO: 127, and
CDR-L3 comprising the amino acid sequence of SEQ ID NO: 128; or
(q) (i) a $V_H$ comprising complementarity-determining regions:
CDR-H1 comprising the amino acid sequence of SEQ ID NO: 130,
CDR-H2 comprising the amino acid sequence of SEQ ID NO: 131, and
CDR-H3 comprising the amino acid sequence of SEQ ID NO: 132; and
(ii) a $V_K$ comprising complementarity-determining regions:
CDR-L1 comprising the amino acid sequence of SEQ ID NO: 134,
CDR-L2 comprising the amino acid sequence of SEQ ID NO: 135, and
CDR-L3 comprising the amino acid sequence of SEQ ID NO: 136.

In some embodiments, the antibody or antigen-binding fragment thereof comprises:
(i) a $V_H$ comprising complementarity-determining regions:
CDR-H1 comprising the amino acid sequence of SEQ ID NO: 2;
CDR-H2 comprising the amino acid sequence of SEQ ID NO: 3; and
CDR-H3 comprising the amino acid sequence of SEQ ID NO: 4; and
(ii) a $V_K$ comprising complementarity-determining regions:
CDR-L1 comprising the amino acid sequence of SEQ ID NO: 6;
CDR-L2 comprising the amino acid sequence of SEQ ID NO: 7; and
CDR-L3 comprising the amino acid sequence of SEQ ID NO: 8.

In some embodiments, the $V_H$ comprises an amino acid sequence that is at least 85% identical to that of SEQ ID NO: 1; and the $V_K$ comprises an amino acid sequence that is at least 85% identical to that of SEQ ID NO: 5.

In some embodiments, the $V_H$ comprises the amino acid sequence of SEQ ID NO: 1; and the $V_K$ comprises the amino acid sequence of SEQ ID NO: 5.

In some embodiments, the antibody or antigen binding fragment thereof comprises:
(i) a $V_H$ comprising complementarity-determining regions:
CDR-H1 comprising the amino acid sequence of SEQ ID NO: 10;
CDR-H2 comprising the amino acid sequence of SEQ ID NO: 11; and
CDR-H3 comprising the amino acid sequence of SEQ ID NO: 12; and
(ii) a $V_K$ comprising complementarity-determining regions:
CDR-L1 comprising the amino acid sequence of SEQ ID NO: 14;
CDR-L2 comprising the amino acid sequence of SEQ ID NO: 15; and CDR-L3 comprising the amino acid sequence of SEQ ID NO: 16.

In some embodiments, the $V_H$ comprises an amino acid sequence that is at least 85% identical to that of SEQ ID NO: 9; and the $V_K$ comprises an amino acid sequence that is at least 85% identical to that of SEQ ID NO: 13.

In some embodiments, the $V_H$ comprises the amino acid sequence of SEQ ID NO: 9; and the $V_K$ comprises the amino acid sequence of SEQ ID NO: 13.

In some embodiments, the antibody or antigen binding fragment thereof comprises:
(i) a $V_H$ comprising complementarity-determining regions:
CDR-H1 comprising the amino acid sequence of SEQ ID NO: 18;
CDR-H2 comprising the amino acid sequence of SEQ ID NO: 19; and
CDR-H3 comprising the amino acid sequence of SEQ ID NO: 20; and
(ii) a $V_K$ comprising complementarity-determining regions:
CDR-L1 comprising the amino acid sequence of SEQ ID NO: 22;
CDR-L2 comprising the amino acid sequence of SEQ ID NO: 23; and
CDR-L3 comprising the amino acid sequence of SEQ ID NO: 24.

In some embodiments, the $V_H$ comprises an amino acid sequence that is at least 85% identical to that of SEQ ID NO: 17; and the $V_K$ comprises an amino acid sequence that is at least 85% identical to that of SEQ ID NO: 21.

In some embodiments, the $V_H$ comprises the amino acid sequence of SEQ ID NO: 17; and the $V_K$ comprises the amino acid sequence of SEQ ID NO: 21.

In some embodiments, the antibody or antigen binding fragment thereof comprises:
(i) a $V_H$ comprising complementarity-determining regions:
CDR-H1 comprising the amino acid sequence of SEQ ID NO: 34;
CDR-H2 comprising the amino acid sequence of SEQ ID NO: 35; and
CDR-H3 comprising the amino acid sequence of SEQ ID NO: 36; and
(ii) a $V_K$ comprising complementarity-determining regions:
CDR-L1 comprising the amino acid sequence of SEQ ID NO: 38;
CDR-L2 comprising the amino acid sequence of SEQ ID NO: 39; and
CDR-L3 comprising the amino acid sequence of SEQ ID NO: 40.

In some embodiments, the $V_H$ comprises an amino acid sequence that is at least 85% identical to that of SEQ ID NO: 33; and the $V_K$ comprises an amino acid sequence that is at least 85% identical to that of SEQ ID NO: 37.

In some embodiments, the $V_H$ comprises the amino acid sequence of SEQ ID NO: 33; and the $V_K$ comprises the amino acid sequence of SEQ ID NO: 37.

In some embodiments, the antibody or antigen binding fragment thereof comprises:
(i) a $V_H$ comprising complementarity-determining regions:
CDR-H1 comprising the amino acid sequence of SEQ ID NO: 98;
CDR-H2 comprising the amino acid sequence of SEQ ID NO: 99; and
CDR-H3 comprising the amino acid sequence of SEQ ID NO: 100; and
(ii) a $V_K$ comprising complementarity-determining regions:
CDR-L1 comprising the amino acid sequence of SEQ ID NO: 102;
CDR-L2 comprising the amino acid sequence of SEQ ID NO: 103; and
CDR-L3 comprising the amino acid sequence of SEQ ID NO: 104.

In some embodiments, the $V_H$ comprises an amino acid sequence that is at least 85% identical to that of SEQ ID NO: 97; and the $V_K$ comprises an amino acid sequence that is at least 85% identical to that of SEQ ID NO: 101.

In some embodiments, the $V_H$ comprises the amino acid sequence of SEQ ID NO: 97; and the $V_K$ comprises the amino acid sequence of SEQ ID NO: 101.

In some embodiments,
(a) the $V_H$ comprises an amino acid sequence at least 90%, 95%, 96%, 97%, 98%, or 99% identical to SEQ ID NO: 1 and the $V_K$ comprises an amino acid sequence at least 90%, 95%, 96%, 97%, 98%, or 99% identical to SEQ ID NO: 5;
(b) the $V_H$ comprises an amino acid sequence at least 90%, 95%, 96%, 97%, 98%, or 99% identical to SEQ ID NO: 9 and the $V_K$ comprises an amino acid sequence at least 90%, 95%, 96%, 97%, 98%, or 99% identical to SEQ ID NO: 13;
(c) the $V_H$ comprises an amino acid sequence at least 90%, 95%, 96%, 97%, 98%, or 99% identical to SEQ ID NO: 17 and the $V_K$ comprises an amino acid sequence at least 90%, 95%, 96%, 97%, 98%, or 99% identical to SEQ ID NO: 21;
(d) the $V_H$ comprises an amino acid sequence at least 90%, 95%, 96%, 97%, 98%, or 99% identical to SEQ ID NO: 25 and the $V_K$ comprises an amino acid sequence at least 90%, 95%, 96%, 97%, 98%, or 99% identical to SEQ ID NO: 29;
(e) the $V_H$ comprises an amino acid sequence at least 90%, 95%, 96%, 97%, 98%, or 99% identical to SEQ ID NO: 33 and the $V_K$ comprises an amino acid sequence at least 90%, 95%, 96%, 97%, 98%, or 99% identical to SEQ ID NO: 37;
(f) the $V_H$ comprises an amino acid sequence at least 90%, 95%, 96%, 97%, 98%, or 99% identical to SEQ ID NO: 41 and the $V_K$ comprises an amino acid sequence at least 90%, 95%, 96%, 97%, 98%, or 99% identical to SEQ ID NO: 45;
(g) the $V_H$ comprises an amino acid sequence at least 90%, 95%, 96%, 97%, 98%, or 99% identical to SEQ ID NO: 49 and the $V_K$ comprises an amino acid sequence at least 90%, 95%, 96%, 97%, 98%, or 99% identical to SEQ ID NO: 53;
(h) the $V_H$ comprises an amino acid sequence at least 90%, 95%, 96%, 97%, 98%, or 99% identical to SEQ ID NO: 57 and the $V_K$ comprises an amino acid sequence at least 90%, 95%, 96%, 97%, 98%, or 99% identical to SEQ ID NO: 61;
(i) the $V_H$ comprises an amino acid sequence at least 90%, 95%, 96%, 97%, 98%, or 99% identical to SEQ ID NO: 65 and the $V_K$ comprises an amino acid sequence at least 90%, 95%, 96%, 97%, 98%, or 99% identical to SEQ ID NO: 69;
(j) the $V_H$ comprises an amino acid sequence at least 90%, 95%, 96%, 97%, 98%, or 99% identical to SEQ ID NO:

73 and the $V_K$ comprises an amino acid sequence at least 90%, 95%, 96%, 97%, 98%, or 99% identical to SEQ ID NO: 77;

(k) the $V_H$ comprises an amino acid sequence at least 90%, 95%, 96%, 97%, 98%, or 99% identical to SEQ ID NO: 81 and the $V_K$ comprises an amino acid sequence at least 90%, 95%, 96%, 97%, 98%, or 99% identical to SEQ ID NO: 85;

(l) the $V_H$ comprises an amino acid sequence at least 90%, 95%, 96%, 97%, 98%, or 99% identical to SEQ ID NO: 89 and the $V_K$ comprises an amino acid sequence at least 90%, 95%, 96%, 97%, 98%, or 99% identical to SEQ ID NO: 93;

(m) the $V_H$ comprises an amino acid sequence at least 90%, 95%, 96%, 97%, 98%, or 99% identical to SEQ ID NO: 97 and the $V_K$ comprises an amino acid sequence at least 90%, 95%, 96%, 97%, 98%, or 99% identical to SEQ ID NO: 101;

(n) the $V_H$ comprises an amino acid sequence at least 90%, 95%, 96%, 97%, 98%, or 99% identical to SEQ ID NO: 105 and the $V_K$ comprises an amino acid sequence at least 90%, 95%, 96%, 97%, 98%, or 99% identical to SEQ ID NO: 109;

(o) the $V_H$ comprises an amino acid sequence at least 90%, 95%, 96%, 97%, 98%, or 99% identical to SEQ ID NO: 113 and the $V_K$ comprises an amino acid sequence at least 90%, 95%, 96%, 97%, 98%, or 99% identical to SEQ ID NO: 117;

(p) the $V_H$ comprises an amino acid sequence at least 90%, 95%, 96%, 97%, 98%, or 99% identical to SEQ ID NO: 121 and the $V_K$ comprises an amino acid sequence at least 90%, 95%, 96%, 97%, 98%, or 99% identical to SEQ ID NO: 125; or (q) the $V_H$ comprises an amino acid sequence at least 90%, 95%, 96%, 97%, 98%, or 99% identical to SEQ ID NO: 129 and the $V_K$ comprises an amino acid sequence at least 90%, 95%, 96%, 97%, 98%, or 99% identical to SEQ ID NO: 133.

In some embodiments, (a) the $V_H$ comprises an amino acid sequence of SEQ ID NO: 1 and the $V_K$ comprises an amino acid sequence of SEQ ID NO: 5;

(b) the $V_H$ comprises an amino acid sequence of SEQ ID NO: 9 and the $V_K$ comprises an amino acid sequence of SEQ ID NO: 13;

(c) the $V_H$ comprises an amino acid sequence of SEQ ID NO: 17 and the $V_K$ comprises an amino acid sequence of SEQ ID NO: 21;

(d) the $V_H$ comprises an amino acid sequence of SEQ ID NO: 25 and the $V_K$ comprises an amino acid sequence of SEQ ID NO: 29;

(e) the $V_H$ comprises an amino acid sequence of SEQ ID NO: 33 and the $V_K$ comprises an amino acid sequence of SEQ ID NO: 37;

(f) the $V_H$ comprises an amino acid sequence of SEQ ID NO: 41 and the $V_K$ comprises an amino acid sequence of SEQ ID NO: 45;

(g) the $V_H$ comprises an amino acid sequence of SEQ ID NO: 49 and the $V_K$ comprises an amino acid sequence of SEQ ID NO: 53;

(h) the $V_H$ comprises an amino acid sequence of SEQ ID NO: 57 and the $V_K$ comprises an amino acid sequence of SEQ ID NO: 61;

(i) the $V_H$ comprises an amino acid sequence of SEQ ID NO: 65 and the $V_K$ comprises an amino acid sequence of SEQ ID NO: 69;

(j) the $V_H$ comprises an amino acid sequence of SEQ ID NO: 73 and the $V_K$ comprises an amino acid sequence of SEQ ID NO: 77;

(k) the $V_H$ comprises an amino acid sequence of SEQ ID NO: 81 and the $V_K$ comprises an amino acid sequence of SEQ ID NO: 85;

(l) the $V_H$ comprises an amino acid sequence of SEQ ID NO: 89 and the $V_K$ comprises an amino acid sequence of SEQ ID NO: 93;

(m) the $V_H$ comprises an amino acid sequence of SEQ ID NO: 97 and the $V_K$ comprises an amino acid sequence of SEQ ID NO: 101;

(n) the $V_H$ comprises an amino acid sequence of SEQ ID NO: 105 and the $V_K$ comprises an amino acid sequence of SEQ ID NO: 109;

(o) the $V_H$ comprises an amino acid sequence of SEQ ID NO: 113 and the $V_K$ comprises an amino acid sequence of SEQ ID NO: 117;

(p) the $V_H$ comprises an amino acid sequence of SEQ ID NO: 121 and the $V_K$ comprises an amino acid sequence of SEQ ID NO: 125; or (q) the $V_H$ comprises an amino acid sequence of SEQ ID NO: 129 and the $V_K$ comprises an amino acid sequence of SEQ ID NO: 133.

In some embodiments, the antibody or antigen-binding fragment thereof is capable of binding to human Notch4 with a $K_D$ value of 10 nM or less.

In some embodiments, the antibody is a human antibody.

In some embodiments, the antibody or antigen binding fragment thereof comprises an antibody heavy chain constant region.

In some embodiments, the heavy chain constant region is a human IgG heavy chain constant region, e.g., a IgG4 heavy chain constant region.

Also provided are isolated nucleic acids encoding the heavy chain variable domain and/or light chain variable domain of an antibody disclosed herein or of antigen-binding fragment thereof, as well as expression vectors comprising such isolated nucleic acids and host cells comprising such isolated nucleic acids or expression vectors.

Also provided are compositions comprising a Notch4 antibody or Notch-binding fragment thereof as disclosed herein and a pharmaceutically acceptable carrier.

In one aspect, provided are methods of treating, ameliorating, or preventing airway inflammation in a subject, comprising the step of administering to the subject an effective amount of an Notch4 antibody or Notch4-binding fragment thereof as disclosed herein.

In some embodiments, the subject is a mammal, e.g., a human.

In some embodiments, the subject is diagnosed as having or at risk of having an airway inflammation-associated disorder, e.g., an airway inflammation-associated disorder is selected from the group consisting of asthma, chronic obstructive pulmonary disorder (COPD), cystic fibrosis (CF), or bronchopulmonary dysplasia (BPD).

In some embodiments, the step of administering comprises administration by a systemic route, e.g., a systemic route such as intravenous, intramuscular, or subcutaneous.

In one aspect, provided are methods of detecting the presence of Notch4, or a fragment thereof, in a sample, comprising contacting the sample with a Notch4 antibody or Notch4-binding fragment as disclosed herein and detecting the presence of a complex between the antibody or antigen-binding fragment and Notch4, wherein detection of the complex indicates the presence of Notch4.

BRIEF DESCRIPTION OF THE DRAWINGS

FIG. 4B shows the average percentages of Notch4-positive cells among Treg cells for the each mouse group. * denotes $p<0.05$,  denotes $p<0.01$, and * denotes $p<0.001$. FIG. 4C shows the average percentages of Notch4-positive cells among T effector (Teff) cells for the same treatment groups.

DETAILED DESCRIPTION OF CERTAIN EMBODIMENTS OF THE INVENTION

Figure 1:
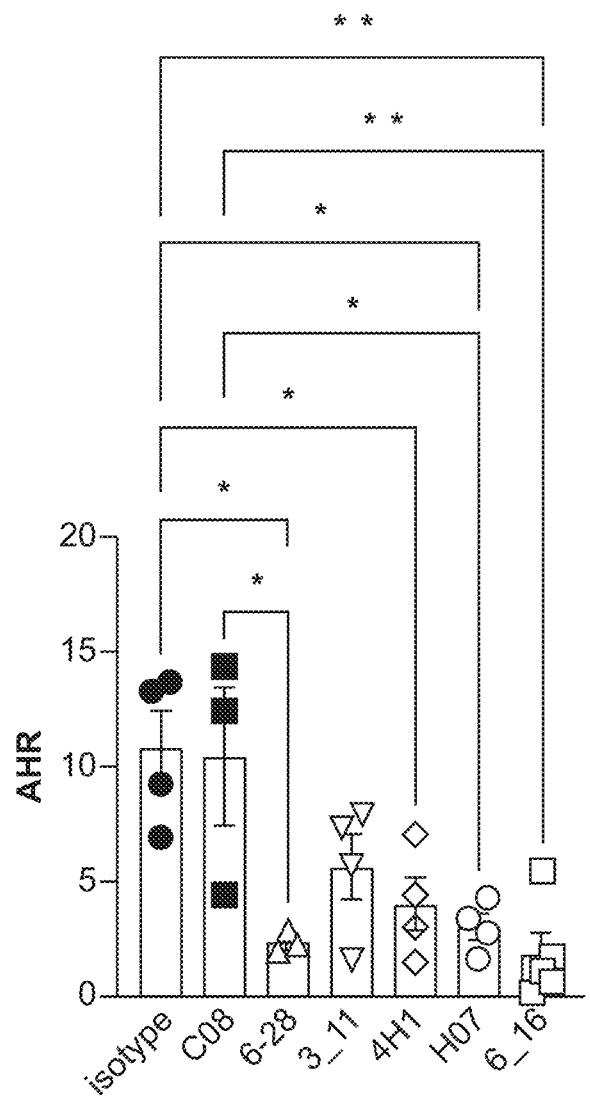
FIG. 1 shows the airway hyperresponsiveness from a methacholine challenge test in PBMC humanized mice sensitized to house dust mite allergen. The airway hyperresponsiveness ("AHR") was determined by the relative peak airway resistance calculated at the highest dose of methacholine tested (40 mg/mL) after treatment with novel Notch4-specific antibodies (C08-Lib3, iggrefmat 6-28, iggrefmat 3-11, H07-Lib3, and iggrefmat 6-16), 4H1 (a previously described Notch4 antibody) or an isotype control. * denotes $p<0.05$, and ** denotes $p<0.01$.

Notch4, whose amino acid sequence is shown below as SEQ ID NO: 137, is expressed on Treg cells, and its signaling in Treg cells drives allergic inflammation induced either by allergens or particulate matter pollutants (see, e.g., International Patent Publication No. WO 2019/178488). Disclosed herein are novel therapeutic Notch4 antibodies and compositions thereof, as well as related methods to treat, ameliorate, or prevent airway inflammation, including airway inflammation associated with certain disorders. Notch4 antibodies disclosed herein are fully human antibodies and are specific to Notch4 in that they do not substantially bind to other Notch proteins (such as Notch1, Notch2, and Notch3).

(Human Notch4 protein sequence)
SEQ ID NO: 137
MQPPSLLLLLLLLLLLCVSVVRPRGLLCGSFPEPCANGGTCLSLSLGQGT

CQCAPGELGETCQFPDPCQNAQLCQNGGSCQALLPAPLGLPSSPSPLTPS

FLCTCLPGFTGERCQAKLEDPCPPSFCSKRGRCHIQASGRPQCSCMPGWT

GEQCQLRDFCSANPCVNGGVCLATYPQIQCHCPPGFEGHACERDVNECFQ

DPGPCPKGTSCHNTLGSFQCLCPVGQEGPRCELRAGPCPPRGCSNGGTCQ

LMPEKDSTFHLCLCPPGFIGPDCEVNPDNCVSHQCQNGGTCQDGLDTYTC

LCPETWTGWDCSEDVDECETQGPPHCRNGGTCQNSAGSFHCVCVSGWGGT

SCEENLDDCIAATCAPGSTCIDRVGSFSCLCPPGRTGLLCHLEDMCLSQP

CHGDAQCSTNPLTGSTLCLCQPGYSGPTCHQDLDECLMAQQGPSPCEHGG

SCLNTPGSFNCLCPPGYTGSRCEADHNECLSQPCHPGSTCLDLLATFHCL

CPPGLEGQLCEVETNECASAPCLNHADCHDLLNGFQCICLPGFSGTRCEE

DIDECRSSPCANGGQCQDQPGAFHCKCLPGFEGPRCQTEVDECLSDPCPV

GASCLDLPGAFFCLCPSGFTGQLCEVPLCAPNLCQPKQICKDQKDKANCL

CPDGSPGCAPPEDNCTCHHGHCQRSSCVCDVGWTGPECEAELGGCISAPC

AHGGTCYPQPSGYNCTCPTGYTGPTCSEEMTACHSGPCLNGGSCNPSPGG

YYCTCPPSHTGPQCQTSTDYCVSAPCENGGTCVNRPGTFSCLCAMGFQGP

RCEGKLRPSCADSPCRNRATCQDSPQGPRCLCPTGYTGGSCQTLMDLCAQ

KPCPRNSHCLQTGPSFHCLCLQGWTGPLCNLPLSSCQKAALSQGIDVSSL

CHNGGLCVDSGPSYFCHCPPGFQGSLCQDHVNPCESRPCQNGATCMAQPS

GYLCQCAPGYDGQNCSKELDACQSQPCHNHGTCTPKGGFHCACPPGFVG

```
-continued
LRCEGDVDECLDQPCHPTGTAACHSLANAFYCQCLPGHTGQWCEVEIDPC

HSQPCFHGGTCEATAGSPLGFICHCPKGFEGPTCSHRAPSCGFHHCHHGG

LCLPSPKPGFPPRCACLSGYGGPDCLTPPAPKGCGPPSPCLYNGSCSETT

GLGGPGFRCSCPHSSPGPRCQKPGAKGCEGRSGDGACDAGCSGPGGNWDG

GDCSLGVPDPWKGCPSHSRCWLLFRDGQCHPQCDSEECLFDGYDCETPPA

CTPAYDQYCHDHFHNGHCEKGCNTAECGWDGGDCRPEDGDPEWGPSLALL

VVLSPPALDQQLFALARVLSLTLRVGLWVRKDRDGRDMVYPYPGARAEEK

LGGTRDPTYQERAAPQTQPLGKETDSLSAGFVVVMGVDLSRCGPDHPASR

CPWDPGLLLRFLAAMAAVGALEPLLPGPLLAVHPHAGTAPPANQLPWPVL

CSPVAGVILLALGALLVLQLIRRRRREHGALWLPPGFTRRPRTQSAPHRR

RPPLGEDSIGLKALKPKAEVDEDGVVMCSGPEEGEEVGQAEETGPPSTCQ

LWSLSGGCGALPQAAMLTPPQESEMEAPDLDTRGPDGVTPLMSAVCCGEV

QSGTFQGAWLGCPEPWEPLLDGGACPQAHTVGTGETPLHLAARFSRPTAA

RRLLEAGANPNQPDRAGRTPLHAAVAADAREVCQLLLRSRQTAVDARTED

GTTPLMLAARLAVEDLVEELIAAQADVGARDKWGKTALHWAAAVNNARAA

RSLLQAGADKDAQDNREQTPLFLAAREGAVEVAQLLLGLGAARELRDQAG

LAPADVAHQRNHWDLLTLLEGAGPPEARHKATPGREAGPFPRARTVSVSV

PPHGGGALPRCRTLSAGAGPRGGGACLQARTWSVDLAARGGGAYSHCRSL

SGVGAGGGPTPRGRRESAGMRGPRPNPAIMRGRYGVAAGRGGRVSTDDWP

CDWVALGACGSASNIPIPPPCLTPSPERGSPQLDCGPPALQEMPINQGGE

GKK
```

Definitions

As used herein, the terms "about," "approximately," and "comparable to," when used herein in reference to a value, refer to a value that is similar to the referenced value in the context of that referenced value. In general, those skilled in the art, familiar with the context, will appreciate the relevant degree of variance encompassed by "about," "approximately," and "comparable to" in that context. For example, in some embodiments, the terms "about," "approximately," and "comparable to" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

As used herein, the terms "antagonistic," "neutralizing" or "blocking," when used in reference to an antibody or antigen-binding fragment thereof, is intended to refer to an antibody or fragment thereof whose binding to its target results in inhibition of at least some of the biological activity of the target.

As used herein, "antibody" refers to a polypeptide whose amino acid sequence includes immunoglobulins and fragments thereof which specifically bind to a designated antigen, or fragments thereof. Antibodies in accordance with the present invention may be of any type (e.g., IgA, IgD, IgE, IgG, or IgM) or subtype (e.g., IgA1, IgA2, IgG1, IgG2, IgG3, or IgG4). Those of ordinary skill in the art will appreciate that a characteristic sequence or portion of an antibody may include amino acids found in one or more regions of an antibody (e.g., variable region, hypervariable region, constant region, heavy chain, light chain, and combinations thereof). Moreover, those of ordinary skill in the art will appreciate that a characteristic sequence or portion of an antibody may include one or more polypeptide chains, and may include sequence elements found in the same polypeptide chain or in different polypeptide chains.

An "antigen-binding fragment" of an antibody, or "antibody fragment" comprises a portion of an intact antibody, which portion is still capable of binding to a target antigen. In some embodiments, the antibody has a function in addition to that of antigen-binding, and an antigen-binding fragment retains that function. Typically, an antigen-binding fragment comprises the variable region of the antibody. Papain digestion of antibodies produce two identical antigen-binding fragments, called "Fab" fragments, and a residual "Fc" fragment, a designation reflecting the ability to crystallize readily. The Fab fragment consists of an entire light chain along with the variable region domain of the heavy chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and that is still capable of cross-linking antigen. Fab' fragments differ from Fab fragments by having a few additional residues at the carboxy terminus of the CHI domain, including one or more cysteines from the antibody hinge region. Fab'-SH designates an Fab' in which the cysteine residue(s) of the constant domains bear a free thiol group. F(ab')2 antibody fragments originally were produced as pairs of Fab' fragments having hinge cysteines between them. Other chemical couplings of antibody fragments are also known.

A "complementarity determining region" (abbreviated "CDR") is a region of hypervariability interspersed within regions that are more conserved, termed "framework regions" (abbreviated "FR"). In some embodiments, the sequences of the framework regions are identical to the framework regions in human germline sequences. In some embodiments, the sequences of the framework regions are modified with respect to the human germline sequence.

As used herein, the expression "control sequences" refers to DNA sequences necessary or advantageous for the expression of an operably linked coding sequence in a particular host organism. Control sequences that are typically suitable for prokaryotes, for example, include a promoter, optionally an operator sequence, and a ribosome binding site. Eukaryotic cells are known to utilize promoters, polyadenylation signals, and enhancers.

As used herein, antibody "effector functions" refer to those biological activities attributable to the Fc region (a native sequence Fc region or amino acid sequence variant Fc region) of an antibody, and which typically vary with the antibody isotype. Examples of antibody effector functions include, but are not limited to, C1q binding and complement dependent cytotoxicity, Fc receptor binding; antibody-dependent cell-mediated cytotoxicity (ADCC); phagocytosis, down regulation of cell surface receptors (e.g. B cell receptor), and B cell activation.

As used herein, the term "epitope" is an antigenic determinant that interacts with a specific antigen binding site in the variable region of an antibody molecule, known as the paratope, and which is comprised of the six complementarity-determining regions of the antibody. A single antigen may have more than one epitope. Epitopes may be conformational or linear. A conformational epitope is comprised of spatially juxtaposed amino acids from different segments of a linear polypeptide chain. A linear epitope is comprised of adjacent amino acid residues in a polypeptide chain.

An Fc fragment comprises the carboxy-terminal portions of both heavy chains held together by disulfides. The effector functions of antibodies are determined by sequences in the Fc region, the region which is also recognized by Fc receptors (FcR) found on certain types of cells.

As used herein, the term "humanized," when used in reference to an antibody, refers to a form of a non-human (e.g., murine) antibody that is chimeric. A "humanized antibody" contains minimal sequences derived from non-human immunoglobulin. Typically, humanized antibodies are human immunoglobulins (recipient or acceptor antibody) in which hypervariable region residues of the recipient are replaced by hypervariable region residues from a non-human species (donor antibody) such as mouse, rat, rabbit or nonhuman primate having a desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains, in which all or substantially all of the hypervariable loops correspond to those of a non-human immunoglobulin and all or substantially all of the framework regions are those of a human immunoglobulin sequence although the framework regions may include one or more amino acid substitutions that improve binding affinity. In some embodiments, no more than six amino acid substitutions in the heavy chain and no more than three amino acid substitutions are used in the light chain in the framework region. The humanized antibody optionally also will comprise at least a portion of an immunoglobulin constant region (Fc), typically that of a human immunoglobulin.

As used herein, an "isolated" nucleic acid molecule is a nucleic acid molecule that is identified and separated from at least one contaminant molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as they exists in natural cells.

As used herein, the term "monoclonal antibody" refers to an antibody obtained from a population of substantially homogeneous antibodies, e.g., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, monoclonal antibodies may be made by a hybridoma method, such as that first described by Kohler et al., Nature 256:495 (1975), or may be made by recombinant DNA methods (see, e.g., U.S. Pat. No. 4,816, 567). "Monoclonal antibodies" may also be isolated from phage antibody libraries, e.g., using techniques described in Clackson et al., Nature 352:624-628 (1991) and Marks et al., J. Mol. Biol. 222:581-597 (1991).

As used herein, a nucleic acid is "operably linked" when it is placed into a functional relationship with another nucleic acid sequence. For example, DNA for a presequence or secretory leader is "operably linked" to DNA for a polypeptide if it is expressed as a preprotein that participates in the secretion of the polypeptide; a promoter or enhancer is "operably linked" to a coding sequence if it affects the transcription of the sequence; or a ribosome binding site is "operably linked" to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking may be accomplished, e.g., by ligation at convenient restriction sites. If such sites do not exist, synthetic oligonucleotide adaptors or linkers may be used in accordance with conventional practice.

As used herein, "polypeptide" refers to a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides can include one or more "non-natural" amino acids or other entities that nonetheless are capable of integrating into a polypeptide chain. In some embodiments, a polypeptide may be glycosylated, e.g., a polypeptide may contain one or more covalently linked sugar moieties. In some embodiments, a single "polypeptide" (e.g., an antibody polypeptide) may comprise two or more individual polypeptide chains, which may in some cases be linked to one another, for example by one or more disulfide bonds or other means.

As used herein, the phrase "reference level" generally refers to a level considered "normal" for comparison purposes, e.g., a level of an appropriate control. For example, in the context of airway inflammation, a "reference level" may refer to the level of airway resistance in a subject who has a condition associated with airway inflammation and who is not receiving a therapeutic agent of interest, or in a subject receiving a treatment (e.g., the current standard of care) other than the therapeutic agent of interest. A reference level may be determined contemporaneously or may be predetermined, e.g., known or deduced from past observations.

As used herein, the phrases "therapeutically effective amount" and "effective amount" are used interchangeably and refer to an amount effective, at dosages and for periods of time necessary, to achieve a desired therapeutic result. A therapeutically effective amount may vary according to factors such as the type of disease (e.g., an airway inflammation-associated disorder such as asthma), disease state, age, sex, and/or weight of the individual, and the ability of a Notch4 antibody (or pharmaceutical composition thereof) to elicit a desired response in the individual. An effective amount may also be an amount for which any toxic or detrimental effects of the or pharmaceutical composition thereof are outweighed by therapeutically beneficial effects.

As used herein, to "treat" a condition or "treatment" of the condition (e.g., the conditions described herein such as an airway inflammation-associated disorder such as asthma) is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

Antibodies and Antigen Binding Fragments Thereof

In one aspect, provided are antibodies and antigen binding fragments thereof that are capable of binding to Notch4. In some embodiments, the antibodies or antigen binding fragments are monoclonal antibodies or antigen binding fragments thereof. In some embodiments, the antibodies or antigen binding fragments are human antibodies or antigen binding fragments thereof, e.g., human monoclonal antibodies or antigen binding fragments thereof.

In some embodiments, provided are antigen-binding fragments. For example, the fragments may be, e.g., an scFv, an Fab, an scFab (single-chain Fab).

As used herein, the term "scFv" is used in accordance with its common usage in the art to refer to a single chain in which the $V_H$ domain and the $V_L$ or $V_K$ domain from an antibody are joined, typically via a linker.

As used herein, the term "Fab fragment" is used in accordance with its common usage in the art. Fab fragments typically comprise an entire light chain ($V_L$ or $V_K$ and $C_L1$ domains), the variable region domain of the heavy chain ($V_H$), and the first constant domain of one heavy chain ($C_H1$).

In some embodiments, provided are immunoconjugates comprising an antibody or antigen-binding fragment as disclosed herein that are labeled and/or conjugated to a cytotoxic agent such as a toxin or a radioactive isotope.

Exemplary Antibodies

In some embodiments, provided antibodies or antigen-binding fragments comprise a heavy chain variable domain and a light chain variable domain, wherein the heavy chain variable domain comprises a CDR-H1, CDR-H2, and CDR-H3, and the light chain variable domain comprises a CDR-L1, CDR-L2, and CDR-L3, wherein the CDR-H1, CDR-H2, CDR-H3, CDR-L1, CDR-L2, and CDR-L3, are those of an antibody described in Table 1 below. In some embodiments, provided are antibodies or antigen-binding fragments that are variants of the antibodies shown in Table 1, in that such antibodies or antigen-binding fragments have CDR sequences that differ by no more than two amino acid residues (e.g., two or one amino acid residue(s)) per CDR from the CDR sequences of an antibody described in Table 1. In some embodiments, provided are antibodies or antigen-binding fragments that are variants of the antibodies shown in Table 1, in that such antibodies or antigen-binding fragments have a set of six CDRs whose sequences collectively differ by no more than two amino acid residues (e.g., two or one amino acid residues) from the CDRs of an antibody described in Table 1.

In some embodiments, provided antibodies or antigen-binding fragments comprise a heavy chain variable domain and a light chain variable domain which comprise heavy chain variable domain and light chain variable sequences of an antibody described in Table 1. In some embodiments, provided are antibodies or antigen-binding fragments that are variants of the antibodies shown in Table 1, in that such antibodies or antigen-binding fragments have (1) a heavy chain domain comprising an amino acid sequence that is at least 85%, at least 87.5%, at least 90%, at least 91%, at least 92%, at least 93%, at least 94%, at least 95%, at least 96%, at least 97%, at least 98%, or at least 99% identical to the amino acid sequence of the heavy chain variable domain of an antibody described in Table 1; and (2) a light chain domain comprising an amino acid sequence that is at least 85%, at least 87.5%, at least 90%, at least 91%, at least 92%, at least 93%, at least 94%, at least 95%, at least 96%, at least 97%, at least 98%, or at least 99% identical to the amino acid sequence of a light chain variable domain of the same antibody described in Table 1.

TABLE 1

Exemplary heavy chain variable domain, light chain variable domain, and complementarity-determining region sequences of Notch4 antibodies

| Notch-4 antibody | Heavy chain variable domain (VH) | Light chain variable domain (VL) |
|---|---|---|
| iggrefmat 6-16 | EVQLVESGGGLVQPGRSLRLSCAAS EFSFSRFDMHWVRQAPGKGLEWVSA ISSSGSYKDYADSVEGRFTISRDNA KNSLYLQMNSLRAEDTAVYYCAREA YGDYGKPFDYWGQGTLVTVSS (SEQ ID NO: 1) CDR-H1: EFSFSRED (SEQ ID NO: 2) CDR-H2: ISSSGSYK (SEQ ID NO: 3) CDR-H3: AREAYGDYGKPFDY (SEQ ID NO: 4) | DIQMTQSPSSLSASVGDRVTITCRAS QSISRNLAWYQQKPGKAPKLLIYAGS TLQRGVPSRFSGSGSGTDFTLTISSL QPEDVATYYCLQANMYPLTFGGGTKV EIK (SEQ ID NO: 5) CDR-L1: QSISRN (SEQ ID NO: 6) CDR-L2: AGSTLQR (SEQ ID NO: 7) CDR-L3: LQANMYPLT (SEQ ID NO: 8) |
| C08-Lib3-P11 | EVQLVESGGGLVQPGGSLRLSCAAS GLPFSSYGMSWVRQAPGKGLELVAS IGTSGTRTYYPDSVKGRFTISRDNA KNSLYLQMNSLRAEDTAVYYCARLG EGSGWSYFDYWGQGTLVTVSS (SEQ ID NO: 9) CDR-H1: GLPFSSYG (SEQ ID NO: 10) CDR-H2: IGTSGTRT (SEQ ID NO: 11) CDR-H3: ARLGEGSGWSYFDY (SEQ ID NO: 12) | DIVMTQSPLSLPVTPGEPASISCRSS QSLLHSTGYNYLHWYLQKPGQSPQLL IYSGSYRASGVPDRFSGSGSGTDFTL KISRVEAEDVGVYYCQQGYSTPHTFG GGTKVEIK (SEQ ID NO: 13) CDR-L1: QSLLHSTGYNY (SEQ ID NO: 14) CDR-L2: SGSYRAS (SEQ ID NO: 15) CDR-L3: QQGYSTPHT (SEQ ID NO: 16) |

TABLE 1-continued

Exemplary heavy chain variable domain, light chain variable domain, and complementarity-determining region sequences of Notch4 antibodies

| Notch-4 antibody | Heavy chain variable domain (VH) | Light chain variable domain (VL) |
|---|---|---|
| iggrefmat 3-11 (same as H03-Lib6-P12) | EVQLVQSGAEVKKPGASVKVSCKAS GYTFATYPISWVRQAPGQGLEWMGG MNPTTGDTIYAQKLQGRGTMTTDPS TSTAYMELRSLRSDDTAVYYCARGD RAWFDPWGQGTLVTVSS (SEQ ID NO: 17)<br>CDR-H1: GYTFATYP (SEQ ID NO: 18)<br>CDR-H2: MNPTTGDT (SEQ ID NO: 19)<br>CDR-H3: ARGDRAWFDP (SEQ ID NO: 20) | ESALTQPASVSGSPGQSITISCTGTG SNIGAGYGVSWYQQHPGKAPKLMIYA NINRPPGVSNRFSGSKSGNTASLTIS GLQAEDEADYYCSSYTSSSWMFGGGT KLTVL (SEQ ID NO: 21)<br>CDR-L1: GSNIGAGYG (SEQ ID NO: 22)<br>CDR-L2: ANINRPP (SEQ ID NO: 23)<br>CDR-L3: SSYTSSSWM (SEQ ID NO: 24) |
| iggrefmat 2-12 (same as E08-Lib3-P11) | EVQLVESGGGLVQPGGSLRLSCAAS GFSFGTYSMSWVRQAPGKGLELVAS IDTAGTPYYPDSVKGRFTISRDNAK NSLYLQMNSLRAEDTAVYYCARSYS GYDPYDAFDIWGQGTMVTVSS (SEQ ID NO: 25)<br>CDR-H1: GFSFGTYS (SEQ ID NO: 26)<br>CDR-H2: IDTAGTP (SEQ ID NO: 27)<br>CDR-H3: ARSYSGYDPYDAFDI (SEQ ID NO: 28) | DIVMTQSPLSLPVTPGEPASISCRSS RSLVHGSGDNYLHWYLQKPGQSPQLL IYDASNRFSGVPDRESGSGSGTDFTL KISRVEAEDVGVYYCAQTLQIPLTFG GGTKVEIK (SEQ ID NO: 29)<br>CDR-L1: RSLVHGSGDNY (SEQ ID NO: 30)<br>CDR-L2: DASNRFS (SEQ ID NO: 31)<br>CDR-L3: AQTLQIPLT (SEQ ID NO: 32) |
| H07-Lib3-P11 | EVQLVESGGGLVQPGGSLRLSCAAS GLPFSSYAMSWVRQAPGKGLELVAS IGTAGDAYYPDSVKGRFTISRDNAK NSLYLQMNSLRAEDTAVYYCARVGP FWQGFAFDIWGQGTMVTVSS (SEQ ID NO: 33)<br>CDR-H1: GLPFSSYA (SEQ ID NO: 34)<br>CDR-H2: IGTAGDA (SEQ ID NO: 35)<br>CDR-H3: ARVGPFWQGFAFDI (SEQ ID NO: 36) | DIVMTQSPLSLPVTPGEPASISCRSS QSLLHSSGHNYLHWYLQKPGQSPQLL IYMTYNRASGVPDRFSGSGSGTDFTL KISRVEAEDVGVYYCLQTTHWPHTFG GGTKVEIK (SEQ ID NO: 37)<br>CDR-L1: QSLLHSSGHNY (SEQ ID NO: 38)<br>CDR-L2: MTYNRAS (SEQ ID NO: 39)<br>CDR-L3: LQTTHWPHT (SEQ ID NO: 40) |
| iggrefmat 1-12 (same as C02-Lib1_P11) | QVQLVQSGAEVKKPGASVKVSCKVS GYPFSNYAIHWVRQAPGKGLEWMGG ISPYTGKTIYAQKFQGRVTMTEDTS TDTAYMELSSLKSEDTAVYYCAFSR YYYDSSGYHGDAFDIWGQGTMVTVS S (SEQ ID NO: 41)<br>CDR-H1: GYPFSNYA (SEQ ID NO: 42)<br>CDR-H2: ISPYTGKT (SEQ ID NO: 43)<br>CDR-H3: AFSRYYYDSSGYHGDAF DI( SEQ ID NO: 44) | DIQMTQSPSSVSASVGDRVTITCRAS QGISNHLAWYQQKPGKAPKLLIYDAS NRATGVPSRFSGSGSGTDFTLTISSL QPEDFANYYCQQSFTIPSFGGGTKVE IK (SEQ ID NO: 45)<br>CDR-L1: QGISNH (SEQ ID NO: 46)<br>CDR-L2: DASNRAT (SEQ ID NO: 47)<br>CDR-L3: QQSFTIPS (SEQ ID NO: 48) |
| iggrefmat 2-16 (same as C07-Lib3-P11) | QVQLVESGGGLVQPGGSLRLSCAAS GLTFSGSAMSWVRQAPGKGLELVAS ITGSGTRTYYPDSVKGRFTISRDNA KNSLYLQMNSLRAEDTAVYYCARGL HAFDIWGQGTMVTVSS (SEQ ID NO: 49)<br>CDR-H1: GLTFSGSA (SEQ ID NO: 50)<br>CDR-H2: ITGSGTRT (SEQ ID NO: 51)<br>CDR-H3: ARGLHAFDI (SEQ ID NO: 52) | DIVMTQSPLSLPVTPGEPASISCRSS QSLLSSYGYHNLHWYLQKPGQSPQLL IYMGYNRASGVPDRFSGSGSGTDFTL KISRVEAEDVGVYYCMQGMHLPITFG GGTKVEIK (SEQ ID NO: 53)<br>CDR-L1: QSLLSSYGYHN (SEQ ID NO: 54)<br>CDR-L2: MGYNRAS (SEQ ID NO: 55)<br>CDR-L3: MQGMHLPIT (SEQ ID NO: 56) |

TABLE 1-continued

Exemplary heavy chain variable domain, light chain variable domain, and complementarity-determining region sequences of Notch4 antibodies

| Notch-4 antibody | Heavy chain variable domain (VH) | Light chain variable domain (VL) |
|---|---|---|
| iggrefmat 1-34 | QVQLVQSGAEVKKPGASVKVSCKVS<u>GYTLTKSS</u>IHWVRQAPGKGLEWMGG<u>INPSAGTR</u>IYAQKFQGRVTMTEDTSTDTAYMELSSLKSEDTAVYYC<u>VRGSNPNV</u>WGKGTTVTVSS (SEQ ID NO: 57)<br>CDR-H1: GYTLTKSS (SEQ ID NO: 58)<br>CDR-H2: INPSAGTR (SEQ ID NO: 59)<br>CDR-H3: VRGSNPNV (SEQ ID NO: 60) | DIQMTQSPSSVSASVGDRVTITCRAS<u>QTIGNY</u>LAWYQQKPGKAPKLLIY<u>KASTLAS</u>GVPSRESGSGSGTDFTLTISSLQPEDFANYYC<u>QQYNFYPRT</u>FGGGTKVEIK (SEQ ID NO: 61)<br>CDR-L1: QTIGNY (SEQ ID NO: 62)<br>CDR-L2: KASTLAS (SEQ ID NO: 63)<br>CDR-L3: QQYNFYPRT (SEQ ID NO: 64) |
| G04-Lib6-P12 | EVQLVQSGAEVKKPGASVKVSCKAS<u>GYSFTKSG</u>IHWVRQAPGQGLEWMGW<u>INPRTGNI</u>NYAQKLQGRGTMTTDPSTSTAYMELRSLRSDDTAVYYC<u>ARTHLGSSSSPPGYYYGMDV</u>WGQGTTVTVSS (SEQ ID NO: 65)<br>CDR-H1: GYSFTKSG (SEQ ID NO: 66)<br>CDR-H2: INPRTGNI (SEQ ID NO: 67)<br>CDR-H3: ARTHLGSSSSPPGYYYGMDV (SEQ ID NO: 68) | ESALTQPASVSGSPGQSITISCTGTN<u>IGAKAVS</u>WYQQHPGKAPKLMIY<u>AENKRPS</u>GVSNRFSGSKSGNTASLTISGLQAEDEADYYC<u>QAWDNRAIL</u>FGGGTKLTVL (SEQ ID NO: 69)<br>CDR-L1: NIGAKA (SEQ ID NO: 70)<br>CDR-L2: AENKRPS (SEQ ID NO: 71)<br>CDR-L3: QAWDNRAIL (SEQ ID NO: 72) |
| iggrefmat 3-13 (same as C11-Lib4-P11) | EVQLVQSGAEVKKPGASVKVSCKAS<u>GFPFSTSA</u>ISWVRQAPGQGLEWMGW<u>MDPATGQT</u>NYAQKLQGRGTMTTDPSTSTAYMELRSLRSDDTAVYYC<u>ARALRYCSGGRCQGFHGMDV</u>WGQGTTVTVSS (SEQ ID NO: 73)<br>CDR-H1: GFPFSTSA (SEQ ID NO: 74)<br>CDR-H2: MDPATGQT (SEQ ID NO: 75)<br>CDR-H3: ARALRYCSGGRCQGFHGMDV (SEQ ID NO: 76) | ESALTQPASVSGSPGQSITISCTGTN<u>IAAKSVS</u>WYQQHPGKAPKLMIY<u>ANINRPP</u>GVSNRFSGSKSGNTASLTISGLQAEDEADYYC<u>SSYTSSSWM</u>FGGGTKLTVL (SEQ ID NO: 77)<br>CDR-L1: NIAAKS (SEQ ID NO: 78)<br>CDR-L2: ANINRPP (SEQ ID NO: 79)<br>CDR-L3: SSYTSSSWM (SEQ ID NO: 80) |
| iggrefmat 3-4 (same as D11-Lib4-P11) | EVQLVQSGAEVKKPGASVKVSCKAS<u>GYTFSDHY</u>ISWVRQAPGQGLEWMGW<u>MNPTSGHT</u>NYAQKLQGRGTMTTDPSTSTAYMELRSLRSDDTAVYYC<u>ARVSGRWLPAVDGHYYYYGMDV</u>WGQGTTVTVSS (SEQ ID NO: 81)<br>CDR-H1: GYTFSDHY (SEQ ID NO: 82)<br>CDR-H2: MNPTSGHT (SEQ ID NO: 83)<br>CDR-H3: ARVSGRWLPAVDGHYYYYGMDV (SEQ ID NO: 84) | ESALTQPASVSGSPGQSITISCTGTG<u>SNIGAGYG</u>VSWYQQHPGKAPKLMIY<u>ANINRPP</u>GVSNRFSGSKSGNTASLTISGLQAEDEADYYC<u>SSYTSSSWM</u>FGGGTKLTVL (SEQ ID NO: 85)<br>CDR-L1: GSNIGAGYG (SEQ ID NO: 86)<br>CDR-L2: ANINRPP (SEQ ID NO: 87)<br>CDR-L3: SSYTSSSWM (SEQ ID NO: 88) |
| C04-Lib1-P11 | QVQLVQSGAEVKKPGASVKVSCKVS<u>GYAFTTYN</u>IHWVRQAPGKGLEWMGG<u>INPSGSTS</u>IYAQKFQGRVTMTEDTSTDTAYMELSSLKSEDTAVYYC<u>ARGPVDV</u>WGQGTTVTVSS (SEQ ID NO: 89)<br>CDR-H1: GYAFTTYN (SEQ ID NO: 90)<br>CDR-H2: INPSGSTS (SEQ ID NO: 91)<br>CDR-H3: ARGIPVDV (SEQ ID NO: 92) | DIQMTQSPSSVSASVGDRVTITCRAS<u>RDIDNY</u>LAWYQQKPGKAPKLLIY<u>GKDQRAS</u>GVPSRFSGSGSGTDFTLTISSLQPEDFANYYC<u>QQYRTYPWT</u>FGGGTKVEIK (SEQ ID NO: 93)<br>CDR-L1: RDIDNY (SEQ ID NO: 94)<br>CDR-L2: GKDORAS (SEQ ID NO: 95)<br>CDR-L3: QQYRTYPWT (SEQ ID NO: 96) |

TABLE 1-continued

Exemplary heavy chain variable domain, light chain variable domain, and complementarity-determining region sequences of Notch4 antibodies

| Notch-4 antibody | Heavy chain variable domain (VH) | Light chain variable domain (VL) |
|---|---|---|
| iggrefmat 6-28 (same as E03-Lib8H1N4) | EVQLVESGGGLVQPGRSLRLSCAAS GFSFSDYHMHWVRQAPGKGLEWVGA ISGSAYTTDYADSVEGRFTISRDNA KNSLYLQMNSLRAEDTAVYYCARDD YNKDGFDPWGQGTLVTVSS (SEQ ID NO: 97)<br>CDR-H1: GFSFSDYH (SEQ ID NO: 98)<br>CDR-H2: ISGSAYTT (SEQ ID NO: 99)<br>CDR-H3: ARDDYNKDGFDP (SEQ ID NO: 100) | DIQMTQSPSSLSASVGDRVTITCRAS QSIYSYLAWYQQKPGKAPKLLIYDAS RLQSGVPSRFSGSGSGTDFTLTISSL QPEDVATYYCQQGYRSPITFGGGTKV EIK (SEQ ID NO: 101)<br>CDR-L1: QSIYSY (SEQ ID NO: 102)<br>CDR-L2: DASRLQS (SEQ ID NO: 103)<br>CDR-L3: QQGYRSPIT (SEQ ID NO: 104) |
| B07-Lib3-P11 | EVQLVESGGGLVQPGGSLRLSCAAS GFTLDNYVMSWVRQAPGKGLELVAS ISGSSADTYYPDSVKGRFTISRDNA KNSLYLQMNSLRAEDTAVYYCAKGI AAGYGMDVWGQGTTVTVSS (SEQ ID NO: 105)<br>CDR-H1: GFTLDNYV (SEQ ID NO: 106)<br>CDR-H2: ISGSSADT (SEQ ID NO: 107)<br>CDR-H3: AKGIAAGYGMDV (SEQ ID NO: 108) | DIVMTQSPLSLPVTPGEPASISCRSS QSLLHSSGYTYLHWYLQKPGQSPQLL IYATSYRAPGVPDRFSGSGSGTDFTL KISRVEAEDVGVYYCMQATHPYTFGG GTKVEIK (SEQ ID NO: 109)<br>CDR-L1: QSLLHSSGYTY (SEQ ID NO: 110)<br>CDR-L2: ATSYRAP (SEQ ID NO: 111)<br>CDR-L3: MQATHPYT (SEQ ID NO: 112) |
| C03-Lib1-P11 | QVQLVQSGAEVKKPGASVKVSCKVS GYTFTDLPIHWVRQAPGKGLEWMGG INPHSGDAIYAQKFQGRVTMTEDTS TDTAYMELSSLKSEDTAVYYCTTVI AVAGSNDSRPCGRSYLCVLDYWGQG TLVTVSS (SEQ ID NO: 113)<br>CDR-H1: GYTFTDLP (SEQ ID NO: 114)<br>CDR-H2: INPHSGDA (SEQ ID NO: 115)<br>CDR-H3: TTVIAVAGSNDSRPCGR SYLCVLDY (SEQ ID NO: 116) | DIQMTQSPSSVSASVGDRVTITCNAS QGIGHSLAWYQQKPGKAPKLLIYGAT SRATGVPSRFSGSGSGTDFTLTISSL QPEDFANYYCLQDYIYPFTFGGGTKV EIK (SEQ ID NO: 117)<br>CDR-L1: QGIGHS (SEQ ID NO: 118)<br>CDR-L2: GATSRAT (SEQ ID NO: 119)<br>CDR-L3: LQDYIYPFT (SEQ ID NO: 120) |
| iggrefmat 1-29 (same as C01-Lib1-P11) | QVQLVQSGAEVKKPGASVKVSCKVS RGTFSTYAIHWVRQAPGKGLEWMGG INAATGYTIYAQKFQGRVTMTEDTS TDTAYMELSSLKSEDTAVYYCVRSV GSIEYWGQGTLVTVSS (SEQ ID NO: 121)<br>CDR-H1: RGTFSTYA (SEQ ID NO: 122)<br>CDR-H2: INAATGYT (SEQ ID NO: 123)<br>CDR-H3: VRSVGSIEY (SEQ ID NO: 124) | DIQMTQSPSSVSASVGDRVTITCRAS QGISNHLAWYQQKPGKAPKLLIYGAS SRQSGVPSRFSGSGSGTDFTLTISSL QPEDFANYYCLHDRYPYTFGGGTKVE IK (SEQ ID NO: 125)<br>CDR-L1: QGISNH (SEQ ID NO: 126)<br>CDR-L2: GASSRQS (SEQ ID NO: 127)<br>CDR-L3: LHDRYPYT (SEQ ID NO: 128) |
| G05-Lib3-P11 | EVQLVESGGGLVQPGGSLRLSCAAS GFTFSDYSMSWVRQAPGKGLELVAS ISESGHDTYYPDSVKGRFTISRDNA KNSLYLQMNSLRAEDTAVYYCARGI AVAGTRAFDIWGQGTMVTVSS (SEQ ID NO: 129)<br>CDR-H1: GFTFSDYS (SEQ ID NO: 130)<br>CDR-H2: ISESGHDT (SEQ ID NO: 131)<br>CDR-H3: ARGIAVAGTRAFDI (SEQ ID NO: 132) | DIVMTQSPLSLPVTPGEPASISCRSS QSLLYSTGYNYLHWYLQKPGQSPQLL IYMGSYRASGVPDRESGSGSGTDETL KISRVEAEDVGVYYCMQALPTPPITF GGGTKVEIK (SEQ ID NO: 133)<br>CDR-L1: QSLLYSTGYNY (SEQ ID NO: 134)<br>CDR-L2: MGSYRAS (SEQ ID NO: 135)<br>CDR-L3: MQALPTPPIT (SEQ ID NO: 136) |

Antibody Constant Regions

In some embodiments, provided Notch4 antibodies or Notch4-binding fragments thereof comprise one or more constant regions such as a heavy chain constant region and/or a light chain constant region.

In some embodiments, a provided Notch4 antibody or Notch4-binding fragment thereof comprises an IgG4 heavy chain constant region, e.g., an IgG4 heavy chain constant region having at least 93%, at least 94%, at least 95%, at least 96%, at least 97%, at least 98%, at least 99%, or identical to that SEQ ID NO:138. In some embodiments, a provided Notch4 antibody or Notch4-binding fragment thereof comprises an Igκ light chain constant region, e.g., an Igκ light chain constant region having at least 93%, at least 94%, at least 95%, at least 96%, at least 97%, at least 98%, at least 99%, or identical to that SEQ ID NO:142.

```
human IgG4 heavy chain constant region sequence
                                           SEQ ID NO: 138
ASTKGPSVFPLAPCSRSTSESTAALGCLVKDYFPEPVTVSWNSGALTSGVHTFPAVLQSSGL

YSLSSVVTVPSSSLGTKTYTCNVDHKPSNTKVDKRVESKYGPPCPSCPAPEFLGGPSVFLFP

PKPKDTLMISRTPEVTCVVVDVSQEDPEVQFNWYVDGVEVHNAKTKPREEQFNSTYRVVSVL

TVLHQDWLNGKEYKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQEGNVFSCSVMHE

ALHNHYTQKSLSLSLGK human IgG1 heavy chain constant region sequence
                                           SEQ ID NO: 139
ASTKGPSVFPLAPSSKSTSGGTAALGCLVKDYFPEPVTVSWNSGALTSGVHTFPAVLQSSGL

YSLSSVVTVPSSSLGTQTYICNVNHKPSNTKVDKKVEPKSCDKTHTCPPCPAPELLGGPSVE

LFPPKPKDTLMISRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKSRWQQGNVFSCSV

MHEALHNHYTQKSLSLSPGK human IgG2 heavy chain constant region sequence
                                           SEQ ID NO: 140
ASTKGPSVFPLAPCSRSTSESTAALGCLVKDYFPEPVTVSWNSGALTSGVHTFPAVLQSSGL

YSLSSVVTVPSSNFGTQTYTCNVDHKPSNTKVDKTVERKCCVECPPCPAPPVAGPSVFLFPP

KPKDTLMISRTPEVTCVVVDVSHEDPEVQFNWYVDGVEVHNAKTKPREEQFNSTFRVVSVLT

VVHQDWLNGKEYKCKVSNKGLPAPIEKTISKTKGQPREPQVYTLPPSREEMTKNQVSLTCLV

KGFYPSDISVEWESNGQPENNYKTTPPMLDSDGSFFLYSKLTVDKSRWQQGNVFSCSVMHEA

LHNHYTQKSLSLSPGK human IgG3 heavy chain constant region sequence
                                           SEQ ID NO: 141
ASTKGPSVFPLAPCSRSTSGGTAALGCLVKDYFPEPVTVSWNSGALTSGVHTFPAVLQSSGL

YSLSSVVTVPSSSLGTQTYTCNVNHKPSNTKVDKRVELKTPLGDTTHTCPRCPEPKSCDTPP

PCPRCPEPKSCDTPPPCPRCPEPKSCDTPPPCPRCPAPELLGGPSVFLFPPKPKDTLMISRT

PEVTCVVVDVSHEDPEVQFKWYVDGVEVHNAKTKPREEQYNSTFRVVSVLTVLHQDWLNGKE

YKCKVSNKALPAPIEKTISKTKGQPREPQVYTLPPSREEMTKNQVSLTCLVKGFYPSDIAVE

WESSGQPENNYNTTPPMLDSDGSFFLYSKLTVDKSRWQQGNIFSCSVMHEALHNRFTQKSLS

LSPGK human Igκ light chain constant region sequence
                                           SEQ ID NO: 142
RTVAAPSVFIFPPSDEQLKSGTASVVCLLNNFYPREAKVQWKVDNALQSGNSQESVTEQDSK

DSTYSLSSTLILSKADYEKHKVYACEVTHQGLSSPVTKSENRGEC human Igλ1 light chain constant region sequence
                                           SEQ ID NO: 143
GQPKANPTVTLFPPSSEELQANKATLVCLISDFYPGAVTVAWKADGSPVKAGVETTKPSKQS

NNKYAASSYLSLTPEQWKSHRSYSCQVTHEGSTVEKTVAPTECS human Igλ2 light chain constant region sequence
                                           SEQ ID NO: 144
GQPKAAPSVTLFPPSSEELQANKATLVCLISDFYPGAVTVAWKADSSPVKAGVETTTPSKQS

NNKYAASSYLSLTPEQWKSHRSYSCQVTHEGSTVEKTVAPTECS
```

-continued human Igλ3 light chain constant region sequence
SEQ ID NO: 145
GQPKAAPSVTLFPPSSEELQANKATLVCLISDFYPGAVTVAWKADSSPVKAGVETTTPSKQS

NNKYAASSYLSLTPEQWKSHKSYSCQVTHEGSTVEKTVAPTECS human Igλ6 light chain constant region sequence
SEQ ID NO: 146
GQPKAAPSVTLFPPSSEELOANKATLVCLISDFYPGAVKVAWKADGSPVNTGVETTTPSKQS

NNKYAASSYLSLTPEQWKSHRSYSCQVTHEGSTVEKTVAPAECS human Igλ7 light chain constant region sequence
SEQ ID NO: 147
GQPKAAPSVTLFPPSSEELQANKATLVCLVSDENPGAVTVAWKADGSPVKVGVETTKPSKQS

NNKYAASSYLSLTPEQWKSHRSYSCRVTHEGSTVEKTVAPAECS

Antibody Fragments

In certain embodiments, provided are antibody fragments, rather than whole antibodies.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the production of large amounts of these fragments. Antibody fragments can be isolated from, e.g., antibody phage libraries. Alternatively or additionally, Fab'-SH fragments can be directly recovered from E. coli and chemically coupled to form F(ab')2 fragments (Carter et al., Bio/Technology 10:163-167 (1992)). According to another approach, F(ab')2 fragments can be isolated directly from recombinant host cell culture. Fab and F(ab')2 fragment with increased in vivo half-life comprising a salvage receptor binding epitope residues are described, e.g., in U.S. Pat. No. 5,869,046. Other techniques for the production of antibody fragments will be apparent to the skilled practitioner.

In some embodiments, the antigen-binding fragment is a single chain Fv fragment (scFv). See, e.g., WO 93/16185; U.S. Pat. Nos. 5,571,894; and 5,587,458. Fv and scFv are species with intact combining sites that are devoid of constant regions; thus, these fragments may be suitable for reduced nonspecific binding during in vivo use. scFv fusion proteins may be constructed to yield fusion of an effector protein at either the amino or the carboxy terminus of an scFv. See, e.g., Antibody Engineering, ed. Borrebaeck. An antigen-binding antibody fragment may also be a "linear antibody", e.g., as described in U.S. Pat. No. 5,641,870.

Amino Acid Sequence Modifications

Amino acid sequence modification(s) of the antibodies or antigen-binding fragments disclosed herein are contemplated. For example, it may be desirable to improve the binding affinity and/or other biological properties of the antibodies or antigen-binding fragments. Amino acid sequence variants can be prepared, e.g., by introducing appropriate nucleotide changes into a nucleic acid sequence encoding the antibody or antigen-binding fragment, or by peptide synthesis. Such modifications can include, for example, deletions from, and/or insertions into and/or substitutions of, residues within the amino acid sequences of the antibody or antigen-binding fragment. Any combination of deletion, insertion, and substitution can be made, provided that the antibody or antigen-binding fragment has the desired characteristics. In some embodiments, amino acid changes are introduced to alter post-translational processes, such as changing the number or position of glycosylation sites.

A useful method for identification of certain residues or regions that are preferred locations for mutagenesis is called "alanine scanning mutagenesis," e.g., as described by Cunningham and Wells in Science, 244:1081-1085 (1989). In this method, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis may be conducted at the target codon or region, and the expressed variants may be screened for a desired activity.

Examples of amino acid sequence insertions include, but are not limited to, amino- and/or carboxyl-terminal fusions ranging in length from one residue to polypeptides containing a hundred or more residues, as well as intrasequence insertions of single or multiple amino acid residues. An example of a terminal insertion includes, but are not limited to, N-terminal methionyl residues.

In some embodiments, the antibody or antigen-binding fragment is fused at one terminus to another polypeptide, e.g., a cytotoxic polypeptide, an enzyme, or a polypeptide which increases the serum half-life of the antibody or antigen-binding fragment.

Another type of variant is an amino acid substitution variant. These variants have at least one amino acid residue in the antibody molecule or antigen-binding fragment molecule replaced by a different residue. Sites of greatest interest for substitutional mutagenesis are typically the hypervariable regions, but framework region alterations are also contemplated. Examples of conservative substitutions are shown in Table 2 under the heading of "preferred substitutions." More substantial changes, under the heading "exemplary substitutions" in Table 2, or as further described below in reference to amino acid classes, may be introduced and the resulting antibodies or antigen-binding fragments screened.

TABLE 2

Exemplary Amino acid substitutions

| Original Residue | Exemplary Substitutions | Preferred Substitutions |
|---|---|---|
| Ala (A) | Val, Leu, Ile | Val |
| Arg (R) | Lys, Gln, Asn | Lys |
| Asn (N) | Gln, His, Asp, Lys, Arg | Gln |
| Asp (D) | Glu, Asn | Glu |
| Cys (C) | Ser, Ala | Ser |
| Gln (Q) | Asn, Glu | Asn |
| Glu (E) | Asp, Gln | Asp |
| Gly (G) | Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu Phe, Ile | Leu |
| Phe (F) | Leu, Val, Ile, Ala, Tyr | Tyr |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

Substantial modifications in the biological properties of the antibody may be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are typically divided into groups based on common side-chain properties:
 (1) hydrophobic: Norleucine, Met, Ala, Val, Leu, Ile;
 (2) neutral hydrophilic: Cys, Ser, Thr;
 (3) acidic: Asp, Glu;
 (4) basic: Asn, Gln, His, Lys, Arg;
 (5) residues that influence chain orientation: Gly, Pro; and
 (6) aromatic: Trp, Tyr, Phe.

Non-conservative substitutions can entail exchanging a member of one of these classes for another class.

Additionally or alternatively, cysteine residues not involved in maintaining the proper conformation of the antibody or antigen-binding fragment may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

In some embodiments, a substitutional variant comprises a substitution within one or more hypervariable region residues of a parent antibody (e.g. a humanized or human antibody). Generally, the resulting variant(s) having improved biological properties relative to the parent antibody from which they are generated are selected for further development.

A method for generating such substitutional variants involves affinity maturation using phage display. In an example of such a method, several hypervariable region sites (e.g., 6-7 sites) are mutated to generate all possible amino substitutions at each site. Antibody variants thus generated are displayed in a monovalent fashion, e.g., from filamentous phage particles as fusions to the gene III product of M13 packaged within each particle. The phage-displayed variants are then screened for their biological activity (e.g., binding affinity).

To identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody or antigen-binding fragment and the antigen. Such contact residues and neighboring residues are candidates for substitution according to the techniques elaborated herein. Once such variants are generated, the panel of variants is subjected to screening, and antibodies with superior properties in one or more relevant assays may be selected for further development.

In some embodiments, the original glycosylation pattern of a parent antibody is altered. Such alteration(s) may comprise deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are recognition sequences for enzymatic attachment of the carbohydrate moiety to an asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody may be accomplished by altering the antibody or antigen-binding fragment's amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of antibodies or antigen-binding fragments may be prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody or antigen-binding fragment thereof.

In some embodiments, a modification that increases the serum half life of the antibody or antigen-binding fragment is used. For example, a salvage receptor binding epitope can be incorporated into an antibody (especially an antibody fragment) as described, e.g., in U.S. Pat. No. 5,739,277. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

Antibody Characteristics

In certain embodiments, a disclosed Notch4 antibody or Notch4-binding fragment thereof binds to selectively to Notch4 in that it shows detectable binding to Notch4 in a binding assay but does not show detectable binding to other Notch proteins (e.g., Notch1, Notch2, or Notch3) in a similar assay. In some embodiments, the Notch4 antibody or Notch4-binding fragment thereof is antagonistic.

In some embodiments, the Notch4 antibody binds to Notch4 with a dissociation constant ($K_D$) of ≤10 nM, ≤9 nM, ≤8 nM, ≤7 nM, ≤6 nM, ≤5 nM, ≤4 nM, ≤3 nM, ≤2 nM, or ≤1 nM. In some embodiments, the Notch4 antibody or Notch4-binding fragment thereof has a dissociation constant ($K_D$) of between 300 pM and 10 nM (inclusive of endpoints).

In one embodiment, $K_D$ is measured by a radio-labeled antigen binding assay (Radioimmunoassay, RIA) performed with the Fab version of an antibody or antigen-binding fragment thereof of interest and its antigen.

According to another embodiment, $K_D$ is measured using surface plasmon resonance assays with immobilized antigen.

Vectors, Host Cells and Recombinant Methods

Also provided are isolated nucleic acids encoding antibodies and antigen-binding fragments, vectors and host cells comprising the nucleic acid, and recombinant techniques for the production of the antibody.

For recombinant production of the antibody or antigen-binding fragment, a nucleic acid encoding the antibody or antigen-binding fragment may be isolated and inserted into a replicable vector for further cloning (amplification of the DNA) or for expression. DNA encoding the monoclonal antibody can be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

For larger scale production of antibodies, plasmids from yeast clones producing desired Notch4 antibodies can be transfected into suitable host cells, such as insect or mammalian host cells. Non-limiting examples of mammalian host cell lines that may be suitable for production of antibodies include NS0 murine myeloma cells, PER.C6® human cells, Chinese hamster ovary (CHO) cells, Sp2/0, and HEK293 cells.

Pharmaceutical Compositions

In certain embodiments, provided Notch4 antibodies are incorporated together with one or more pharmaceutically acceptable carriers into a pharmaceutical composition suitable for administration to a subject. As used herein, "pharmaceutically acceptable carrier" refers to any of a variety of solvents, dispersion media, coatings, antibacterial and antifungal agents, isotonic and absorption delaying agents, and the like that are physiologically compatible. Examples of pharmaceutically acceptable carriers include, but are not limited to, water, saline, phosphate buffered saline, dextrose, glycerol, ethanol and the like, as well as combinations thereof.

In some embodiments, pharmaceutical compositions comprise one or more tonicity agents or stabilizers. Non-limiting examples of such tonicity agents or stabilizers include sugars (e.g., sucrose), polyalcohols (e.g., mannitol or sorbitol), and sodium chloride.

In some embodiments, pharmaceutical compositions comprise one or more bulking agents and/or lyoprotectants (e.g., mannitol or glycine), buffers (e.g., phosphate, acetate, or histidine buffers), surfactants (e.g., polysorbates), antioxidants (e.g., methionine), and/or metal ions or chelating agents (e.g., ethylenediaminetetraacetic acid (EDTA)).

In some embodiments, pharmaceutical compositions comprise one or more auxiliary substances such as wetting or emulsifying agents, preservatives (e.g., benzyl alcohol) or buffers, which may enhance the shelf life and/or effectiveness of Notch4 antibodies disclosed herein.

Pharmaceutical compositions may be provided in any of a variety of forms. These include, for example, liquid, semi-solid and solid dosage forms, such as liquid solutions (e.g., injectable and infusible solutions), dispersions or suspensions, tablets, pills, powders, liposomes and suppositories. Suitability of certain forms may depend on the intended mode of administration and therapeutic application.

In some embodiments, pharmaceutical compositions are in the form of injectable or infusible solutions.

Pharmaceutical compositions are typically sterile and stable under conditions of manufacture, transport, and storage. Pharmaceutical compositions may be formulated as, for example, a solution, microemulsion, dispersion, liposome, or other ordered structure. In some embodiments, a pharmaceutical composition is formulated as a structure particularly suitable for high drug concentration. For example, sterile injectable solutions can be prepared by incorporating a therapeutic agent (e.g., Notch4 antibody) in a desired amount in an appropriate solvent with one or a combination of ingredients enumerated herein, optionally followed by sterilization (e.g., filter sterilization). Generally, dispersions may be prepared by incorporating a therapeutic agent (e.g., Notch4 antibody) into a sterile vehicle that contains a basic dispersion medium and other ingredient(s) such as those additional ingredients mentioned herein. In the case of sterile powders for the preparation of sterile injectable solutions, examples of preparation methods include vacuum drying and freeze-drying to yield a powder of the therapeutic agent and any additional desired ingredient(s), e.g., from a previously sterile-filtered solution thereof.

Proper fluidity of a solution can be maintained, for example, by the use of a coating such as lecithin, by maintaining certain particle sizes (e.g., in the case of dispersions), and/or by using surfactants. Prolonged absorption of injectable compositions can be brought about, e.g., by including in the composition an agent that delays absorption (for example, monostearate salts and/or gelatin).

Production of Human Notch4 Antibodies

As described further in the Examples, the presently disclosed antibodies are fully human antibodies which were identified using phage display technology (McCafferty et al., Nature 348:552-553 [1990]), which can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573,905.

For larger scale production of antibodies, plasmids from yeast clones producing desired Notch4 antibodies can be transfected into suitable host cells, such as host cells further described herein. (See "Vectors, Host Cells, and Recombinant Methods" subsection)

Methods of Treatment

Methods of treating airway inflammation and/or related conditions disclosed herein generally comprise a step of administering a therapeutically effective amount of a Notch4 antibody or Notch4-binding fragment thereof (or pharmaceutical composition thereof) of the present disclosure to a mammalian subject (e.g., a human subject) in need thereof. In some embodiments, the airway inflammation is chronic airway inflammation. In some embodiments, the subject is diagnosed as having or at risk of having an airway inflammation-associated disorder, for example, asthma (e.g., severe eosinophilic asthma), chronic obstructive pulmonary disorder (COPD), cystic fibrosis (CF), or bronchopulmonary dysplasia (BPD).

In some embodiments, the step of administering comprises systemic administration of the therapeutically effective amount, e.g., an intravenous, subcutaneous, or intramuscular route.

Therapeutically effective amounts may be administered via a single dose or via multiple doses (e.g., at least two, at least three, at least four, at least five, at least six, at least seven, at least eight, at least nine, or at least ten doses). When administered via multiple doses, any of a variety of suitable therapeutic regimens may be used, including administration at regular intervals (e.g., once every other day, once every three days, once every four days, once every five days, thrice weekly, twice weekly, once a week, once every two weeks, once every three weeks, etc.).

The dosage regimen (e.g., amounts of each therapeutic, relative timing of therapies, etc.) that is effective in methods of treatment may depend on the severity of the disease or condition and the weight and general state of the subject. For example, the therapeutically effective amount of a particular composition comprising a therapeutic agent applied to mammals (e.g., humans) can be determined by the ordinarily-skilled artisan with consideration of individual differences in age, weight, and the condition of the mammal. Therapeutically effective and/or optimal amounts can also be determined empirically by those of skill in the art. In some embodiments, subjects are administered a dose between 0.4 mg/kg every 3 days to 20 mg/kg every 3 days. Notch4 antibodies and pharmaceutical compositions thereof may be administered by any of a variety of suitable routes, including, but not limited to, systemic routes such as parenteral (e.g., intranasal, intravenous, or subcutaneous) or enteral routes.

In some embodiments, administration of the antibody or a pharmaceutical composition thereof results in improvement in one or more symptoms or signs of airway inflammation or an associated disorder. For example, airway hyperresponsiveness may be ameliorated as a result of administration of the antibody or a pharmaceutical composition. For example, in a methacholine challenge test, airway hyperresponsiveness as measured from calculated peak airway resistance may be 75% or less, 70% or less, 65% or less, 60% or less, 55% or less 50% or less, 45% or less, 40% or less, 35% or less, or 30% or less of than that of a reference level.

As another example, other indications of inflammation such as presence of eosinophils, CD4+ Th2 cells, or neutrophils in bronchoalveolar lavage fluid; allergen-specific IgE responses, or Th cell cytokine expression (e.g., IL-4 and/or IL-13) may be reduced as a result of administration of the antibody or a pharmaceutical composition. Metrics for any one or any combination of these indications of inflammation may be reduced such that they are 75% or less, 70% or less, 65% or less, 60% or less, 55% or less 50% or less, 45% or less, 40% or less, 35% or less, or 30% or less of than that of a reference level.

EXAMPLES

Example 1. Identification and Production of Humanized Antibodies Specific to Notch4

Notch4 shares sequence homology (approximately 50% amino acid sequence identity) with each of Notch1, Notch2, and Notch3. The present Example describes the production of humanized Notch4 antibodies specific to human Notch4 using phage display technology.

Recombinant human Notch4 was used as antigen for positive selection, and recombinant human Notch1, Notch2, and Notch3, were used as antigens for negative selection of candidate antibodies. Recombinant Notch4 protein was biotinylated and assessed for biotinylation using SDS-PAGE electrophoresis and size exclusion chromatography (HPLC-SEC).

Phage libraries based on abrilumab (Lib1), mepolizumab (Lib2A), crenezumab (Lib3), necitumumab (Lib4), evolocumab (Lib6) and adalimumab (Lib8) were exposed to the biotinylated human Notch4. The final selection output was tested using polyclonal phage ELISA assay using the biotinylated Notch4 antigen and a control off-target protein. The final selection outputs were subcloned into a yeast display vector and analyzed using flow cytometry to detect and sort for a human Notch4-binding population. The Notch4-binding-enriched population was then deselected for clones that bound to the other Notch proteins (Notch1, Notch2, and Notch3) and/or subjected to competition with other Notch proteins, in order to retain clones that showed specific binding activity to Notch4.

The Notch4-binding-enriched population was then subjected to epitope competition assays with a Notch4 antibody (either 4H1 or 3B11; see International Patent Publication No. WO 2022/081971) known to interfere with Notch4 binding to Jagged1, a Notch ligand. Briefly, a "sandwich" assay was performed using the yeast displaying anti-Notch4 antibodies to capture Notch4; subsequently, the yeast were incubated with 4H1 or 3B11 and the latter detected with a secondary reagent fluorescently labelled. Detection of 4H1 or 3B11 binding signal led to the identification and sorting of yeast displaying clones not competing for the same epitope of either one of the two monoclonal antibodies (4H1 or 3B11). Absence of binding signal detection on the same population incubated with 4H1 or 3B11 led to the identification and sorting of yeast displaying clones competing for the same epitope of either one of the two monoclonal antibodies.

Clones that successfully competed with 4H1 or 3B11, which should therefore also able to inhibit binding Notch4 to Jagged1, were selected for further analysis as described in Example 2.

Example 2. Characterization of Notch4 Antibodies

Candidate Notch4-specific antibodies identified in Example 1 were further characterized to determine their sequences and binding parameters.

Materials and Methods

Sequencing. A combined parallel sequencing approach was implemented including Sanger-based screening and Next-generation sequencing (NGS). For Sanger-based screening, up to 4×96 individual clones were sequenced and unique clones were identified.

PacBio sequencing was performed on yeast selection output DNA for each candidate antibody. Sequence clonotypes were identified by analyzing the PacBio output data. Unique clusters of positive clones were identified using the Sanger sequencing data to ensure that not all Sanger clones belonged to a single cluster.

Binding kinetics measurements. Following expression and purification, clones were characterized using surface plasmon resonance (SPR) to determine binding kinetics and epitope binding activity. HC30M chips (polycarboxylate hydrogel surfaces having medium charge density and 30 nm coating thickness) were coated with anti-human Fc antibodies (unlabeled goat anti-human IgG Fc from Southern Biotech) to capture the candidate antibodies. Candidate antibodies were diluted to 10 µg/mL in HEPES-buffered saline Tris-EDTA (HBSTE)) and exposed to the surfaces for 15 minutes. After stabilizing baseline using HBSTE, Notch4 analytes were injected sequentially from a lowest concentration of 0.41 nM to a highest concentration of 300 nM. (Notch4 was diluted in HBSTE+0.5 mg/mL bovine serum albumin (BSA) to obtain a series of 3-fold dilutions.) To assess specificity, experiments were also run using Notch2 as an analyte in a single injection at 100 nM in HBSTE+0.5 mg/mL.

Results

The sequences and binding characteristics of nineteen candidate Notch4 antibodies were obtained. Table 1 of this disclosure lists the $V_H$, $V_K$, and CDR sequences of representative candidate clones.

Table 3 (below) summarizes the binding parameters of the candidate clones from this experiment.

TABLE 3

Binding parameters of candidate Notch4 antibodies as determined by surface plasmon resonance

| Antibody clone | $K_D$ | $k_{on}$ | $k_{off}$ |
|---|---|---|---|
| iggrefmat 6-16 | 380 pM | $3.2 \times 10^5$ | $1.2 \times 10^{-4}$ |
| C08-Lib3-Pl1 | 410 pM | $1.2 \times 10^5$ | $4.7 \times 10^{-5}$ |
| iggrefmat 3-11 (same as H03-Lib6-Pl2) | 920 pM | $1.0 \times 10^5$ | $9.3 \times 10^{-5}$ |
| iggrefmat 2-12 (same as E08-Lib3-Pl1) | 5.6 nM | $9.0 \times 10^4$ | $5.1 \times 10^{-4}$ |
| H07-Lib3-Pl1 | 1.4 nM | $7.7 \times 10^4$ | $1.1 \times 10^{-4}$ |
| Iggrefmat 1-12 (same as C02-Lib1_Pl1) | 1.5 nM | $1.1 \times 10^5$ | $1.3 \times 10^{-4}$ |
| iggrefmat 2-16 (same as C07-Lib3-Pl1) | 1.5 nM | $7.7 \times 10^4$ | $1.2 \times 10^{-4}$ |
| iggrefmat 1-34 | 1.5 nM | $1.0 \times 10^5$ | $1.5 \times 10^{-4}$ |
| G04-Lib6-Pl2 | 1.6 nM | $8.8 \times 10^4$ | $1.4 \times 10^{-4}$ |
| iggrefmat 3-13 (same as C11-Lib4-Pl1) | 2.5 nM | $9.4 \times 10^4$ | $2.4 \times 10^{-4}$ |
| iggrefmat 3-4 (same as D11-Lib4-Pl1) | 2.6 nM | $7.2 \times 10^4$ | $1.9 \times 10^{-4}$ |
| C04-Lib1-Pl1 | 2.9 nM | $4.9 \times 10^4$ | $1.4 \times 10^{-4}$ |
| iggrefmat 6-28 (same as E03-Lib8H1N4) | 3.4 nM | $1.1 \times 10^5$ | $3.8 \times 10^{-4}$ |
| B07-Lib3-Pl1 | 5.0 nM | $3.0 \times 10^4$ | $1.5 \times 10^{-4}$ |
| C03-Lib1-Pl1 | 5.3 nM | $4.2 \times 10^4$ | $2.2 \times 10^{-4}$ |
| iggrefmat 1-29 (same as C01-Lib1-Pl1) | 6.1 nM | $5.5 \times 10^4$ | $3.4 \times 10^{-4}$ |
| G05-Lib3-Pl1 | 890 pM | $2.2 \times 10^5$ | $2.0 \times 10^{-4}$ |

Example 3. Therapeutic Effect of Notch4 Antibodies in a Humanized In Vivo Mouse Model Five of the Notch4-specific antibodies identified in Example 1 and characterized in Example 2 were further analyzed for their in vivo effects in a humanized mouse model of allergen-induced inflammation.

Materials and Methods:

Humanized Mouse Allergen-Induced Inflammation Model

Peripheral blood mononuclear cell (PBMC) humanized mice were obtained from JAX®. "NSG"™ mice carry a scid (severe combined immune deficiency) mutation and a complete null allele of the IL2 receptor common gamma chain (IL2rg$^{null}$) and are extremely immunodeficient. Female NSG™ mice were injected with human peripheral blood mononuclear cells (hu-PBMCs). Mice were kept in specific pathogen-free (SPF) conditions for week before sensitization to allergen.

To sensitize mice, mice were intranasally administered 50 µL of a solution of house dust mite (HDM) extract (available from Stallergenes Greer) (5 µg HDM per 100 µL) phosphate-buffered saline on days 1, 2, and 3 of the experiment. On days 15, 16, and 17, mice were challenged again by intranasal administration of HDM at the same concentrations and volume.

At the end of the experiment, on day 18, mice were euthanized bronchoalveolar lavage (BAL) fluid and lung tissues were collected for subsequent analyses.

Antibody Treatment

Allergen-sensitized mice were administered one of the test Notch4 antibody clones (C08-Lib3, iggrefmat 6-28, iggrefmat 3-11, H07-Lib3, or iggrefmat 6-16) by intraperitoneal (i.p.) injection. 100 µL of a 10 µg/mL antibody solution was administered on days 1, 2, 3, 15, and 16 of the experiment. For comparison, one group of mice was administered 4H1, a previously described Notch4 antibody (see International Patent Publication No. WO 2022/081971). A control group was administered an isotype (IgG) control.

Methacholine Challenge and Airway Hyperresponsiveness

On day 18 of the experiment, mice were anesthetized and exposed to doubling concentrations (10 mg/mL, 20 mg/mL, and 40 mg/mL) of aerosolized acetyl-β-methacholine (Sigma-Aldrich) by using a Buxco small-animal ventilator (Data Sciences International). The relative peak airway resistance for each methacholine dose, normalized to the saline baseline, was calculated.

FACS Analyses

Bronchoalveolar lavage fluid was analyzed by flow cytometry. Effector T (Teff) cell populations were analyzed by gating on a CD3$^+$CD4$^+$Foxp3$^-$ population and assessing (1) IL-4 and IL-13 intracellular expression and (2) CCR6 expression. Regulatory T cells (Treg) were analyzed for Notch4 expression by gating on a CD3$^+$CD4$^+$Foxp3$^+$ population.

Therapeutic Effect of Notch4 Antibodies in a Model of Airway Hyperresponsiveness To assess the ability of the novel Notch4-specific antibodies to ameliorate airway inflammation, humanized mice sensitized to house dust mite allergen were subjected to a methacholine challenge test. FIG. 1 shows the airway hyperresponsiveness, as determined by the relative peak airway resistance calculated at the highest dose of methacholine tested (40 mg/mL), in each of the treatment groups. As can be seen in FIG. 1, treatment with iggrefmat 6-28, H07-Lib3, or iggrefmat 6-16 resulted in significant reductions in airway hyperresponsiveness relative to that observed in the isotype control, and this reduction was comparable to or better than that observed with the 4H1 antibody.

The antibodies were generally well-tolerated in mice, with most mouse groups showing no excess mortality after dosing with the fully human Notch4 antibodies. However, mice treated with C08-Lib3 showed somewhat reduced survival (60% survival at 20 days after dosing with antibody) relative to the other groups. (Data not shown)

Effect of Notch4 Antibodies on Inflammation

To assess the effects of treatment with novel Notch4-specific antibodies on inflammation, intracellular IL-4 and IL-13 expression was assessed in T effector cells from bronchoalveolar lavage (BAL) fluid. IL-4 and IL-13 are expressed in Th2 cells in response to asthmatic inflammation. CCR6 (a chemokine receptor expressed on Th2 cells).

Figure 2A:
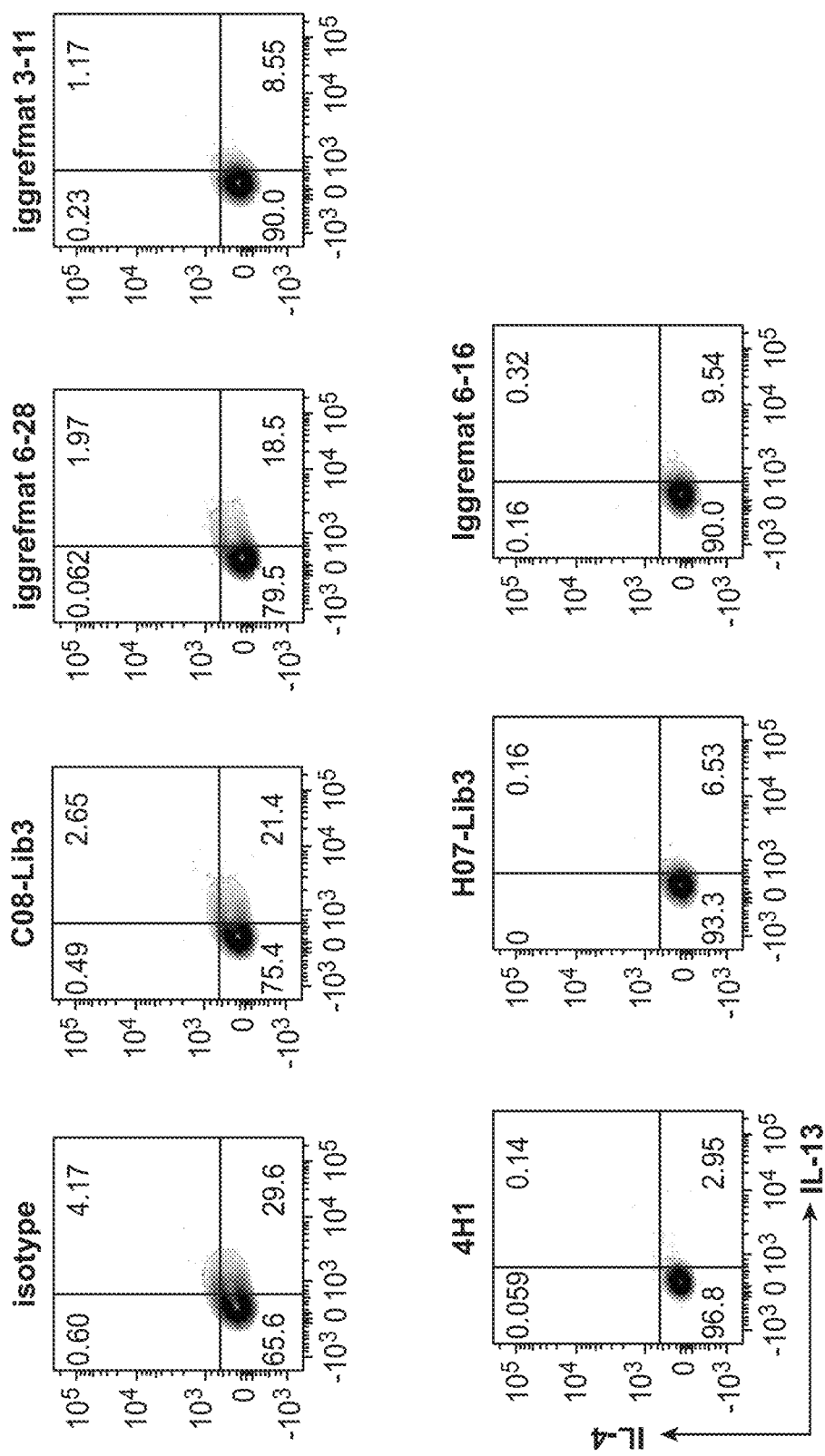
FIG. 2A shows representative IL-4 and IL-13 flow cytometry plots for Teff cells from bronchoalveolar lavage fluid from individual PBMC humanized mice sensitized to house dust mite allergen and treated with novel Notch4-specific antibodies (C08-Lib3, iggrefmat 6-28, iggrefmat 3-11, H07-Lib3, and iggrefmat 6-16), 4H1, or an isotype control.
Figure 2B:
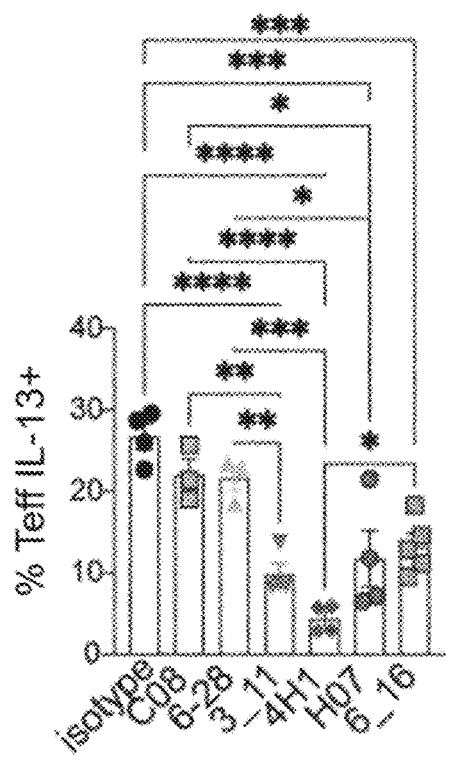
FIGS. 2B and 2C shows the average percentages of IL13-positive and IL4-positive cells, respectively, among Teff cells for the various groups. * denotes $p<0.05$,  denotes $p<0.01$, and * denotes $p<0.001$.
Figure 2C:
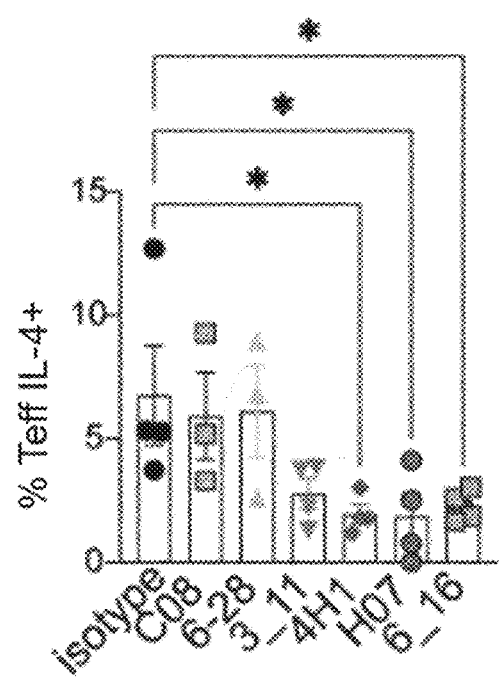

FIG. 2A shows representative flow cytometry plots for BAL fluid Teff cells stained for IL-4 and IL-13 from individual mice in each of the treatment groups; and FIGS. 2B and 2C shows the average percentages of IL13-positive and IL4-positive cells, respectively, among Teff cells for the various groups. As shown in FIG. 2A, administration of the tested antibodies appeared to result in reduced proportions of IL-4$^+$IL13$^+$ cells, with H07-Lib3 exhibiting similar levels of double-positive Teff cells as the 4H1 antibody. Treatment with three of the Notch4 antibodies (iggrefmat 3-11, H07-Lib3, and iggrefmat 6-16) resulted in significant decreases in the proportion of IL-13+ cells relative to the isotype control (FIG. 2B), and treatment with two of the Notch4 antibodies (H07-Lib3, and iggrefmat 6-16) resulted in significant decreases in the proportion of IL-13+ cells relative to the isotype control (FIG. 2C).

Figure 3A:
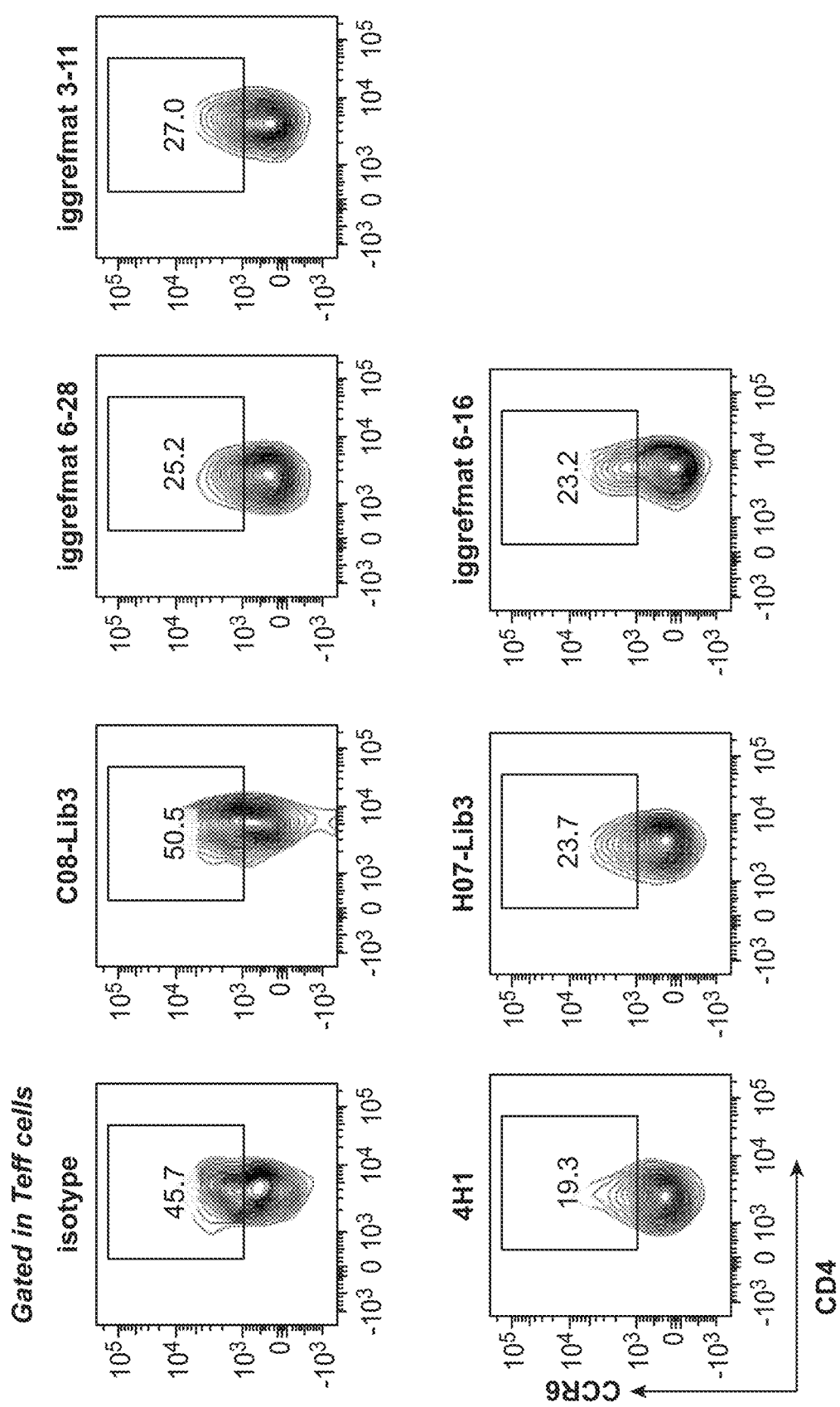
FIG. 3A shows representative flow cytometry plots for BAL fluid Teff cells stained for CD4 and CCR6 from individual PBMC humanized mice sensitized to house dust mite allergen and treated with novel Notch4-specific antibodies (C08-Lib3, iggrefmat 6-28, iggrefmat 3-11, H07-Lib3, and iggrefmat 6-16), 4H1, or an isotype control.
Figure 3B:
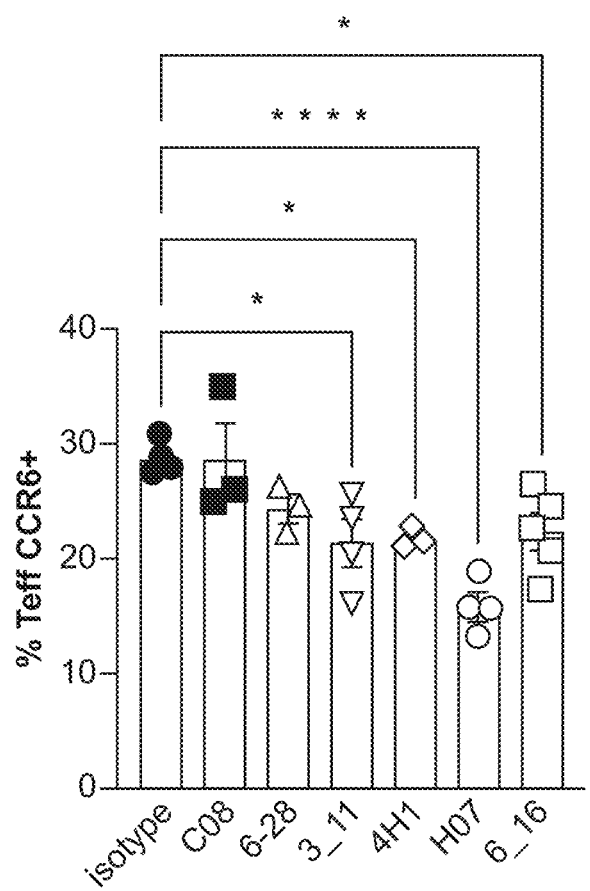
FIG. 3B shows the average percentages of CCR6-positive cells among Teff cells for each treatment group.

FIG. 3A shows representative flow cytometry plots for BAL fluid Teff cells stained for CD4 and CCR6 from individual mice in each of the treatment groups; and FIG. 3B shows the average percentages of CCR6-positive cells among Teff cells for the various groups. Treatment with three of the Notch4 antibodies (iggrefmat 3-11, H07-Lib3, and iggrefmat 6-16) resulted in significant decreases in the proportion of CCR6+ cells relative to the isotype control (FIG. 2B).

These results suggest that treatment with some of the Notch4 antibodies resulted in less inflammation and less attraction of Th2 cells to the lung tissues.

Inhibition of Notch4 Expression on Treg Cells In Vivo by Notch4 Antibodies

Notch4 is expressed on Treg cells, and its signaling in Treg cells drives allergic inflammation induced either by allergens or particulate matter pollutants (see, e.g., International Patent Publication No. WO 2019/178488). To assess whether the novel Notch4-specific antibodies were able to block Notch4 expression on Treg cells, Treg cells from mice treated with antibodies were assessed for Notch4 expression by flow cytometry.

Figure 4A:
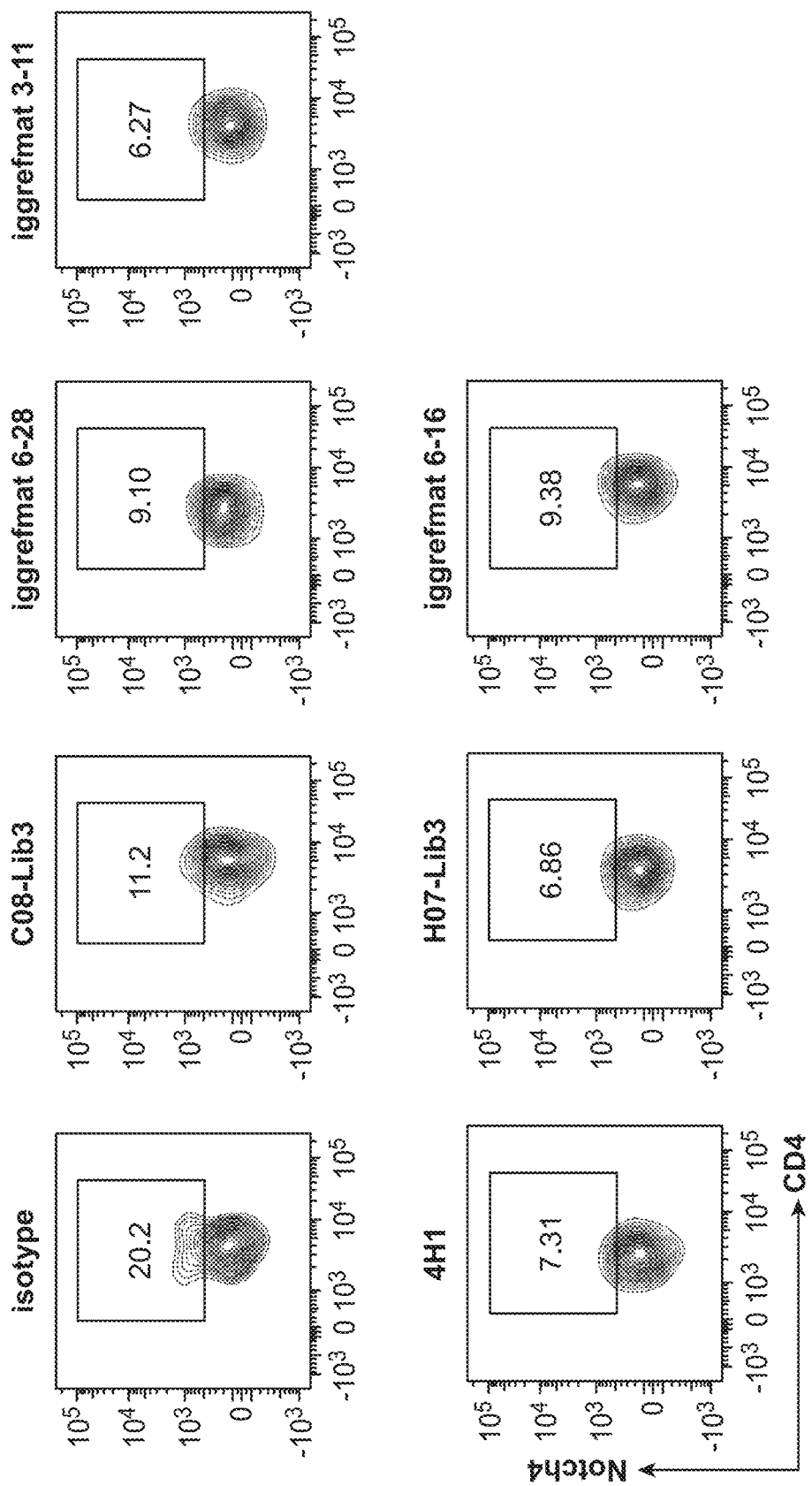
FIG. 4A shows representative flow cytometry plots for Teff cells from bronchoalveolar lavage fluid from individual PBMC humanized mice sensitized to house dust mite allergen and treated with novel Notch4-specific antibodies (C08-Lib3, iggrefmat 6-28, iggrefmat 3-11, H07-Lib3, and iggrefmat 6-16), 4H1, or an isotype control.

FIG. 4A shows representative flow cytometry plots from individual mice in each of the treatment groups; and FIG. 4B shows the average percentages of Notch4-positive cells among Treg cells for the various groups. As shown in FIGS. 4A and 4B, administration of any one of the five tested antibodies reduced the percentage of Notch4-positive Treg cells relative to the isotype control, and the levels of Notch4-positive Treg cells appeared comparable to that observed in mice treated with 4H1 antibody. FIG. 4C shows the average percentages of Notch4-positive cells among T effector (Teff) cells for the same treatment groups. In Teff cells, the percentages of Notch4-positive cells was very low and appeared similar across all groups.

These results demonstrate that three of the Notch4-specific antibodies (iggrefmat 6-28, H07-Lib3, and iggrefmat 6-16 resulted) showed therapeutic effect in vivo in a humanized mouse allergen model.

Example 4. Evaluation of Binding Specificity of H07-Lib3 to Notch4 In Vitro

Specificity of Notch4-specific antibody clone H07-Lib3 was further evaluated using in vitro assays.

Materials and Methods:

Binding specificity measurements. The binding specificity of H07-Lib3 to Notch4 was evaluated by enzyme-linked immunosorbent assay (ELISA). ELISA was performed on samples containing Notch3 or Notch4 protein, or bovine serum albumin (BSA, control). Antibody-antigen binding was measured by absorbance at 450 nm light.

Epitope binning assay. The epitope specificity of H07-Lib3 was assessed against a commercial Notch4 monoclonal mouse antibody (MHN4-2 available from BioLegend) by performing a competition ELISA assay. Assays were performed in samples with Notch4 (antigen) with or without MHN4-2. Antibody-antigen binding was measured by absorbance at 450 nm.

Binding kinetics measurements. H07-Lib3 binding kinetics were determined using surface plasmon resonance (SPR). CM5 chips were coated with anti-human polyclonal Fc antibodies (Southern Biotech) to capture candidate antibody. Candidate antibody was diluted in HEPES-buffered saline with 0.005% surfactant P20 (HBS-P) and exposed to the surfaces for 20 minutes. Notch4 analytes were injected at 300 nM to determine affinity of candidate antibody. To assess specificity, experiment was also run using Notch3 as an analyte at 300 nM.

Specificity of H07-Lib3 to Notch4

Figure 5A:
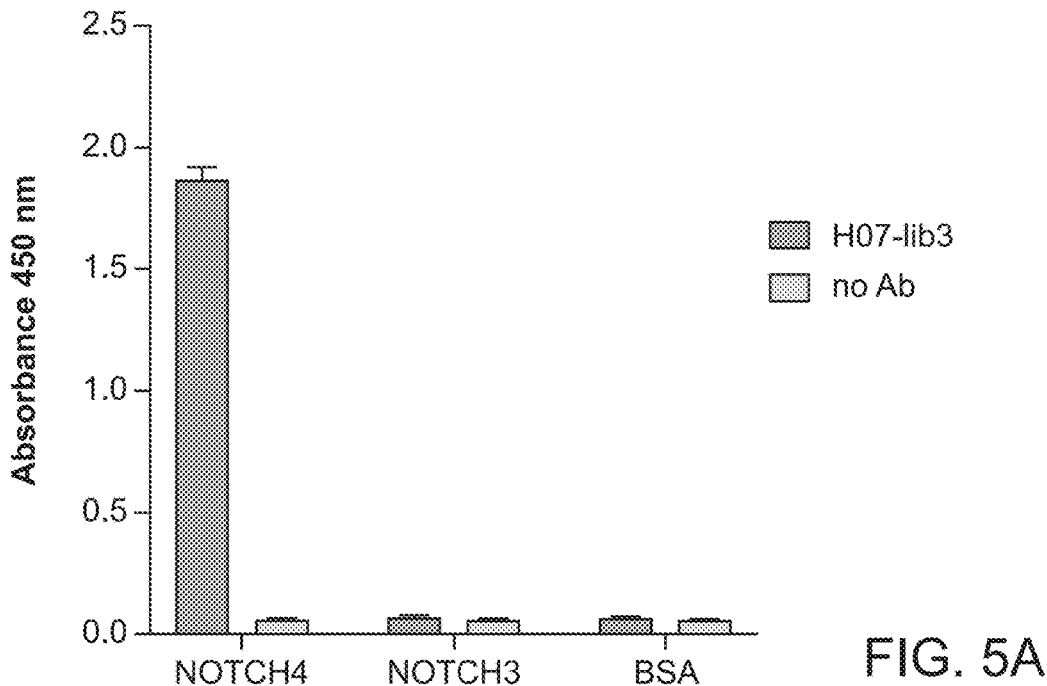
FIG. 5A shows the average absorbance at 450 nm in samples with and without Notch4-specific antibody H07-Lib3 in an ELISA-based assay to assess binding to Notch4 or Notch3. Binding to BSA was also assessed as a control.

To determine specificity of the Notch4-specific antibody clone H07-Lib3 to Notch4, ELISA experiments were performed. FIG. 5A shows binding of H07-Lib3 to Notch4, Notch3, and bovine serum albumin, as measured by the average absorbance at 450 nm. As can be seen in FIG. 5A.

Figure 5B:
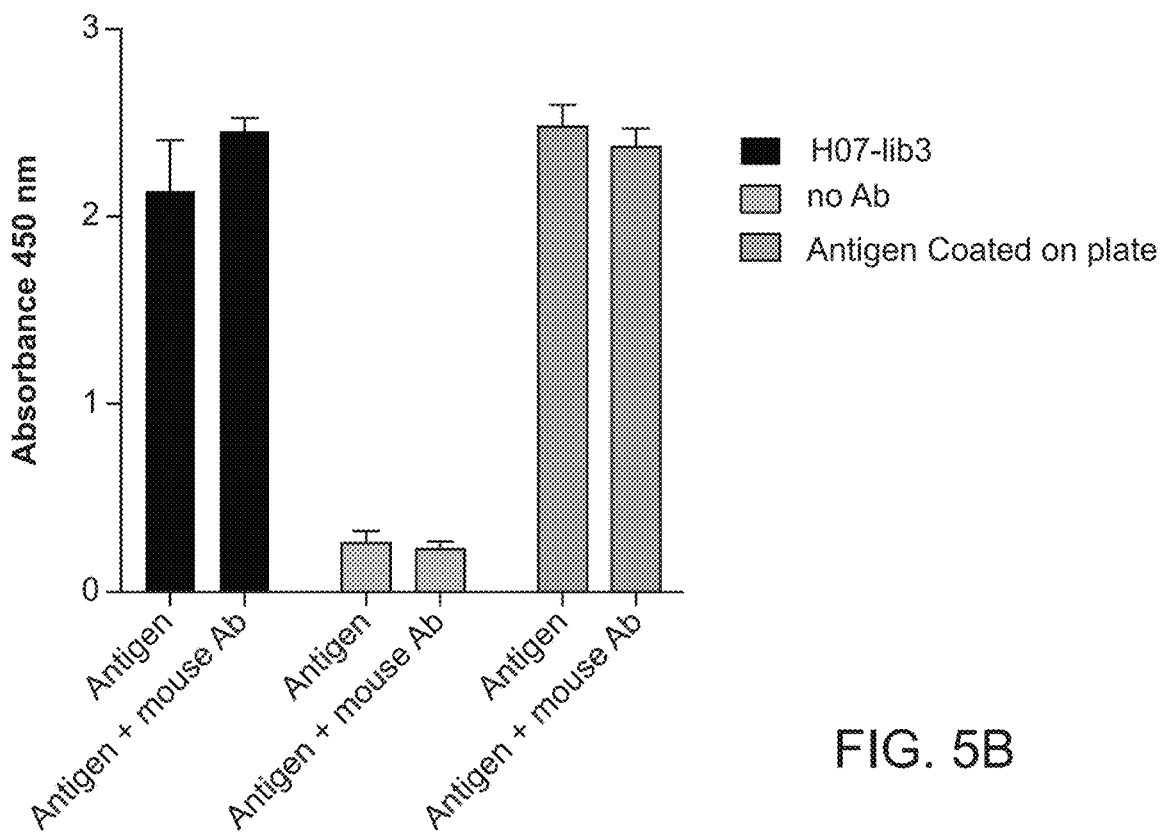
FIG. 5B shows average absorbance at 450 nm in a binding competition assay experiment between H07-Lib3 and a commercial mouse monoclonal Notch4 antibody to Notch4 (antigen).
Figure 6A:
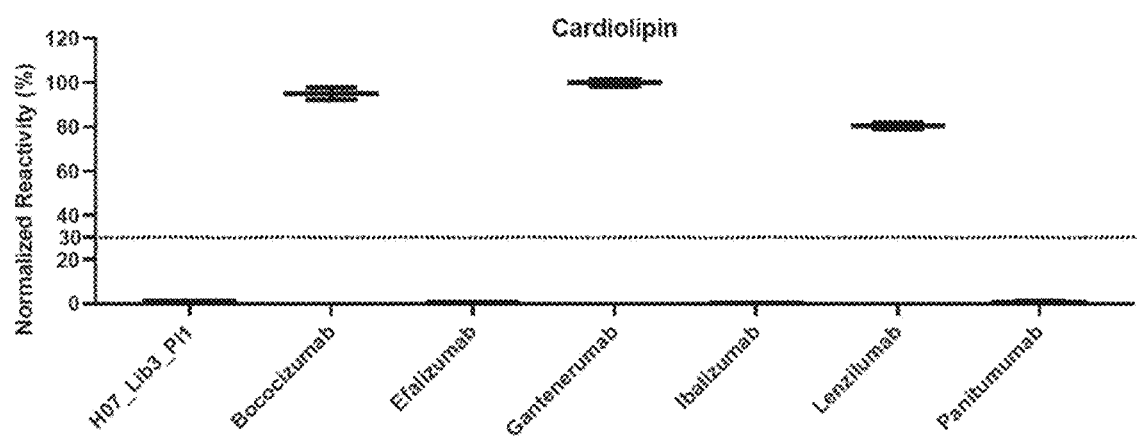
FIG. 6A shows normalized reactivity of Notch4-specific antibody H07-Lib3 and other commercial, therapeutic antibodies (bococizumab, efalizumab, gantenerumab, ibalizumab, lenzilumab, and panitumumab) against cardiolipin.
Figure 6B:
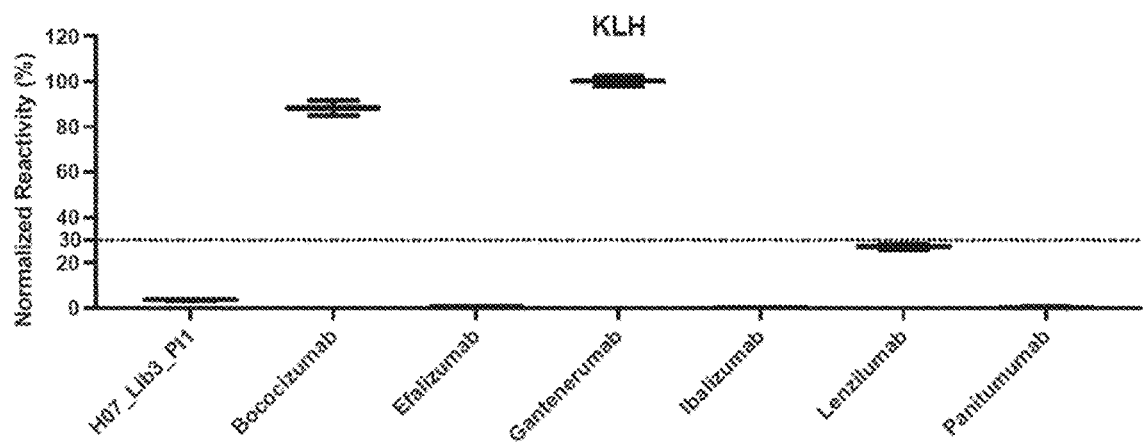
FIG. 6B shows normalized reactivity of H07-Lib3 and other commercial, therapeutic antibodies (bococizumab, efalizumab, gantenerumab, ibalizumab, lenzilumab, and panitumumab) against keyhole limpet hemocyanin (KLH).
Figure 6C:
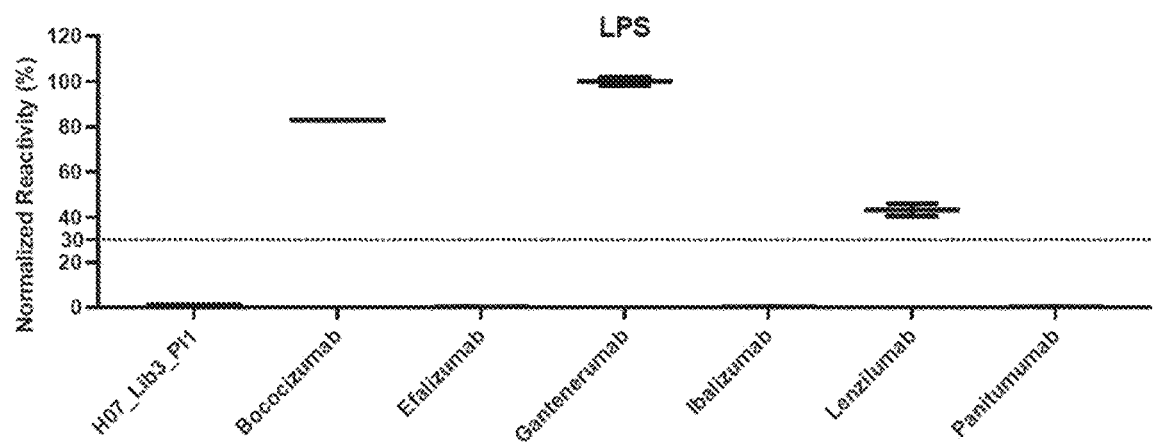
FIG. 6C shows normalized reactivity of H07-Lib3 and other commercial, therapeutic antibodies (Bococizumab, Efalizumab, Gantenerumab, Ibalizumab, Lenzilumab, and Panitumumab) against lipopolysaccharides (LPS).
Figure 6D:
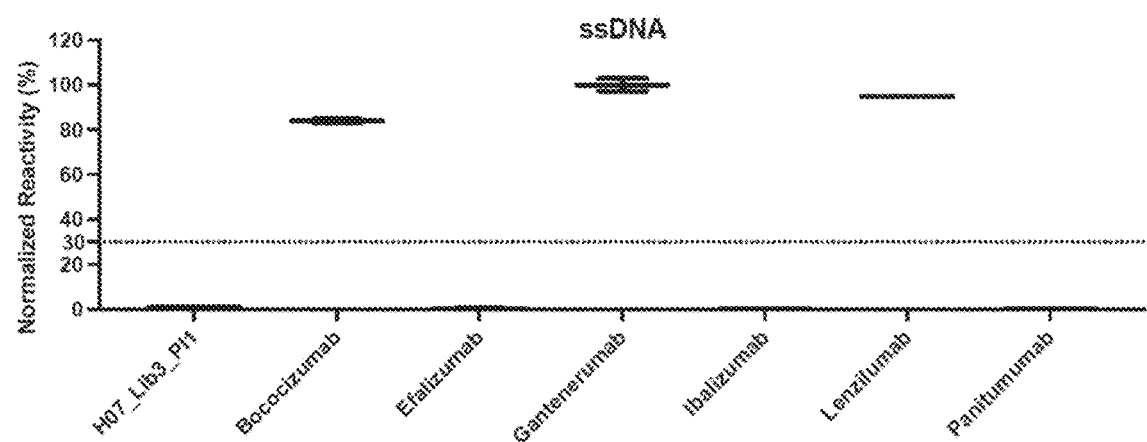
FIG. 6D shows normalized reactivity of H07-Lib3 and other commercial, therapeutic antibodies (Bococizumab, Efalizumab, Gantenerumab, Ibalizumab, Lenzilumab, and Panitumumab) against single-stranded DNA (ssDNA).
Figure 6E:
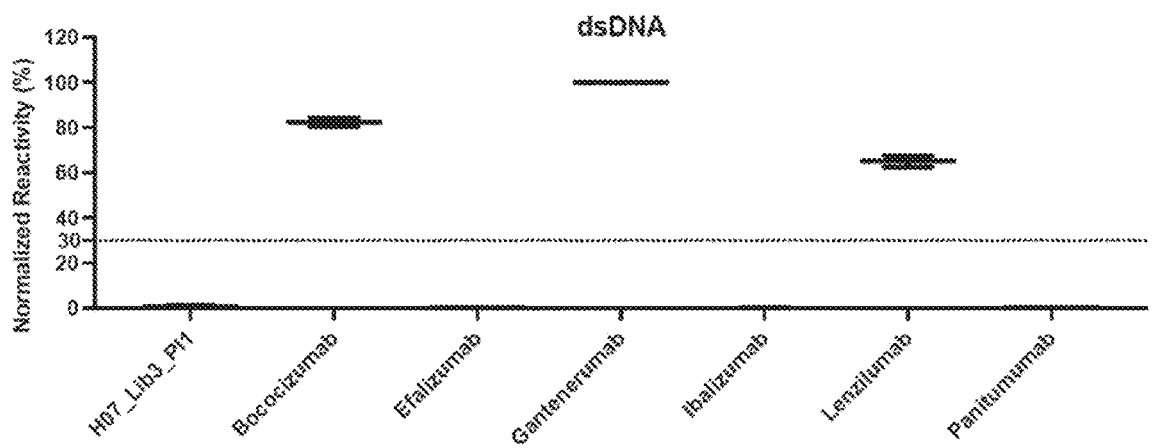
FIG. 6E shows normalized reactivity of H07-Lib3 and other commercial, therapeutic antibodies (Bococizumab, Efalizumab, Gantenerumab, Ibalizumab, Lenzilumab, and Panitumumab) against double-stranded DNA (dsDNA).
Figure 6F:
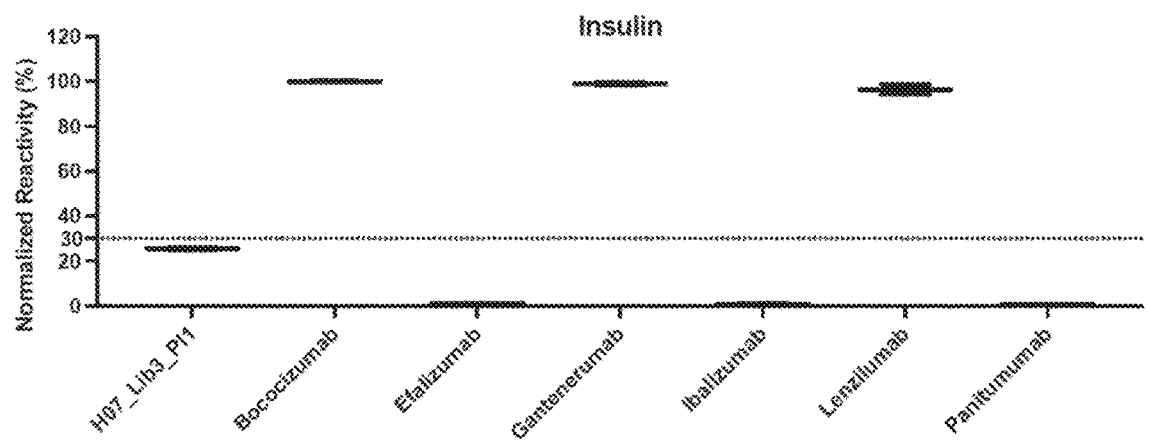
FIG. 6F shows normalized reactivity of H07-Lib3 and other commercial, therapeutic antibodies (Bococizumab, Efalizumab, Gantenerumab, Ibalizumab, Lenzilumab, and Panitumumab) against insulin.
Figure 6G:
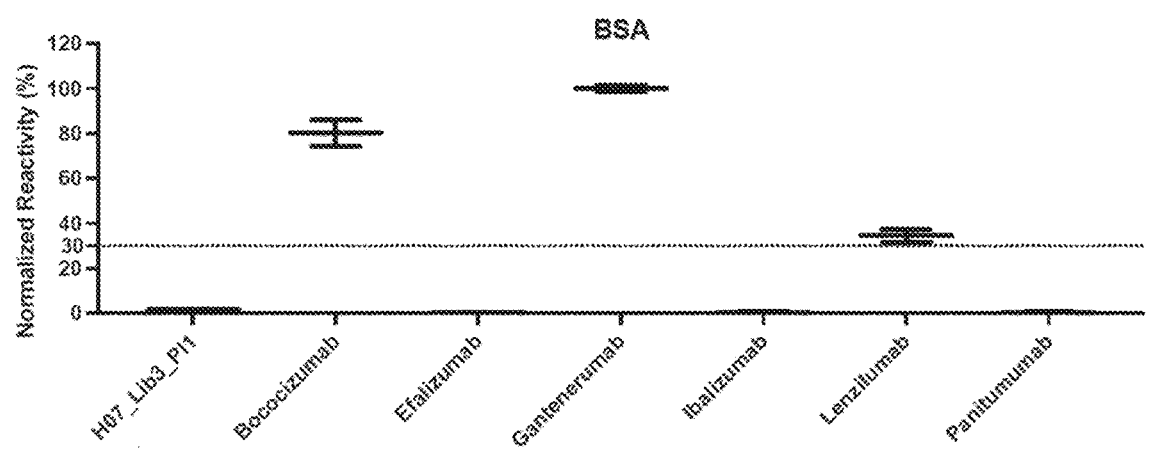
FIG. 6G shows normalized reactivity of H07-Lib3 and other commercial, therapeutic antibodies (Bococizumab, Efalizumab, Gantenerumab, Ibalizumab, Lenzilumab, and Panitumumab) against bovine serum albumin (BSA).

FIG. 5B shows epitope binning of H07-Lib3 and a commercial Notch4 antibody (mouse Ab). H07-Lib3 binding to Notch4 was observed both in absence and presence of the mouse Ab, as seen by the increased average absorbance at 450 nm compared to the samples with no antibody added.

These results demonstrate that H07-Lib3 binds to Notch4 but not Notch3, and that mouse antibody MHN4-2 does not compete with H07-Lib3 binding to Notch4.

Binding Kinetics of H07-Lib3 to Notch4

Table 4 (below) summarizes the binding parameters of H07-Lib3 as determined by surface plasmon resonance (SPR).

TABLE 4

Binding parameters of candidate Notch4 antibody H07-Lib3 as determined by surface plasmon resonance

| Analyte | $K_D$ | $k_{on}$ (/M/s) | $k_{off}$ (/s) |
|---|---|---|---|
| Notch4 | 16.6 nM | $9.83 \times 10^4$ | $1.64 \times 10^{-3}$ |
| Notch3 | | No binding | |

Example 5. Characterization of H07-Lib3 Stability

To evaluate the developability of candidate Notch4-specific antibody H07-Lib3, H07-Lib3's stability was evaluated.

Materials and Methods

Melting temperature measurements. Melting temperatures of H07-Lib3 and two control monoclonal antibodies (Control mAb1 and Control mAb2) were determined by measuring the intrinsic fluorescence emission of certain amino acids (e.g., tryptophan, tyrosine, and phenylalanine) in each sample after excitation with a 266 nm laser. The second inflection point of the plotted melting curve was identified to determine the melting temperature ($Tm_2$).

Aggregation temperature measurements. Aggregation temperatures (the temperatures at which protein aggregation begins) of H07-Lib3 and two control monoclonal antibodies (Control mAb1 and Control mAb2) were determined by measuring intrinsic fluorescence of aromatic amino acids and static light scattering (SLS). Intrinsic fluorescence of 266 nm light ($Tagg_{266}$) was measured for small concentrations and smaller aggregate formation, and SLS of 473 nm light ($Tagg_{473}$) was measured for larger concentrations and larger aggregate formation.

Results

The melting and aggregation temperatures of H07-Lib3, Ctrl mAb1, and Ctrl mAb2 were obtained. Table 5 (below) summarizes the temperature parameters of the antibodies from this experiment.

TABLE 5

Melting and aggregation temperatures of H07-Lib3 and control antibodies

| Antibody clone | $Tm_2$ | $Tagg_{266}$ | $Tagg_{473}$ |
|---|---|---|---|
| H07-Lib3 | 80.0 ± 0.2° C. | 83.7 ± 0.6° C. | 81.9 ± 2.1° C. |
| Control mAb1 | 69.9 ± 0.2° C. | 71.1 ± 0.2° C. | 69.3 ± 3.5° C. |
| Control mAb2 | 68.2 ± 0.2° C. | 71.2 ± 0.2° C. | 70.9 ± 0.7° C. |

These results indicate that the Notch4-specific antibody H07-Lib3 has high thermal stability and elevated aggregation temperatures compared to the control antibodies.

Example 6. Evaluation of H07-Lib3 Polyreactivity

To further assess developability of candidate Notch4-specific antibody H07-Lib3, H07-Lib3 was further evaluated for non-specific polyreactivity.

Materials and Methods:

Polyreactivity assays. The non-specific reactivity of H07-Lib3 was evaluated towards cardiolipin, keyhole limpet hemocyanin (KLH), lipopolysaccharides (LPS), single-stranded DNA (ssDNA), double-stranded DNA (dsDNA), insulin, and bovine serum albumin (BSA). Additional therapeutic antibodies (bococizumab, efalizumab, gantenerumab, ibalizumab, lenzilumab, and panitumumab) were included in experiments for comparison. The reactivity percentage of each antibody was normalized to the highest reactivity value for each probe. Threshold for acceptable polyreactivity was set to 30% for all probes.

Results

The polyreactivity of H07-Lib3 against cardiolipin, KLH, LPS, ssDNA, dsDNA, insulin, and BSA was determined. FIGS. 6A-6G show the average reactivity percentage of H07-Lib3 and commercial antibodies towards cardiolipin, KLH, LPS, ssDNA, dsDNA, insulin, and BSA, respectively. As shown in FIGS. 6A-6G, H07-Lib3 showed lower than 30% reactivity for against each of the aforementioned antigens.

These results demonstrate that H07-Lib3 is not reactive with any of the seven assessed probes (cardiolipin, KLH, LPS, dsDNA, ssDNA, insulin, and BSA).

EQUIVALENTS

The entire disclosure of each of the patent documents and scientific articles referred to herein is incorporated by reference for all purposes.

The disclosure may be embodied in other specific forms without departing from the spirit or essential characteristics thereof. The foregoing embodiments are therefore to be considered in all respects illustrative rather than limiting the disclosure described herein. Various structural elements of the different embodiments and various disclosed method steps may be utilized in various combinations and permutations, and all such variants are to be considered forms of the disclosure. Scope of the disclosure is thus indicated by the appended claims rather than by the foregoing description, and all changes that come within the meaning and range of equivalency of the claims are intended to be embraced therein.

The invention claimed is:

1. An antibody or antigen-binding fragment thereof that binds to Notch4, comprising:
 (a) (i) a heavy chain variable domain ($V_H$) comprising complementarity-determining regions:
  CDR-H1 comprising the amino acid sequence of SEQ ID NO: 2,
  CDR-H2 comprising the amino acid sequence of SEQ ID NO: 3, and
  CDR-H3 comprising the amino acid sequence of SEQ ID NO: 4; and
 (ii) a light chain variable domain ($V_K$) comprising complementarity-determining regions:
  CDR-L1 comprising the amino acid sequence of SEQ ID NO: 6,
  CDR-L2 comprising the amino acid sequence of SEQ ID NO: 7, and
  CDR-L3 comprising the amino acid sequence of SEQ ID NO: 8;
 (b) (i) a $V_H$ comprising complementarity-determining regions:
  CDR-H1 comprising the amino acid sequence of SEQ ID NO: 10,
  CDR-H2 comprising the amino acid sequence of SEQ ID NO: 11, and
  CDR-H3 comprising the amino acid sequence of SEQ ID NO: 12; and
 (ii) a $V_K$ comprising complementarity-determining regions:
  CDR-L1 comprising the amino acid sequence of SEQ ID NO: 14,
  CDR-L2 comprising the amino acid sequence of SEQ ID NO: 15, and
  CDR-L3 comprising the amino acid sequence of SEQ ID NO: 16;
 (c) (i) a $V_H$ comprising complementarity-determining regions:
  CDR-H1 comprising the amino acid sequence of SEQ ID NO: 18,
  CDR-H2 comprising the amino acid sequence of SEQ ID NO: 19, and
  CDR-H3 comprising the amino acid sequence of SEQ ID NO: 20; and
 (ii) a $V_K$ comprising complementarity-determining regions:
  CDR-L1 comprising the amino acid sequence of SEQ ID NO: 22,
  CDR-L2 comprising the amino acid sequence of SEQ ID NO: 23, and
  CDR-L3 comprising the amino acid sequence of SEQ ID NO: 24;
 (d) (i) a $V_H$ comprising complementarity-determining regions:
  CDR-H1 comprising the amino acid sequence of SEQ ID NO: 34,
  CDR-H2 comprising the amino acid sequence of SEQ ID NO: 35, and
  CDR-H3 comprising the amino acid sequence of SEQ ID NO: 36; and
 (ii) a $V_K$ comprising complementarity-determining regions:
  CDR-L1 comprising the amino acid sequence of SEQ ID NO: 38,
  CDR-L2 comprising the amino acid sequence of SEQ ID NO: 39, and
  CDR-L3 comprising the amino acid sequence of SEQ ID NO: 40; or
 (e)) (i) a $V_H$ comprising complementarity-determining regions:
  CDR-H1 comprising the amino acid sequence of SEQ ID NO: 98,
  CDR-H2 comprising the amino acid sequence of SEQ ID NO: 99, and
  CDR-H3 comprising the amino acid sequence of SEQ ID NO: 100; and
 (ii) a $V_K$ comprising complementarity-determining regions:
  CDR-L1 comprising the amino acid sequence of SEQ ID NO: 102,
  CDR-L2 comprising the amino acid sequence of SEQ ID NO: 103, and
  CDR-L3 comprising the amino acid sequence of SEQ ID NO: 104.

2. The antibody or antigen-binding fragment thereof of claim 1, comprising:
 (i) a $V_H$ comprising complementarity-determining regions:
  CDR-H1 comprising the amino acid sequence of SEQ ID NO: 2;
  CDR-H2 comprising the amino acid sequence of SEQ ID NO: 3; and
  CDR-H3 comprising the amino acid sequence of SEQ ID NO: 4; and
 (ii) a $V_K$ comprising complementarity-determining regions:
  CDR-L1 comprising the amino acid sequence of SEQ ID NO: 6;
  CDR-L2 comprising the amino acid sequence of SEQ ID NO: 7; and
  CDR-L3 comprising the amino acid sequence of SEQ ID NO: 8.

3. The antibody or antigen binding fragment thereof of claim 2, wherein:
 the $V_H$ comprises an amino acid sequence that is at least 85% identical to that of SEQ ID NO: 1; and
 the $V_K$ comprises an amino acid sequence that is at least 85% identical to that of SEQ ID NO: 5.

4. The antibody or antigen binding fragment thereof of claim 3, wherein:

the V$_H$ comprises the amino acid sequence of SEQ ID NO: 1; and the V$_K$ comprises the amino acid sequence of SEQ ID NO: 5.

5. The antibody or antigen binding fragment thereof of claim 1, comprising:
   (i) a V$_H$ comprising complementarity-determining regions:
   CDR-H1 comprising the amino acid sequence of SEQ ID NO: 10;
   CDR-H2 comprising the amino acid sequence of SEQ ID NO: 11; and
   CDR-H3 comprising the amino acid sequence of SEQ ID NO: 12; and
   (ii) a V$_K$ comprising complementarity-determining regions:
   CDR-L1 comprising the amino acid sequence of SEQ ID NO: 14;
   CDR-L2 comprising the amino acid sequence of SEQ ID NO: 15; and
   CDR-L3 comprising the amino acid sequence of SEQ ID NO: 16.

6. The antibody or antigen binding fragment thereof of claim 5, wherein:
   the V$_H$ comprises an amino acid sequence that is at least 85% identical to that of SEQ ID NO: 9; and
   the V$_K$ comprises an amino acid sequence that is at least 85% identical to that of SEQ ID NO: 13.

7. The antibody or antigen binding fragment thereof of claim 6, wherein:
   the V$_H$ comprises the amino acid sequence of SEQ ID NO: 9; and
   the V$_K$ comprises the amino acid sequence of SEQ ID NO: 13.

8. The antibody or antigen binding fragment thereof of claim 1, comprising:
   (i) a V$_H$ comprising complementarity-determining regions:
   CDR-H1 comprising the amino acid sequence of SEQ ID NO: 18;
   CDR-H2 comprising the amino acid sequence of SEQ ID NO: 19; and
   CDR-H3 comprising the amino acid sequence of SEQ ID NO: 20; and
   (ii) a V$_K$ comprising complementarity-determining regions:
   CDR-L1 comprising the amino acid sequence of SEQ ID NO: 22;
   CDR-L2 comprising the amino acid sequence of SEQ ID NO: 23; and
   CDR-L3 comprising the amino acid sequence of SEQ ID NO: 24.

9. The antibody or antigen binding fragment thereof of claim 8, wherein:
   the V$_H$ comprises an amino acid sequence that is at least 85% identical to that of SEQ ID NO: 17; and
   the V$_K$ comprises an amino acid sequence that is at least 85% identical to that of SEQ ID NO: 21.

10. The antibody or antigen binding fragment thereof of claim 9, wherein:
    the V$_H$ comprises the amino acid sequence of SEQ ID NO: 17; and
    the V$_K$ comprises the amino acid sequence of SEQ ID NO: 21.

11. The antibody or antigen binding fragment thereof of claim 1, comprising:
    (i) a V$_H$ comprising complementarity-determining regions:
    CDR-H1 comprising the amino acid sequence of SEQ ID NO: 34;
    CDR-H2 comprising the amino acid sequence of SEQ ID NO: 35; and
    CDR-H3 comprising the amino acid sequence of SEQ ID NO: 36; and
    (ii) a V$_K$ comprising complementarity-determining regions:
    CDR-L1 comprising the amino acid sequence of SEQ ID NO: 38;
    CDR-L2 comprising the amino acid sequence of SEQ ID NO: 39; and
    CDR-L3 comprising the amino acid sequence of SEQ ID NO: 40.

12. The antibody or antigen binding fragment thereof of claim 11, wherein:
    the V$_H$ comprises an amino acid sequence that is at least 85% identical to that of SEQ ID NO: 33; and
    the V$_K$ comprises an amino acid sequence that is at least 85% identical to that of SEQ ID NO: 37.

13. The antibody or antigen binding fragment thereof of claim 12, wherein:
    the V$_H$ comprises the amino acid sequence of SEQ ID NO: 33; and
    the V$_K$ comprises the amino acid sequence of SEQ ID NO: 37.

14. The antibody or antigen binding fragment thereof of claim 1, comprising:
    (i) a V$_H$ comprising complementarity-determining regions:
    CDR-H1 comprising the amino acid sequence of SEQ ID NO: 98;
    CDR-H2 comprising the amino acid sequence of SEQ ID NO: 99; and
    CDR-H3 comprising the amino acid sequence of SEQ ID NO: 100; and
    (ii) a V$_K$ comprising complementarity-determining regions:
    CDR-L1 comprising the amino acid sequence of SEQ ID NO: 102;
    CDR-L2 comprising the amino acid sequence of SEQ ID NO: 103; and
    CDR-L3 comprising the amino acid sequence of SEQ ID NO: 104.

15. The antibody or antigen binding fragment thereof of claim 14, wherein:
    the V$_H$ comprises an amino acid sequence that is at least 85% identical to that of SEQ ID NO: 97; and
    the V$_K$ comprises an amino acid sequence that is at least 85% identical to that of SEQ ID NO: 101.

16. The antibody or antigen binding fragment thereof of claim 15, wherein:
    the V$_H$ comprises the amino acid sequence of SEQ ID NO: 97; and
    the V$_K$ comprises the amino acid sequence of SEQ ID NO: 101.

17. The antibody or antigen binding fragment thereof of claim 1, wherein the antibody is a human antibody.

18. The antibody or antigen binding fragment thereof of claim 1, comprising a human IgG4 heavy chain constant region.

19. An isolated nucleic acid encoding the heavy chain variable domain and/or light chain variable domain of an antibody or antigen-binding fragment thereof of claim 1.

20. A composition comprising an antibody or antigen-binding fragment thereof of claim 1 and a pharmaceutically acceptable carrier.

21. A method of treating or ameliorating airway inflammation in a subject, comprising the step of administering to the subject an effective amount of the antibody or antigen binding fragment thereof, wherein the antibody or antigen binding fragment comprises:
(a) (i) a heavy chain variable domain ($V_H$) comprising complementarity-determining regions:
CDR-H1 comprising the amino acid sequence of SEQ ID NO: 2,
CDR-H2 comprising the amino acid sequence of SEQ ID NO: 3, and
CDR-H3 comprising the amino acid sequence of SEQ ID NO: 4; and
(ii) a light chain variable domain ($V_K$) comprising complementarity-determining regions:
CDR-L1 comprising the amino acid sequence of SEQ ID NO: 6,
CDR-L2 comprising the amino acid sequence of SEQ ID NO: 7, and
CDR-L3 comprising the amino acid sequence of SEQ ID NO: 8;
(b) (i) a $V_H$ comprising complementarity-determining regions:
CDR-H1 comprising the amino acid sequence of SEQ ID NO: 18,
CDR-H2 comprising the amino acid sequence of SEQ ID NO: 19, and
CDR-H3 comprising the amino acid sequence of SEQ ID NO: 20; and
(ii) a $V_K$ comprising complementarity-determining regions:
CDR-L1 comprising the amino acid sequence of SEQ ID NO: 22,
CDR-L2 comprising the amino acid sequence of SEQ ID NO: 23, and
CDR-L3 comprising the amino acid sequence of SEQ ID NO: 24;
(c) (i) a $V_H$ comprising complementarity-determining regions:
CDR-H1 comprising the amino acid sequence of SEQ ID NO: 34,
CDR-H2 comprising the amino acid sequence of SEQ ID NO: 35, and
CDR-H3 comprising the amino acid sequence of SEQ ID NO: 36; and
(ii) a $V_K$ comprising complementarity-determining regions:
CDR-L1 comprising the amino acid sequence of SEQ ID NO: 38,
CDR-L2 comprising the amino acid sequence of SEQ ID NO: 39, and
CDR-L3 comprising the amino acid sequence of SEQ ID NO: 40;
or (d) (i) a $V_H$ comprising complementarity-determining regions:
CDR-H1 comprising the amino acid sequence of SEQ ID NO: 98,
CDR-H2 comprising the amino acid sequence of SEQ ID NO: 99, and
CDR-H3 comprising the amino acid sequence of SEQ ID NO: 100; and
(ii) a $V_K$ comprising complementarity-determining regions:
CDR-L1 comprising the amino acid sequence of SEQ ID NO: 102,
CDR-L2 comprising the amino acid sequence of SEQ ID NO: 103, and
CDR-L3 comprising the amino acid sequence of SEQ ID NO: 104.

22. The method of claim 21, wherein the subject is a mammal.

23. The method of claim 21, wherein the subject is a human.

24. The method of claim 23, wherein the subject is diagnosed as having or at risk of having an airway inflammation-associated disorder selected from the group consisting of asthma, chronic obstructive pulmonary disorder (COPD), cystic fibrosis (CF), and bronchopulmonary dysplasia (BPD).

25. The method of claim 21, wherein the step of administering comprises intravenous, intramuscular, or subcutaneous administration.

* * * * *

SEQUENCE LISTING

```
Sequence total quantity: 147
SEQ ID NO: 1              moltype = AA  length = 121
FEATURE                   Location/Qualifiers
source                    1..121
                          mol_type = protein
                          organism = synthetic construct
SEQUENCE: 1
EVQLVESGGG LVQPGRSLRL SCAASEFSFS RFDMHWVRQA PGKGLEWVSA ISSSGSYKDY   60
ADSVEGRFTI SRDNAKNSLY LQMNSLRAED TAVYYCAREA YGDYGKPFDY WGQGTLVTVS  120
S                                                                 121

SEQ ID NO: 2              moltype = AA  length = 8
FEATURE                   Location/Qualifiers
```

```
                                            -continued source                     1..8
                           mol_type = protein
                           organism = synthetic construct
SEQUENCE: 2
EFSFSRFD                                                                    8

SEQ ID NO: 3               moltype = AA   length = 8
FEATURE                    Location/Qualifiers
source                     1..8
                           mol_type = protein
                           organism = synthetic construct
SEQUENCE: 3
ISSSGSYK                                                                    8

SEQ ID NO: 4               moltype = AA   length = 14
FEATURE                    Location/Qualifiers
source                     1..14
                           mol_type = protein
                           organism = synthetic construct
SEQUENCE: 4
AREAYGDYGK PFDY                                                            14

SEQ ID NO: 5               moltype = AA   length = 104
FEATURE                    Location/Qualifiers
source                     1..104
                           mol_type = protein
                           organism = synthetic construct
SEQUENCE: 5
DIQMTQSPSS LSASVGDRVT ITCRASQSIS RNLAWYQQKP GKAPKLLIYA GSTLQRGVPS          60
RFSGSGSGTD FTLTISSLQP EDVATYYCLQ ANMYPLTFGG GTKV                          104

SEQ ID NO: 6               moltype = AA   length = 6
FEATURE                    Location/Qualifiers
source                     1..6
                           mol_type = protein
                           organism = synthetic construct
SEQUENCE: 6
QSISRN                                                                      6

SEQ ID NO: 7               moltype = AA   length = 7
FEATURE                    Location/Qualifiers
source                     1..7
                           mol_type = protein
                           organism = synthetic construct
SEQUENCE: 7
AGSTLQR                                                                     7

SEQ ID NO: 8               moltype = AA   length = 9
FEATURE                    Location/Qualifiers
source                     1..9
                           mol_type = protein
                           organism = synthetic construct
SEQUENCE: 8
LQANMYPLT                                                                   9

SEQ ID NO: 9               moltype = AA   length = 121
FEATURE                    Location/Qualifiers
source                     1..121
                           mol_type = protein
                           organism = synthetic construct
SEQUENCE: 9
EVQLVESGGG LVQPGGSLRL SCAASGLPFS SYGMSWVRQA PGKGLELVAS IGTSGTRTYY          60
PDSVKGRFTI SRDNAKNSLY LQMNSLRAED TAVYYCARLG EGSGWSYFDY WGQGTLVTVS         120
S                                                                         121

SEQ ID NO: 10              moltype = AA   length = 8
FEATURE                    Location/Qualifiers
source                     1..8
                           mol_type = protein
                           organism = synthetic construct
SEQUENCE: 10
GLPFSSYG                                                                    8

SEQ ID NO: 11              moltype = AA   length = 8
FEATURE                    Location/Qualifiers
source                     1..8
                           mol_type = protein
                           organism = synthetic construct
SEQUENCE: 11
```

```
IGTSGTRT                                                               8

SEQ ID NO: 12           moltype = AA  length = 14
FEATURE                 Location/Qualifiers
source                  1..14
                        mol_type = protein
                        organism = synthetic construct
SEQUENCE: 12
ARLGEGSGWS YFDY                                                       14

SEQ ID NO: 13           moltype = AA  length = 112
FEATURE                 Location/Qualifiers
source                  1..112
                        mol_type = protein
                        organism = synthetic construct
SEQUENCE: 13
DIVMTQSPLS LPVTPGEPAS ISCRSSQSLL HSTGYNYLHW YLQKPGQSPQ LLIYSGSYRA      60
SGVPDRFSGS GSGTDFTLKI SRVEAEDVGV YYCQQGYSTP HTFGGGTKVE IK             112

SEQ ID NO: 14           moltype = AA  length = 11
FEATURE                 Location/Qualifiers
source                  1..11
                        mol_type = protein
                        organism = synthetic construct
SEQUENCE: 14
QSLLHSTGYN Y                                                          11

SEQ ID NO: 15           moltype = AA  length = 7
FEATURE                 Location/Qualifiers
source                  1..7
                        mol_type = protein
                        organism = synthetic construct
SEQUENCE: 15
SGSYRAS                                                                7

SEQ ID NO: 16           moltype = AA  length = 9
FEATURE                 Location/Qualifiers
source                  1..9
                        mol_type = protein
                        organism = synthetic construct
SEQUENCE: 16
QQGYSTPHT                                                              9

SEQ ID NO: 17           moltype = AA  length = 117
FEATURE                 Location/Qualifiers
source                  1..117
                        mol_type = protein
                        organism = synthetic construct
SEQUENCE: 17
EVQLVQSGAE VKKPGASVKV SCKASGYTFA TYPISWVRQA PGQGLEWMGG MNPTTGDTIY      60
AQKLQGRGTM TTDPSTSTAY MELRSLRSDD TAVYYCARGD RAWFDPWGQG TLVTVSS        117

SEQ ID NO: 18           moltype = AA  length = 8
FEATURE                 Location/Qualifiers
source                  1..8
                        mol_type = protein
                        organism = synthetic construct
SEQUENCE: 18
GYTFATYP                                                               8

SEQ ID NO: 19           moltype = AA  length = 8
FEATURE                 Location/Qualifiers
source                  1..8
                        mol_type = protein
                        organism = synthetic construct
SEQUENCE: 19
MNPTTGDT                                                               8

SEQ ID NO: 20           moltype = AA  length = 10
FEATURE                 Location/Qualifiers
source                  1..10
                        mol_type = protein
                        organism = synthetic construct
SEQUENCE: 20
ARGDRAWFDP                                                            10

SEQ ID NO: 21           moltype = AA  length = 109
FEATURE                 Location/Qualifiers
source                  1..109
```

```
                          mol_type = protein
                          organism = synthetic construct
SEQUENCE: 21
ESALTQPASV SGSPGQSITI SCTGTGSNIG AGYGVSWYQQ HPGKAPKLMI YANINRPPGV    60
SNRFSGSKSG NTASLTISGL QAEDEADYYC SSYTSSSWMF GGGTKLTVL               109

SEQ ID NO: 22             moltype = AA   length = 9
FEATURE                   Location/Qualifiers
source                    1..9
                          mol_type = protein
                          organism = synthetic construct
SEQUENCE: 22
GSNIGAGYG                                                             9

SEQ ID NO: 23             moltype = AA   length = 7
FEATURE                   Location/Qualifiers
source                    1..7
                          mol_type = protein
                          organism = synthetic construct
SEQUENCE: 23
ANINRPP                                                               7

SEQ ID NO: 24             moltype = AA   length = 9
FEATURE                   Location/Qualifiers
source                    1..9
                          mol_type = protein
                          organism = synthetic construct
SEQUENCE: 24
SSYTSSSWM                                                             9

SEQ ID NO: 25             moltype = AA   length = 121
FEATURE                   Location/Qualifiers
source                    1..121
                          mol_type = protein
                          organism = synthetic construct
SEQUENCE: 25
EVQLVESGGG LVQPGGSLRL SCAASGFSFG TYSMSWVRQA PGKGLELVAS IDTAGTPYYP    60
DSVKGRFTIS RDNAKNSLYL QMNSLRAEDT AVYYCARSYS GYDPYDAFDI WGQGTMVTVS   120
S                                                                   121

SEQ ID NO: 26             moltype = AA   length = 8
FEATURE                   Location/Qualifiers
source                    1..8
                          mol_type = protein
                          organism = synthetic construct
SEQUENCE: 26
GFSFGTYS                                                              8

SEQ ID NO: 27             moltype = AA   length = 7
FEATURE                   Location/Qualifiers
source                    1..7
                          mol_type = protein
                          organism = synthetic construct
SEQUENCE: 27
IDTAGTP                                                               7

SEQ ID NO: 28             moltype = AA   length = 15
FEATURE                   Location/Qualifiers
source                    1..15
                          mol_type = protein
                          organism = synthetic construct
SEQUENCE: 28
ARSYSGYDPY DAFDI                                                     15

SEQ ID NO: 29             moltype = AA   length = 112
FEATURE                   Location/Qualifiers
source                    1..112
                          mol_type = protein
                          organism = synthetic construct
SEQUENCE: 29
DIVMTQSPLS LPVTPGEPAS ISCRSSRSLV HGSGDNYLHW YLQKPGQSPQ LLIYDASNRF    60
SGVPDRFSGS GSGTDFTLKI SRVEAEDVGV YYCAQTLQIP LTFGGGTKVE IK           112

SEQ ID NO: 30             moltype = AA   length = 11
FEATURE                   Location/Qualifiers
source                    1..11
                          mol_type = protein
                          organism = synthetic construct
SEQUENCE: 30
```

-continued

```
RSLVHGSGDN Y                                                          11

SEQ ID NO: 32         moltype = AA   length = 7
FEATURE               Location/Qualifiers
source                1..7
                      mol_type = protein
                      organism = synthetic construct
SEQUENCE: 31
DASNRFS                                                               7

SEQ ID NO: 32         moltype = AA   length = 9
FEATURE               Location/Qualifiers
source                1..9
                      mol_type = protein
                      organism = synthetic construct
SEQUENCE: 32
AQTLQIPLT                                                             9

SEQ ID NO: 33         moltype = AA   length = 120
FEATURE               Location/Qualifiers
source                1..120
                      mol_type = protein
                      organism = synthetic construct
SEQUENCE: 33
EVQLVESGGG LVQPGGSLRL SCAASGLPFS SYAMSWVRQA PGKGLELVAS IGTAGDAYYP     60
DSVKGRFTIS RDNAKNSLYL QMNSLRAEDT AVYYCARVGP FWQGFAFDIW GQGTMVTVSS    120

SEQ ID NO: 34         moltype = AA   length = 8
FEATURE               Location/Qualifiers
source                1..8
                      mol_type = protein
                      organism = synthetic construct
SEQUENCE: 34
GLPFSSYA                                                              8

SEQ ID NO: 35         moltype = AA   length = 7
FEATURE               Location/Qualifiers
source                1..7
                      mol_type = protein
                      organism = synthetic construct
SEQUENCE: 35
IGTAGDA                                                               7

SEQ ID NO: 36         moltype = AA   length = 14
FEATURE               Location/Qualifiers
source                1..14
                      mol_type = protein
                      organism = synthetic construct
SEQUENCE: 36
ARVGPFWQGF AFDI                                                      14

SEQ ID NO: 37         moltype = AA   length = 112
FEATURE               Location/Qualifiers
source                1..112
                      mol_type = protein
                      organism = synthetic construct
SEQUENCE: 37
DIVMTQSPLS LPVTPGEPAS ISCRSSQSLL HSSGHNYLHW YLQKPGQSPQ LLIYMTYNRA     60
SGVPDRFSGS GSGTDFTLKI SRVEAEDVGV YYCLQTTHWP HTFGGGTKVE IK            112

SEQ ID NO: 38         moltype = AA   length = 11
FEATURE               Location/Qualifiers
source                1..11
                      mol_type = protein
                      organism = synthetic construct
SEQUENCE: 38
QSLLHSSGHN Y                                                         11

SEQ ID NO: 39         moltype = AA   length = 7
FEATURE               Location/Qualifiers
source                1..7
                      mol_type = protein
                      organism = synthetic construct
SEQUENCE: 39
MTYNRAS                                                               7

SEQ ID NO: 40         moltype = AA   length = 9
FEATURE               Location/Qualifiers
source                1..9
```

```
                            mol_type = protein
                            organism = synthetic construct
SEQUENCE: 40
LQTTHWPHT                                                                  9

SEQ ID NO: 41           moltype = AA  length = 126
FEATURE                 Location/Qualifiers
source                  1..126
                        mol_type = protein
                        organism = synthetic construct
SEQUENCE: 41
QVQLVQSGAE VKKPGASVKV SCKVSGYPFS NYAIHWVRQA PGKGLEWMGG ISPYTGKTIY        60
AQKFQGRVTM TEDTSTDTAY MELSSLKSED TAVYYCAFSR YYYDSSGYHG DAFDIWGQGT       120
MVTVSS                                                                  126

SEQ ID NO: 42           moltype = AA  length = 8
FEATURE                 Location/Qualifiers
source                  1..8
                        mol_type = protein
                        organism = synthetic construct
SEQUENCE: 42
GYPFSNYA                                                                   8

SEQ ID NO: 43           moltype = AA  length = 8
FEATURE                 Location/Qualifiers
source                  1..8
                        mol_type = protein
                        organism = synthetic construct
SEQUENCE: 43
ISPYTGKT                                                                   8

SEQ ID NO: 44           moltype = AA  length = 19
FEATURE                 Location/Qualifiers
source                  1..19
                        mol_type = protein
                        organism = synthetic construct
SEQUENCE: 44
AFSRYYYDSS GYHGDAFDI                                                      19

SEQ ID NO: 45           moltype = AA  length = 106
FEATURE                 Location/Qualifiers
source                  1..106
                        mol_type = protein
                        organism = synthetic construct
SEQUENCE: 45
DIQMTQSPSS VSASVGDRVT ITCRASQGIS NHLAWYQQKP GKAPKLLIYD ASNRATGVPS        60
RFSGSGSGTD FTLTISSLQP EDFANYYCQQ SFTIPSFGGG TKVEIK                      106

SEQ ID NO: 46           moltype = AA  length = 6
FEATURE                 Location/Qualifiers
source                  1..6
                        mol_type = protein
                        organism = synthetic construct
SEQUENCE: 46
QGISNH                                                                     6

SEQ ID NO: 47           moltype = AA  length = 7
FEATURE                 Location/Qualifiers
source                  1..7
                        mol_type = protein
                        organism = synthetic construct
SEQUENCE: 47
DASNRAT                                                                    7

SEQ ID NO: 48           moltype = AA  length = 8
FEATURE                 Location/Qualifiers
source                  1..8
                        mol_type = protein
                        organism = synthetic construct
SEQUENCE: 48
QQSFTIPS                                                                   8

SEQ ID NO: 49           moltype = AA  length = 116
FEATURE                 Location/Qualifiers
source                  1..116
                        mol_type = protein
                        organism = synthetic construct
SEQUENCE: 49
QVQLVESGGG LVQPGGSLRL SCAASGLTFS GSAMSWVRQA PGKGLELVAS ITGSGTRTYY        60
```

```
PDSVKGRFTI SRDNAKNSLY LQMNSLRAED TAVYYCARGL HAFDIWGQGT MVTVSS          116

SEQ ID NO: 50              moltype = AA   length = 8
FEATURE                    Location/Qualifiers
source                     1..8
                           mol_type = protein
                           organism = synthetic construct
SEQUENCE: 50
GLTFSGSA                                                               8

SEQ ID NO: 51              moltype = AA   length = 8
FEATURE                    Location/Qualifiers
source                     1..8
                           mol_type = protein
                           organism = synthetic construct
SEQUENCE: 51
ITGSGTRT                                                               8

SEQ ID NO: 52              moltype = AA   length = 9
FEATURE                    Location/Qualifiers
source                     1..9
                           mol_type = protein
                           organism = synthetic construct
SEQUENCE: 52
ARGLHAFDI                                                              9

SEQ ID NO: 53              moltype = AA   length = 112
FEATURE                    Location/Qualifiers
source                     1..112
                           mol_type = protein
                           organism = synthetic construct
SEQUENCE: 53
DIVMTQSPLS LPVTPGEPAS ISCRSSQSLL SSYGYHNLHW YLQKPGQSPQ LLIYMGYNRA      60
SGVPDRFSGS GSGTDFTLKI SRVEAEDVGV YYCMQGMHLP ITFGGGTKVE IK              112

SEQ ID NO: 54              moltype = AA   length = 11
FEATURE                    Location/Qualifiers
source                     1..11
                           mol_type = protein
                           organism = synthetic construct
SEQUENCE: 54
QSLLSSYGYH N                                                           11

SEQ ID NO: 55              moltype = AA   length = 7
FEATURE                    Location/Qualifiers
source                     1..7
                           mol_type = protein
                           organism = synthetic construct
SEQUENCE: 55
MGYNRAS                                                                7

SEQ ID NO: 56              moltype = AA   length = 9
FEATURE                    Location/Qualifiers
source                     1..9
                           mol_type = protein
                           organism = synthetic construct
SEQUENCE: 56
MQGMHLPIT                                                              9

SEQ ID NO: 57              moltype = AA   length = 115
FEATURE                    Location/Qualifiers
source                     1..115
                           mol_type = protein
                           organism = synthetic construct
SEQUENCE: 57
QVQLVQSGAE VKKPGASVKV SCKVSGYTLT KSSIHWVRQA PGKGLEWMGG INPSAGTRIY      60
AQKFQGRVTM TEDTSTDTAY MELSSLKSED TAVYYCVRGS NPNVWGKGTT VTVSS           115

SEQ ID NO: 58              moltype = AA   length = 8
FEATURE                    Location/Qualifiers
source                     1..8
                           mol_type = protein
                           organism = synthetic construct
SEQUENCE: 58
GYTLTKSS                                                               8

SEQ ID NO: 59              moltype = AA   length = 8
FEATURE                    Location/Qualifiers
source                     1..8
```

```
                              mol_type = protein
                              organism = synthetic construct
SEQUENCE: 59
INPSAGTR                                                                        8

SEQ ID NO: 60            moltype = AA   length = 8
FEATURE                  Location/Qualifiers
source                   1..8
                         mol_type = protein
                         organism = synthetic construct
SEQUENCE: 60
VRGSNPNV                                                                        8

SEQ ID NO: 61            moltype = AA   length = 107
FEATURE                  Location/Qualifiers
source                   1..107
                         mol_type = protein
                         organism = synthetic construct
SEQUENCE: 61
DIQMTQSPSS VSASVGDRVT ITCRASQTIG NYLAWYQQKP GKAPKLLIYK ASTLASGVPS              60
RFSGSGSGTD FTLTISSLQP EDFANYYCQQ YNFYPRTFGG GTKVEIK                           107

SEQ ID NO: 62            moltype = AA   length = 6
FEATURE                  Location/Qualifiers
source                   1..6
                         mol_type = protein
                         organism = synthetic construct
SEQUENCE: 62
QTIGNY                                                                          6

SEQ ID NO: 63            moltype = AA   length = 7
FEATURE                  Location/Qualifiers
source                   1..7
                         mol_type = protein
                         organism = synthetic construct
SEQUENCE: 63
KASTLAS                                                                         7

SEQ ID NO: 64            moltype = AA   length = 9
FEATURE                  Location/Qualifiers
source                   1..9
                         mol_type = protein
                         organism = synthetic construct
SEQUENCE: 64
QQYNFYPRT                                                                       9

SEQ ID NO: 65            moltype = AA   length = 127
FEATURE                  Location/Qualifiers
source                   1..127
                         mol_type = protein
                         organism = synthetic construct
SEQUENCE: 65
EVQLVQSGAE VKKPGASVKV SCKASGYSFT KSGIHWVRQA PGQGLEWMGW INPRTGNINY              60
AQKLQGRGTM TTDPSTSTAY MELRSLRSDD TAVYYCARTH LGSSSSPPGY YYGMDVWGQG             120
TTVTVSS                                                                       127

SEQ ID NO: 66            moltype = AA   length = 8
FEATURE                  Location/Qualifiers
source                   1..8
                         mol_type = protein
                         organism = synthetic construct
SEQUENCE: 66
GYSFTKSG                                                                        8

SEQ ID NO: 67            moltype = AA   length = 8
FEATURE                  Location/Qualifiers
source                   1..8
                         mol_type = protein
                         organism = synthetic construct
SEQUENCE: 67
INPRTGNI                                                                        8

SEQ ID NO: 68            moltype = AA   length = 20
FEATURE                  Location/Qualifiers
source                   1..20
                         mol_type = protein
                         organism = synthetic construct
SEQUENCE: 68
ARTHLGSSSS PPGYYYGMDV                                                          20
```

```
SEQ ID NO: 69            moltype = AA  length = 106
FEATURE                  Location/Qualifiers
source                   1..106
                         mol_type = protein
                         organism = synthetic construct
SEQUENCE: 69
ESALTQPASV SGSPGQSITI SCTGTNIGAK AVSWYQQHPG KAPKLMIYAE NKRPSGVSNR   60
FSGSKSGNTA SLTISGLQAE DEADYYCQAW DNRAILFGGG TKLTVL                 106

SEQ ID NO: 70            moltype = AA  length = 6
FEATURE                  Location/Qualifiers
source                   1..6
                         mol_type = protein
                         organism = synthetic construct
SEQUENCE: 70
NIGAKA                                                              6

SEQ ID NO: 71            moltype = AA  length = 7
FEATURE                  Location/Qualifiers
source                   1..7
                         mol_type = protein
                         organism = synthetic construct
SEQUENCE: 71
AENKRPS                                                             7

SEQ ID NO: 72            moltype = AA  length = 9
FEATURE                  Location/Qualifiers
source                   1..9
                         mol_type = protein
                         organism = synthetic construct
SEQUENCE: 72
QAWDNRAIL                                                           9

SEQ ID NO: 73            moltype = AA  length = 127
FEATURE                  Location/Qualifiers
source                   1..127
                         mol_type = protein
                         organism = synthetic construct
SEQUENCE: 73
EVQLVQSGAE VKKPGASVKV SCKASGFPFS TSAISWVRQA PGQGLEWMGW MDPATGQTNY   60
AQKLQGRGTM TTDPSTSTAY MELRSLRSDD TAVYYCARAL RYCSGGRCQG FHGMDVWGQG   120
TTVTVSS                                                             127

SEQ ID NO: 74            moltype = AA  length = 8
FEATURE                  Location/Qualifiers
source                   1..8
                         mol_type = protein
                         organism = synthetic construct
SEQUENCE: 74
GFPFSTSA                                                            8

SEQ ID NO: 75            moltype = AA  length = 8
FEATURE                  Location/Qualifiers
source                   1..8
                         mol_type = protein
                         organism = synthetic construct
SEQUENCE: 75
MDPATGQT                                                            8

SEQ ID NO: 76            moltype = AA  length = 20
FEATURE                  Location/Qualifiers
source                   1..20
                         mol_type = protein
                         organism = synthetic construct
SEQUENCE: 76
ARALRYCSGG RCQGFHGMDV                                               20

SEQ ID NO: 77            moltype = AA  length = 106
FEATURE                  Location/Qualifiers
source                   1..106
                         mol_type = protein
                         organism = synthetic construct
SEQUENCE: 77
ESALTQPASV SGSPGQSITI SCTGTNIAAK SVSWYQQHPG KAPKLMIYAN INRPPGVSNR   60
FSGSKSGNTA SLTISGLQAE DEADYYCSSY TSSSWMFGGG TKLTVL                 106

SEQ ID NO: 78            moltype = AA  length = 6
FEATURE                  Location/Qualifiers
```

```
source                         1..6
                               mol_type = protein
                               organism = synthetic construct
SEQUENCE: 78
NIAAKS                                                                    6

SEQ ID NO: 79                  moltype = AA   length = 7
FEATURE                        Location/Qualifiers
source                         1..7
                               mol_type = protein
                               organism = synthetic construct
SEQUENCE: 79
ANINRPP                                                                   7

SEQ ID NO: 80                  moltype = AA   length = 9
FEATURE                        Location/Qualifiers
source                         1..9
                               mol_type = protein
                               organism = synthetic construct
SEQUENCE: 80
SSYTSSSWM                                                                 9

SEQ ID NO: 81                  moltype = AA   length = 130
FEATURE                        Location/Qualifiers
source                         1..130
                               mol_type = protein
                               organism = synthetic construct
SEQUENCE: 81
EVQLVQSGAE VKKPGASVKV SCKASGYTFS DHYISWVRQA PGQGLEWMGW MNPTSGHTNY         60
AQKLQGRGTM TTDPSTSTAY MELRSLRSDD TAVYYCARVS GRWLPAVDGH YYYYYGMDVW        120
GQGTTVTVSS                                                              130

SEQ ID NO: 82                  moltype = AA   length = 8
FEATURE                        Location/Qualifiers
source                         1..8
                               mol_type = protein
                               organism = synthetic construct
SEQUENCE: 82
GYTFSDHY                                                                  8

SEQ ID NO: 83                  moltype = AA   length = 8
FEATURE                        Location/Qualifiers
source                         1..8
                               mol_type = protein
                               organism = synthetic construct
SEQUENCE: 83
MNPTSGHT                                                                  8

SEQ ID NO: 84                  moltype = AA   length = 23
FEATURE                        Location/Qualifiers
source                         1..23
                               mol_type = protein
                               organism = synthetic construct
SEQUENCE: 84
ARVSGRWLPA VDGHYYYYYG MDV                                                23

SEQ ID NO: 85                  moltype = AA   length = 109
FEATURE                        Location/Qualifiers
source                         1..109
                               mol_type = protein
                               organism = synthetic construct
SEQUENCE: 85
ESALTQPASV SGSPGQSITI SCTGTGSNIG AGYGVSWYQQ HPGKAPKLMI YANINRPPGV         60
SNRFSGSKSG NTASLTISGL QAEDEADYYC SSYTSSSWMF GGGTKLTVL                   109

SEQ ID NO: 86                  moltype = AA   length = 9
FEATURE                        Location/Qualifiers
source                         1..9
                               mol_type = protein
                               organism = synthetic construct
SEQUENCE: 86
GSNIGAGYG                                                                 9

SEQ ID NO: 87                  moltype = AA   length = 7
FEATURE                        Location/Qualifiers
source                         1..7
                               mol_type = protein
                               organism = synthetic construct
SEQUENCE: 87
```

-continued

```
ANINRPP                                                                 7

SEQ ID NO: 88          moltype = AA  length = 9
FEATURE                Location/Qualifiers
source                 1..9
                       mol_type = protein
                       organism = synthetic construct
SEQUENCE: 88
SSYTSSSWM                                                               9

SEQ ID NO: 89          moltype = AA  length = 114
FEATURE                Location/Qualifiers
source                 1..114
                       mol_type = protein
                       organism = synthetic construct
SEQUENCE: 89
QVQLVQSGAE VKKPGASVKV SCKVSGYAFT TYNIHWVRQA PGKGLEWMGG INPSGSTSIY        60
AQKFQGRVTM TEDTSTDTAY MELSSLKSED TAVYYCARGP VDVWGQGTTV TVSS             114

SEQ ID NO: 90          moltype = AA  length = 8
FEATURE                Location/Qualifiers
source                 1..8
                       mol_type = protein
                       organism = synthetic construct
SEQUENCE: 90
GYAFTTYN                                                                8

SEQ ID NO: 91          moltype = AA  length = 8
FEATURE                Location/Qualifiers
source                 1..8
                       mol_type = protein
                       organism = synthetic construct
SEQUENCE: 91
INPSGSTS                                                                8

SEQ ID NO: 92          moltype = AA  length = 8
FEATURE                Location/Qualifiers
source                 1..8
                       mol_type = protein
                       organism = synthetic construct
SEQUENCE: 92
ARGIPVDV                                                                8

SEQ ID NO: 93          moltype = AA  length = 107
FEATURE                Location/Qualifiers
source                 1..107
                       mol_type = protein
                       organism = synthetic construct
SEQUENCE: 93
DIQMTQSPSS VSASVGDRVT ITCRASRDID NYLAWYQQKP GKAPKLLIYG KDQRASGVPS        60
RFSGSGSGTD FTLTISSLQP EDFANYYCQQ YRTYPWTFGG GTKVEIK                     107

SEQ ID NO: 94          moltype = AA  length = 6
FEATURE                Location/Qualifiers
source                 1..6
                       mol_type = protein
                       organism = synthetic construct
SEQUENCE: 94
RDIDNY                                                                  6

SEQ ID NO: 95          moltype = AA  length = 7
FEATURE                Location/Qualifiers
source                 1..7
                       mol_type = protein
                       organism = synthetic construct
SEQUENCE: 95
GKDQRAS                                                                 7

SEQ ID NO: 96          moltype = AA  length = 9
FEATURE                Location/Qualifiers
source                 1..9
                       mol_type = protein
                       organism = synthetic construct
SEQUENCE: 96
QQYRTYPWT                                                               9

SEQ ID NO: 97          moltype = AA  length = 119
FEATURE                Location/Qualifiers
source                 1..119
```

```
                        mol_type = protein
                        organism = synthetic construct
SEQUENCE: 97
EVQLVESGGG LVQPGRSLRL SCAASGFSFS DYHMHWVRQA PGKGLEWVGA ISGSAYTTDY    60
ADSVEGRFTI SRDNAKNSLY LQMNSLRAED TAVYYCARDD YNKDGFDPWG QGTLVTVSS    119

SEQ ID NO: 98           moltype = AA   length = 8
FEATURE                 Location/Qualifiers
source                  1..8
                        mol_type = protein
                        organism = synthetic construct
SEQUENCE: 98
GFSFSDYH                                                              8

SEQ ID NO: 99           moltype = AA   length = 8
FEATURE                 Location/Qualifiers
source                  1..8
                        mol_type = protein
                        organism = synthetic construct
SEQUENCE: 99
ISGSAYTT                                                              8

SEQ ID NO: 100          moltype = AA   length = 12
FEATURE                 Location/Qualifiers
source                  1..12
                        mol_type = protein
                        organism = synthetic construct
SEQUENCE: 100
ARDDYNKDGF DP                                                        12

SEQ ID NO: 101          moltype = AA   length = 107
FEATURE                 Location/Qualifiers
source                  1..107
                        mol_type = protein
                        organism = synthetic construct
SEQUENCE: 101
DIQMTQSPSS LSASVGDRVT ITCRASQSIY SYLAWYQQKP GKAPKLLIYD ASRLQSGVPS    60
RFSGSGSGTD FTLTISSLQP EDVATYYCQQ GYRSPITFGG GTKVEIK                 107

SEQ ID NO: 102          moltype = AA   length = 6
FEATURE                 Location/Qualifiers
source                  1..6
                        mol_type = protein
                        organism = synthetic construct
SEQUENCE: 102
QSIYSY                                                                6

SEQ ID NO: 103          moltype = AA   length = 7
FEATURE                 Location/Qualifiers
source                  1..7
                        mol_type = protein
                        organism = synthetic construct
SEQUENCE: 103
DASRLQS                                                               7

SEQ ID NO: 104          moltype = AA   length = 9
FEATURE                 Location/Qualifiers
source                  1..9
                        mol_type = protein
                        organism = synthetic construct
SEQUENCE: 104
QQGYRSPIT                                                             9

SEQ ID NO: 105          moltype = AA   length = 119
FEATURE                 Location/Qualifiers
source                  1..119
                        mol_type = protein
                        organism = synthetic construct
SEQUENCE: 105
EVQLVESGGG LVQPGGSLRL SCAASGFTLD NYVMSWVRQA PGKGLELVAS ISGSSADTYY    60
PDSVKGRFTI SRDNAKNSLY LQMNSLRAED TAVYYCAKGI AAGYGMDVWG QGTTVTVSS    119

SEQ ID NO: 106          moltype = AA   length = 8
FEATURE                 Location/Qualifiers
source                  1..8
                        mol_type = protein
                        organism = synthetic construct
SEQUENCE: 106
GFTLDNYV                                                              8
```

```
SEQ ID NO: 107         moltype = AA  length = 8
FEATURE                Location/Qualifiers
source                 1..8
                       mol_type = protein
                       organism = synthetic construct
SEQUENCE: 107
ISGSSADT                                                              8

SEQ ID NO: 108         moltype = AA  length = 12
FEATURE                Location/Qualifiers
source                 1..12
                       mol_type = protein
                       organism = synthetic construct
SEQUENCE: 108
AKGIAAGYGM DV                                                         12

SEQ ID NO: 109         moltype = AA  length = 111
FEATURE                Location/Qualifiers
source                 1..111
                       mol_type = protein
                       organism = synthetic construct
SEQUENCE: 109
DIVMTQSPLS LPVTPGEPAS ISCRSSQSLL HSSGYTYLHW YLQKPGQSPQ LLIYATSYRA      60
PGVPDRFSGS GSGTDFTLKI SRVEAEDVGV YYCMQATHPY TFGGGTKVEI K               111

SEQ ID NO: 110         moltype = AA  length = 11
FEATURE                Location/Qualifiers
source                 1..11
                       mol_type = protein
                       organism = synthetic construct
SEQUENCE: 110
QSLLHSSGYT Y                                                          11

SEQ ID NO: 111         moltype = AA  length = 7
FEATURE                Location/Qualifiers
source                 1..7
                       mol_type = protein
                       organism = synthetic construct
SEQUENCE: 111
ATSYRAP                                                               7

SEQ ID NO: 112         moltype = AA  length = 8
FEATURE                Location/Qualifiers
source                 1..8
                       mol_type = protein
                       organism = synthetic construct
SEQUENCE: 112
MQATHPYT                                                              8

SEQ ID NO: 113         moltype = AA  length = 132
FEATURE                Location/Qualifiers
source                 1..132
                       mol_type = protein
                       organism = synthetic construct
SEQUENCE: 113
QVQLVQSGAE VKKPGASVKV SCKVSGYTFT DLPIHWVRQA PGKGLEWMGG INPHSGDAIY      60
AQKFQGRVTM TEDTSTDTAY MELSSLKSED TAVYYCTTVI AVAGSNDSRP CGRSYLCVLD      120
YWGQGTLVTV SS                                                         132

SEQ ID NO: 114         moltype = AA  length = 8
FEATURE                Location/Qualifiers
source                 1..8
                       mol_type = protein
                       organism = synthetic construct
SEQUENCE: 114
GYTFTDLP                                                              8

SEQ ID NO: 115         moltype = AA  length = 8
FEATURE                Location/Qualifiers
source                 1..8
                       mol_type = protein
                       organism = synthetic construct
SEQUENCE: 115
INPHSGDA                                                              8

SEQ ID NO: 116         moltype = AA  length = 25
FEATURE                Location/Qualifiers
source                 1..25
```

```
                              mol_type = protein
                              organism = synthetic construct
SEQUENCE: 116
TTVIAVAGSN DSRPCGRSYL CVLDY                                         25

SEQ ID NO: 117        moltype = AA  length = 107
FEATURE               Location/Qualifiers
source                1..107
                      mol_type = protein
                      organism = synthetic construct
SEQUENCE: 117
DIQMTQSPSS VSASVGDRVT ITCNASQGIG HSLAWYQQKP GKAPKLLIYG ATSRATGVPS    60
RFSGSGSGTD FTLTISSLQP EDFANYYCLQ DYIYPFTFGG GTKVEIK                 107

SEQ ID NO: 118        moltype = AA  length = 6
FEATURE               Location/Qualifiers
source                1..6
                      mol_type = protein
                      organism = unidentified
SEQUENCE: 118
QGIGHS                                                               6

SEQ ID NO: 119        moltype = AA  length = 7
FEATURE               Location/Qualifiers
source                1..7
                      mol_type = protein
                      organism = synthetic construct
SEQUENCE: 119
GATSRAT                                                              7

SEQ ID NO: 120        moltype = AA  length = 9
FEATURE               Location/Qualifiers
source                1..9
                      mol_type = protein
                      organism = synthetic construct
SEQUENCE: 120
LQDYIYPFT                                                            9

SEQ ID NO: 121        moltype = AA  length = 116
FEATURE               Location/Qualifiers
source                1..116
                      mol_type = protein
                      organism = synthetic construct
SEQUENCE: 121
QVQLVQSGAE VKKPGASVKV SCKVSRGTFS TYAIHWVRQA PGKGLEWMGG INAATGYTIY    60
AQKFQGRVTM TEDTSTDTAY MELSSLKSED TAVYYCVRSV GSIEYWGQGT LVTVSS       116

SEQ ID NO: 122        moltype = AA  length = 8
FEATURE               Location/Qualifiers
source                1..8
                      mol_type = protein
                      organism = synthetic construct
SEQUENCE: 122
RGTFSTYA                                                             8

SEQ ID NO: 123        moltype = AA  length = 8
FEATURE               Location/Qualifiers
source                1..8
                      mol_type = protein
                      organism = synthetic construct
SEQUENCE: 123
INAATGYT                                                             8

SEQ ID NO: 124        moltype = AA  length = 9
FEATURE               Location/Qualifiers
source                1..9
                      mol_type = protein
                      organism = synthetic construct
SEQUENCE: 124
VRSVGSIEY                                                            9

SEQ ID NO: 125        moltype = AA  length = 106
FEATURE               Location/Qualifiers
source                1..106
                      mol_type = protein
                      organism = synthetic construct
SEQUENCE: 125
DIQMTQSPSS VSASVGDRVT ITCRASQGIS NHLAWYQQKP GKAPKLLIYG ASSRQSGVPS    60
RFSGSGSGTD FTLTISSLQP EDFANYYCLH DRYPYTFGGG TKVEIK                  106
```

```
SEQ ID NO: 126          moltype = AA  length = 6
FEATURE                 Location/Qualifiers
source                  1..6
                        mol_type = protein
                        organism = synthetic construct
SEQUENCE: 126
QGISNH                                                                   6

SEQ ID NO: 127          moltype = AA  length = 7
FEATURE                 Location/Qualifiers
source                  1..7
                        mol_type = protein
                        organism = synthetic construct
SEQUENCE: 127
GASSRQS                                                                  7

SEQ ID NO: 128          moltype = AA  length = 8
FEATURE                 Location/Qualifiers
source                  1..8
                        mol_type = protein
                        organism = synthetic construct
SEQUENCE: 128
LHDRYPYT                                                                 8

SEQ ID NO: 129          moltype = AA  length = 121
FEATURE                 Location/Qualifiers
source                  1..121
                        mol_type = protein
                        organism = synthetic construct
SEQUENCE: 129
EVQLVESGGG LVQPGGSLRL SCAASGFTFS DYSMSWVRQA PGKGLELVAS ISESGHDTYY         60
PDSVKGRFTI SRDNAKNSLY LQMNSLRAED TAVYYCARGI AVAGTRAFDI WGQGTMVTVS        120
S                                                                      121

SEQ ID NO: 130          moltype = AA  length = 8
FEATURE                 Location/Qualifiers
source                  1..8
                        mol_type = protein
                        organism = synthetic construct
SEQUENCE: 130
GFTFSDYS                                                                 8

SEQ ID NO: 131          moltype = AA  length = 8
FEATURE                 Location/Qualifiers
source                  1..8
                        mol_type = protein
                        organism = synthetic construct
SEQUENCE: 131
ISESGHDT                                                                 8

SEQ ID NO: 132          moltype = AA  length = 14
FEATURE                 Location/Qualifiers
source                  1..14
                        mol_type = protein
                        organism = synthetic construct
SEQUENCE: 132
ARGIAVAGTR AFDI                                                         14

SEQ ID NO: 133          moltype = AA  length = 113
FEATURE                 Location/Qualifiers
source                  1..113
                        mol_type = protein
                        organism = synthetic construct
SEQUENCE: 133
DIVMTQSPLS LPVTPGEPAS ISCRSSQSLL YSTGYNYLHW YLQKPGQSPQ LLIYMGSYRA         60
SGVPDRFSGS GSGTDFTLKI SRVEAEDVGV YYCMQALPTP PITFGGGTKV EIK              113

SEQ ID NO: 134          moltype = AA  length = 11
FEATURE                 Location/Qualifiers
source                  1..11
                        mol_type = protein
                        organism = synthetic construct
SEQUENCE: 134
QSLLYSTGYN Y                                                            11

SEQ ID NO: 135          moltype = AA  length = 7
FEATURE                 Location/Qualifiers
source                  1..7
```

```
                        mol_type = protein
                        organism = synthetic construct
SEQUENCE: 135
MGSYRAS                                                                 7

SEQ ID NO: 136          moltype = AA   length = 10
FEATURE                 Location/Qualifiers
source                  1..10
                        mol_type = protein
                        organism = synthetic construct
SEQUENCE: 136
MQALPTPPIT                                                             10

SEQ ID NO: 137          moltype = AA   length = 2003
FEATURE                 Location/Qualifiers
source                  1..2003
                        mol_type = protein
                        organism = Homo sapiens
SEQUENCE: 137
MQPPSLLLLL LLLLLLCVSV VRPRGLLCGS FPEPCANGGT CLSLSLGQGT CQCAPGFLGE        60
TCQFPDPCQN AQLCQNGGSC QALLPAPLGL PSSPSPLTPS FLCTCLPGFT GERCQAKLED       120
PCPPSFCSKR GRCHIQASGR PQCSCMPGWT GEQCQLRDFC SANPCVNGGV CLATYPQIQC       180
HCPPGFEGHA CERDVNECFQ DPGPCPKGTS CHNTLGSFQC LCPVGQEGPR CELRAGPCPP       240
RGCSNGGTCQ LMPEKDSTFH LCLCPPGFIG PDCEVNPDNC VSHQCQNGGT CQDGLDTYTC       300
LCPETWTGWD CSEDVDECET QGPPHCRNGG TCQNSAGSFH CVCVSGWGGT SCEENLDDCI       360
AATCAPGSTC IDRVGSFSCL CPPGRTGLLC HLEDMCLSQP CHGDAQCSTN PLTGSTLCLC       420
QPGYSGPTCH QDLDECLMAQ QGPSPCEHGG SCLNTPGSFN CLCPPGYTGS RCEADHNECL       480
SQPCHPGSTC LDLLATFHCL CPPGLEGQLC EVETNECASA PCLNHADCHD LLNGFQCICL       540
PGFSGTRCEE DIDECRSSPC ANGGQCQDQP GAFHCKCLPG FEGPRCQTEV DECLSDPCPV       600
GASCLDLPGA FFCLCPSGFT GQLCEVPLCA PNLCQPKQIC KDQKDKANCL CPDGSPGCAP       660
PEDNCTCHHG HCQRSSCVCD VGWTGPECEA ELGGCISAPC AHGGTCYPQP SGYNCTCPTG       720
YTGPTCSEEM TACHSGPCLN GGSCNPSPGG YYCTCPPSHT GPQCQTSTDY CVSAPCFNGG       780
TCVNRPGTFS CLCAMGFQGP RCEGKLRPSC ADSPCRNRAT CQDSPQGPRC LCPTGYTGGS       840
CQTLMDLCAQ KPCPRNSHCL QTGPSFHCLC LQGWTGPLCN LPLSSCQKAA LSQGIDVSSL       900
CHNGGLCVDS GPSYFCHCPP GFQGSLCQDH VNPCESRPCQ NGATCMAQPS GYLCQCAPGY       960
DGQNCSKELD ACQSQPCHNH GTCTPKPGGF HCAPPGFVG LRCEGDVDEC LDQPCHPTGT       1020
AACHSLANAF YCQCLPGHTG QWCEVEIDPC HSQPCFHGGT CEATAGSPLG FICHCPKGFE      1080
GPTCSHRAPS CGFHHCHHGG LCLPSPKPGF PPRCACLSGY GGPDCLTPPA PKGCGPPSPC      1140
LYNGSCSETT GLGGPGFRCS CPHSSPGPRC QKPGAKGCEG RSGDGACDAG CSGPGGNWDG      1200
GDCSLGVPDP WKGCPSHSRC WLLFRDGQCH PQCDSEECLF DGYDCETPPA CTPAYDQYCH      1260
DHFHNGHCEK GCNTAECGWD GGDCRPEDGD PEWGPSLALL VVLSPPALDQ QLFALARVLS      1320
LTLRVGLWVR KDRDGRDMVY PYPGARAEEK LGGTRDPTYQ ERAAPQTQPL GKETDSLSAG      1380
FVVVMGVDLS RCGPDHPASR CPWDPGLLLR FLAAMAAVGA LEPLLPGPLL AVHPHAGTAP      1440
PANQLPWPVL CSPVAGVILL ALGALLVLQL IRRRREHGA LWLPPGFTRR PRTQSAPHRR       1500
RPPLGEDSIG LKALKPKAEV DEDGVVMCSG PEEGEEVGQA EETGPPSTCQ LWSLSGGCGA      1560
LPQAAMLTPP QESEMEAPDL DTRGPDGVTP LMSAVCCGEV QSGTFQGAWL GCPEPWEPLL      1620
DGGACPQAHT VGTGETPLHL AARFSRPTAA RRLLEAGANP NQPDRAGRTP LHAAVAADAR      1680
EVCQLLLRSR QTAVDARTED GTTPLMLAAR LAVEDLVEEL IAAQADVGAR DKWGKTALHW      1740
AAAVNNARAA RSLLQAGADK DAQDNREQTP LFLAAREGAV EVAQLLLGLG AARELRDQAG      1800
LAPADVAHQR NHWDLLTLLE GAGPPEARHK ATPGREAGPF PRARTVSVSV PPHGGGALPR      1860
CRTLSAGAGP RGGGACLQAR TWSVDLAARG GGAYSHCRSL SGVGAGGGPT PRGRRFSAGM      1920
RGPRPNPAIM RGRYGVAAGR GGRVSTDDWP CDWVALGACG SASNIPIPPP CLTPSPERGS      1980
PQLDCGPPAL QEMPINQGGE GKK                                             2003

SEQ ID NO: 138          moltype = AA   length = 327
FEATURE                 Location/Qualifiers
source                  1..327
                        mol_type = protein
                        organism = Homo sapiens
SEQUENCE: 138
ASTKGPSVFP LAPCSRSTSE STAALGCLVK DYFPEPVTVS WNSGALTSGV HTFPAVLQSS        60
GLYSLSSVVT VPSSSLGTKT YTCNVDHKPS NTKVDKRVES KYGPPCPSCP APEFLGGPSV      120
FLFPPKPKDT LMISRTPEVT CVVVDVSQED PEVQFNWYVD GVEVHNAKTK PREEQFNSTY      180
RVVSVLTVLH QDWLNGKEYK CKVSNKGLPS SIEKTISKAK GQPREPQVYT LPPSQEEMTK      240
NQVSLTCLVK GFYPSDIAVE WESNGQPENN YKTTPPVLDS DGSFFLYSRL TVDKSRWQEG      300
NVFSCSVMHE ALHNHYTQKS LSLSLGK                                         327

SEQ ID NO: 139          moltype = AA   length = 330
FEATURE                 Location/Qualifiers
source                  1..330
                        mol_type = protein
                        organism = Homo sapiens
SEQUENCE: 139
ASTKGPSVFP LAPSSKSTSG GTAALGCLVK DYFPEPVTVS WNSGALTSGV HTFPAVLQSS        60
GLYSLSSVVT VPSSSLGTQT YICNVNHKPS NTKVDKKVEP KSCDKTHTCP PCPAPELLGG      120
PSVFLFPPKP KDTLMISRTP EVTCVVVDVS HEDPEVKFNW YVDGVEVHNA KTKPREEQYN      180
STYRVVSVLT VLHQDWLNGK EYKCKVSNKA LPAPIEKTIS KAKGQPREPQ VYTLPPSRDE      240
LTKNQVSLTC LVKGFYPSDI AVEWESNGQP ENNYKTTPPV LDSDGSFFLY SKLTVDKSRW      300
QQGNVFSCSV MHEALHNHYT QKSLSLSPGK                                      330
```

```
SEQ ID NO: 140          moltype = AA  length = 326
FEATURE                 Location/Qualifiers
source                  1..326
                        mol_type = protein
                        organism = Homo sapiens
SEQUENCE: 140
ASTKGPSVFP LAPCSRSTSE STAALGCLVK DYFPEPVTVS WNSGALTSGV HTFPAVLQSS    60
GLYSLSSVVT VPSSNFGTQT YTCNVDHKPS NTKVDKTVER KCCVECPPCP APPVAGPSVF   120
LFPPKPKDTL MISRTPEVTC VVVDVSHEDP EVQFNWYVDG VEVHNAKTKP REEQFNSTFR   180
VVSVLTVVHQ DWLNGKEYKC KVSNKGLPAP IEKTISKTKG QPREPQVYTL PPSREEMTKN   240
QVSLTCLVKG FYPSDISVEW ESNGQPENNY KTTPPMLDSD GSFFLYSKLT VDKSRWQQGN   300
VFSCSVMHEA LHNHYTQKSL SLSPGK                                        326

SEQ ID NO: 141          moltype = AA  length = 377
FEATURE                 Location/Qualifiers
source                  1..377
                        mol_type = protein
                        organism = Homo sapiens
SEQUENCE: 141
ASTKGPSVFP LAPCSRSTSG GTAALGCLVK DYFPEPVTVS WNSGALTSGV HTFPAVLQSS    60
GLYSLSSVVT VPSSSLGTQT YTCNVNHKPS NTKVDKRVEL KTPLGDTTHT CPRCPEPKSC   120
DTPPPCPRCP EPKSCDTPPP CPRCPEPKSC DTPPPCPRCP APELLGGPSV FLFPPKPKDT   180
LMISRTPEVT CVVVDVSHED PEVQFKWYVD GVEVHNAKTK PREEQYNSTF RVVSVLTVLH   240
QDWLNGKEYK CKVSNKALPA PIEKTISKTK GQPREPQVYT LPPSREEMTK NQVSLTCLVK   300
GFYPSDIAVE WESSGQPENN YNTTPPMLDS DGSFFLYSKL TVDKSRWQQG NIFSCSVMHE   360
ALHNRFTQKS LSLSPGK                                                  377

SEQ ID NO: 142          moltype = AA  length = 107
FEATURE                 Location/Qualifiers
source                  1..107
                        mol_type = protein
                        organism = Homo sapiens
SEQUENCE: 142
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 143          moltype = AA  length = 106
FEATURE                 Location/Qualifiers
source                  1..106
                        mol_type = protein
                        organism = Homo sapiens
SEQUENCE: 143
GQPKANPTVT LFPPSSEELQ ANKATLVCLI SDFYPGAVTV AWKADGSPVK AGVETTKPSK    60
QSNNKYAASS YLSLTPEQWK SHRSYSCQVT HEGSTVEKTV APTECS                  106

SEQ ID NO: 144          moltype = AA  length = 106
FEATURE                 Location/Qualifiers
source                  1..106
                        mol_type = protein
                        organism = Homo sapiens
SEQUENCE: 144
GQPKAAPSVT LFPPSSEELQ ANKATLVCLI SDFYPGAVTV AWKADSSPVK AGVETTTPSK    60
QSNNKYAASS YLSLTPEQWK SHRSYSCQVT HEGSTVEKTV APTECS                  106

SEQ ID NO: 145          moltype = AA  length = 106
FEATURE                 Location/Qualifiers
source                  1..106
                        mol_type = protein
                        organism = Homo sapiens
SEQUENCE: 145
GQPKAAPSVT LFPPSSEELQ ANKATLVCLI SDFYPGAVTV AWKADSSPVK AGVETTTPSK    60
QSNNKYAASS YLSLTPEQWK SHKSYSCQVT HEGSTVEKTV APTECS                  106

SEQ ID NO: 146          moltype = AA  length = 106
FEATURE                 Location/Qualifiers
source                  1..106
                        mol_type = protein
                        organism = Homo sapiens
SEQUENCE: 146
GQPKAAPSVT LFPPSSEELQ ANKATLVCLI SDFYPGAVKV AWKADGSPVN TGVETTTPSK    60
QSNNKYAASS YLSLTPEQWK SHRSYSCQVT HEGSTVEKTV APAECS                  106
```

```
SEQ ID NO: 147         moltype = AA  length = 106
FEATURE                Location/Qualifiers
source                 1..106
                       mol_type = protein
                       organism = Homo sapiens
SEQUENCE: 147
GQPKAAPSVT LFPPSSEELQ ANKATLVCLV SDFNPGAVTV AWKADGSPVK VGVETTKPSK    60
QSNNKYAASS YLSLTPEQWK SHRSYSCRVT HEGSTVEKTV APAECS                  106
```